US012630829B2

(12) United States Patent
Yamamoto et al.

(10) Patent No.: US 12,630,829 B2
(45) Date of Patent: May 19, 2026

(54) GENE ENCODING CYTOCHROME P450 AND USE THEREOF

(71) Applicant: KUMIAI CHEMICAL INDUSTRY CO., LTD., Tokyo (JP)

(72) Inventors: Shunsuke Yamamoto, Tokyo (JP); Kiyoshi Kawai, Tokyo (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 11 days.

(21) Appl. No.: 18/009,795

(22) PCT Filed: Jun. 24, 2021

(86) PCT No.: PCT/JP2021/024038
§ 371 (c)(1),
(2) Date: Dec. 12, 2022

(87) PCT Pub. No.: WO2021/261572
PCT Pub. Date: Dec. 30, 2021

(65) Prior Publication Data
US 2023/0235335 A1 Jul. 27, 2023

(30) Foreign Application Priority Data

Jun. 26, 2020 (JP) ................................. 2020-110269
Aug. 7, 2020 (JP) ................................. 2020-134782

(51) Int. Cl.
*C12N 15/52* (2006.01)
*C12N 9/02* (2006.01)
*C12N 15/82* (2006.01)

(52) U.S. Cl.
CPC ........... *C12N 15/52* (2013.01); *C12N 9/0079* (2013.01); *C12N 15/8243* (2013.01); *C12Y 114/15004* (2013.01)

(58) Field of Classification Search
None
See application file for complete search history.

(56) References Cited

U.S. PATENT DOCUMENTS

| | | | |
|---|---|---|---|
| 8,049,063 B2 | 11/2011 | Tu et al. | |
| 9,657,307 B2 * | 5/2017 | Shen ................... | C07K 14/415 |
| 2014/0173776 A1 | 6/2014 | Tresch et al. | |

(Continued)

FOREIGN PATENT DOCUMENTS

| | | |
|---|---|---|
| KR | 10-2018-0028459 A | 3/2018 |
| WO | WO 2009/134339 A2 | 11/2009 |

(Continued)

OTHER PUBLICATIONS

Extended European Search Report for European Application No. 21827944.6, dated Jun. 17, 2024.

(Continued)

*Primary Examiner* — Amjad Abraham
*Assistant Examiner* — Dequantarius Javon Speed
(74) *Attorney, Agent, or Firm* — Birch, Stewart, Kolasch & Birch, LLP

(57) ABSTRACT

Metabolic activity is exhibited against a larger number of compounds having different acting properties. A cytochrome P450 gene encodes a protein having an amino acid sequence of any of SEQ ID NOS: 2, 4, 6, and 8.

2 Claims, 21 Drawing Sheets

Specification includes a Sequence Listing.

```
CYP81A6     1:MDNAYIIA:LSVAILFLLHYYLLGRGNG-------GAARLPPGPPAVPILGHLHLVKKPMHATMSRLAERYGPVFSLRLGSRRAVVVSSPGCARECFTEHD 94
AK375492    1:MDKAY-IA:LSFTFLFLLHYILGKVSNGRR--SKGDVQLPPSPRPIPFLGHLHLLEKPFHVALCRLAARLGPVFSLRLGSRRAVVVSSADCARECFTEHD 97
AK369081    1:MDKAS-IAVLSLAFLFLLHYILGKRSDGRRGKGKGAVQLPPSPPAVPFFGHLHLVEKPLHAALCRLGARHGPVFSLRLGARNAVVVSSPACARECFTDHD 99
            **. *. ** ** . .****** *.  . .* . . * .  . *. . * . *. **** **. .* . ** .* ********** * ****** ********.**

CYP81A6    95:VTFANRPRFESGLLVSFNGAALATASYGAHWRNLRRIVAVQLLSAHRVGLMSGLIAGEVRAMVRRMYRAAAASP--AGAARIQLKRRLFEVSLSVLMETI 192
AK375492   98:VIFANRPQFPSGLLVSFDGTALSTSSYGPHWRNLRRVAAVQLLSAHRVACMSGVIAGEVRAMARRLFRSAEASPGGGGAARVQLKRRLFELSLSVLMETI 197
AK369081  100:VAFANRPQFPSQMLVSYGGTSLVSSSYGPHWRNLRRVAAVRLLSAHRVAGMSGVIAAEVRAMARRLYRAAAASP---GGAARVELKRSLFELSLSVLMETI 197
            * *****. *. **. ***. *. .* . .***. *********. . **. ********. ***. **. ***** . **. .* . * *** . . **** . . *** .*** *******

CYP81A6   193:AHTKATRPETDPDTDMSVEAGEFKQVVDEI:FH:GAANLWDYLPALRWFDVFGVRRKILAAVSRRDAFLRRLIDAERRRLDD-GDEGEKKSMIAVLLTLQ 291
AK375492  198:AQTKGTRSEADADTDMSVEAQEFKKVVDEI:PYLGAANTWDYLPVVRWFDVFGVRNKILAAVSRRDAFLHRLIDAERRRLDGGGAEADKKSMIAVLLTLQ 297
AK369081  198:ARTKGTRSEADADTDMSLEAQEFKQVVDEI:PLIGAANLWDYLPVMRWFDVSGVRSRILATVSRRDAFLHRLIDAERRRMEEGGDEGEKKSMIAVLLTLQ 297
            * **. ** *. *. ***** ****** . ****** . **** *. . ***. *. **** ***. . ****. ********* . ********** . . *. * . *********

CYP81A6   292:KTEPEVYIDNMITALTANLFGAGTETTSTTSEWAMSLLLNHPDTLKKAQAEIDASVGNSRL:TADDVIRLGYLQCIVRETLRLYPAAPMLLPHESSADCK 391
AK375492  298:KTEPEVYTDTMITALCSNLFGAGTETTSTTTEWAMSLLLNHPAALRKAQAEIDAAVGTSRLVTADDVPRLAYLQCIVSETLRLYPATPMLLPHQSSADCK 397
AK369081  298:KTEPELYTDQMIIALCANMFVAGTETTSTTI EWAMSLLLNHPAALKKAQAEIDASIGTSRMVAADDVPRLSYLQCI INETLRMYPAAPLLLPHESSADCK 397
            ***** . *** *** **. *. *. ********** ********* .* ********** .* . ** . .* . ***** . ** ****. *** * **** *******

CYP81A6   392:VGGYNIPRGSMLLINAYAIHRDPAVWEEPEKFMPERFEDGGCDGNLLMPFGMGRRRCPGETLALRTVGLVLGTLIQCFDWERVDGVEVDMTEGGGLTIPK 491
AK375492  398:VGGYNVPSGTMLMVNAYAIHRDPAAWERPLEFVPERFEDGKAEGRFMIPFGMGRRRCPGETLALRTIGMVLATLVQCFDWDRVDGKEVDMTESGGLTIPK 497
AK369081  398:VGGYDVPSGTMLIVNAYAIHRDPATWEDPTAERPERFEDGKGDGLLLMPFGMGRRRCPGEALALQTVGVVLGMLVQCFDWDRVDGVEVDMTEGVGITMPK 497
            ****. *. *. ** .*********** ** . *  * .*********. . *  .  . * . ************* *** . * . * . * . ***** . **** .****** . . * . * . **

CYP81A6   492:VVPLEAMCRPRDAMGGVLRELV 513
AK375492  498:AVPLEAVCRPRAAMRDVLQSL- 518
AK369081  498:SVALEAVCRPRAAMRDVLHKL- 518
            *. ***. **** . **. .** . *
```

(56) References Cited

U.S. PATENT DOCUMENTS

2015/0322453 A1* 11/2015 Tresch ................. C12N 9/0079
800/300

FOREIGN PATENT DOCUMENTS

WO    WO 2014/097085 A1    6/2014
WO    WO 2017/009148 A1    1/2017

OTHER PUBLICATIONS

Matsumoto et al., "Comprehensive Sequence Analysis of 24,783 Barley Full-Length cDNAs Derived from 12 Clone Libraries," Plant Physiology, vol. 156, May 2011, pp. 20-28.
Zhang et al., "Cloning and sequence analysis of a cytochrome P450 (TaP450) gene from wheat (*Triticum aestivum* L.)," Mailei Zuowu Xuebao, vol. 34, Issue 7, Jul. 15, 2014, 1 page total.
International Search Report (PCT/ISA/210), issued in PCT/JP2021/024038, dated Jul. 20, 2021.
Ohkawa et al., "Metabolism of agrochemicals and related environmental chemicals based on cytochrome P450s in mammals and plants", Pest Manag Sci, 2015, vol. 71, pp. 824-828.
Pan et al., "Map-based cloning of a novel rice cytochrome P450 gene CYP81A6 that confers resistance to two different classes of herbicides", Plant Mol Biol, 2006, vol. 61, pp. 933-943.
Saika et al., "A Novel Rice Cytochrome P450 Gene, CYP72A31, Confers Tolerance to Acetolactate Synthase-Inhibiting Herbicides in Rice and Arabidopsis", Plant Physiology, Nov. 2014, vol. 166, pp. 1232-1240.
Siminszky, "Plant cytochrome P450-mediated herbicide metabolism", Phytochem Rev, 2006, vol. 5, pp. 445-458.
UniProt [online], Accession No. A0A059UJ35, 2014, [retrieved on Jul. 9, 2021], Internet: <https://www.uniprot.org/uniprot/A0A059UJ35>.
UniProt [online], Accession No. A0A3B6KPP6, 2018, [retrieved on Jul. 9, 2021], Internet: <https://www.uniprot.org/uniprot/A0A3B6KPP6>.
Written Opinion of the International Searching Authority (PCT/ISA/237), issued in PCT/JP2021/024038, dated Jul. 20, 2021.
Yamamoto et al., "Study on the mode of action and metabolic detoxification of a novel herbicide, fenquinotrione", The 26th Asian-Pacific Weed Science Society Conference program book, 2017, pp. 232.

* cited by examiner

Fig. 1

```
CYP81A6    1:MDNAYIIAILSVAILFLLHYLLGRGNG------GAARLPPGPPAVPILGHLHLVKKPMHATMSRLAERYGPVFSLRLGSRRAVVSSPGCARECFTEHD  94
AK375492   1:MDKAY-IAILSFTFLFLLHYILGKVSNGRR--SKGDVQLPPSPRPIPFLGHLHLLEKPFHVALCRLAARLGPVFSLRLGSRRAVVSSADCARECFTEHD  97
AK369081   1:MDKAS-IAVLSLAFLFLLHYILGKRSDGRRGKGKGAVQLPPSPPAVPFFGHLHLVEKPLHAALCRLGARHGPVFSLRLGARNAVVVSSPACARECFTDHD  99
             **.*. .**.*.** ******* .  .    . . *. .****.*. **  . **  ..**  ***** **

CYP81A6   95:VTFANRPRFESQLLVSFNGAALATASYGAHWRNLRRIVAVQLLSAHRVGLMSGLIAGEVRAMVRRMYRAAAASP---AGAARIQLKRRLFEVSLSVLMETI 192
AK375492  98:VIFANRPQFPSQLLVSFDGTALSTSSYGPHWRNLRRVAAVQLLSAHRVACMSGVIAGEVRAMARRLFRSAEASPGGGGAARVQLKRRLFELSLSVLMETI 197
AK369081 100:VAFANRPQFPSQMLVSYGGTSLVSSSYGPHWRNLRRVAAVRLLSAHRVAGMSGVIAAEVRAMARRLYRAAAASP---GGAARVELKRSLFELSLSVLMETI 197
            * ****** .*** . **  . .*****.*** .  ** .*** .*** ** . *** *** .*.  *****

CYP81A6  193:AHTKATRPETDPDTDMSVEAQEFKQVVDEIIPHIGAANLWDYLPALRWFDVFGVRRKILAAVSRRDAFLRRLIDAERRRLDD-GDEGEKKSMIAVLLTLQ 291
AK375492 198:AQTKGTRSEADADTDMSVEAQEFKKVVDEIIPYLGAANTWDYLPVVRWFDVFGVRNKILAAVSRRDAFLHRLIDAERRRLDGGGAEADKKSMIAVLLTLQ 297
AK369081 198:ARTKGTRSEADADTDMSLEAQEFKQVVDEIIPLIGAANLWDYLPVMRWFDVSGVRSRILATVSRRDAFLHRLIDAERRRMEEGGDEGEKKSMIAVLLTLQ 297
            * .** .. . ***** .***** ***** ** .*** ****. .*****.**. ***.******* .********    .* ********.*********

CYP81A6  292:KTEPEVYTDNMITALTANLFGAGTETTSTTSEWAMSLLLNHPDTLKKAQAEIDASVGNSRLITADDVTRLGYLQCIVRETLRLYPAAPMLLPHESSADCK 391
AK375492 298:KTEPEVYTDTMITALCSNLFGAGTETTSTTTEWAMSLLLNHPAALRKAQAEIDAAVGTSRLVTADDVPRLAYLQCIVSETLRLYPATPMLLPHQSSADCK 397
AK369081 298:KTEPELYTDQMIIALCANMFVAGTETTSTTIEWAMSLLLNHPAALKKAQAEIDASIGTSRMVAADDVPRLSYLQCIINETLRMYPAAPLLLPHESSADCK 397
            ***** .**  * ** .* * *********. *********  .* *******. * .** ** .*** .***. .*** **** ** .**. *****

CYP81A6  392:VGGYNIPRGSMLLINAYAIHRDPAVWEEPEKFMPERFEDGGGCDGNLLMPFGMGRRRCPGETLALRTVGLVLGTLIQCFDWERVDGVEVDMTEGGLTIPK 491
AK375492 398:VGGYNVPSGTMLMVNAYAIHRDPAAWERPLEFVPERFEDGKAEGRFMIPFGMGRRRCPGETLALRTIGMVLATLVQCFDWDRVDGKEVDMTESGGLTIPK 497
AK369081 398:VGGYDVPSGTMLIVNAYAIHRDPATWEDPTAFRPERFEDGKGDGLLLMPFGMGRRRCPGEALALQTVGVVLGMLVQCFDWDRVDGVEVDMTEGVGITMPK 497
            **** * .* ** .**********. *.  * .******* . * .*.************** *** .**. *.* .**** ***** ***** .* *.**

CYP81A6  492:VVPLEAMCRPRDAMGGVLRELV 513
AK375492 498:AVPLEAVCRPRAAMRDVLQSL- 518
AK369081 498:SVALEAVCRPRAAMRDVLHKL- 518
             * .*** ****.**  **.
```

Fig. 2

```
CYP81A6    1:MDNAYIIAILSVAILFLLHYYL--LGRG--NGGAARLPPGPPAVPILGHLHLVKKPMHATMSRLAERYGPVFSLRLGSRRAVVVSSPGCARECFTEHDVT  96
AK454412   1:MDKAY-IAILTIAFLFLIHYVLGNGRRG--GKGAAQLPPSPPAIPFLGHLHLLEKPFHAALRRLAARLGPVFSLRLGSRRAVVVSSAECARECFTEHDVT  97
KJ541960   1:MDKAY-IAILSFAFLFLLHYILGKVSNGRRSKGAVQLPPSPQAIPFLGHLHLLEKPFHAALCRLAERLGPVFSLRLGSRRAVVVSSAECARECFTEHDVI  99
             **.** ****.  *  *.*  *.  *   .    *     *  ******  ** ** **. .  ******************* . **************

CYP81A6    97:FANRPRFESQLLVSFNGAALATASYGAHWRNLRRIVAVQLLSAHRVGLMSGLIAGEVRAMVRRMYRAAAASPA--GAARIQLKRRLFEVSLSVLMETIAH  194
AK454412   98:FANRPRFPSQLLVSFDGAALVTSSYGPHWRNLRRVAAVQLLSAHRVACMSGVIAGEVRAMARRLFRAAAASPGGDGAARVQLKRRLFELSLSVLMETIAQ  197
KJ541960  100:FADRPQFPSQLLVSFDGIALSTSSYGPHWRNLRRVAAVQLLSAHRVACMSGVIGGEVRAMARRLFRAAAASPGGDGAARVQLKRRLFELSLSVLMETIAQ  199
             **.** * ****** * .*** ** ** ******* *.******** .**.* ******. ** ******  *** **.******** ***********

CYP81A6   195:TKATRPETDPDTDMSVEAQEFKQVVDEIIPHIGAANLWDYLPALRWFDFGVRRKILAAVSRRDAFLRRLIDAERRRLDD-GDEGEKKSMIAVLLTLQKT  293
AK454412  198:TKATRSEADADTDMSVEAQEFKKVVDEIPYLGAANTWDYLPVLRWFDVFGVRNKILAAVSRRDAFMLRLIDNERRRLDDAGTEGDKKSMIAVLLNLQKT  297
KJ541960  200:TKATRSEADADTDMSEEAQEFKKVVDELPYLGAANTWDYLPVLRWFDVFGVRNKILAAVSRRDAFLHRLIDNERRRLDNAGTEGDKKSMIAVLLNLQKT  299
             ***** *  ****** ****** ****  . **** ***** ****** ***.**********.  *.**.*****.   * **.*********.****

CYP81A6   294:EPEVYTDNMITALTANLFGAGTETTSTTSEWAMSLLLNHPDTLKKAQAEIDASVGNSRLITADDVTRLGYLQCIVRETLRLYPAAPMLLPHESSADCKVG  393
AK454412  298:EPEVYADTMITALCANLFGAGTETTSTTTEWAMSLLLNHPAALKKAQAEIDAAVGTSRLVTADDVPRLAYLQCIVSETLRLYPAAPMLLPHESSADCKVG  397
KJ541960  300:EPEVYTDTMITALCANLFGAGTETTSTTTEWAMSLLLNHPAALRKAQAEIDAAVGTSRLVTADDVPRLAYLQCIVSETLRLYPAAPMLLPHQSSADCKVG  399
             ***** *.***** **************.****************   *******.  ***.***.***  ** ****.* *** ****************

CYP81A6   394:GYNIPRGSMLLINAYAIHRDPAVWEEPEKFMPERFEDGGCDGNLLMPFGMGRRRCPGETLALRTVGLVLGTLIQCFDWERVDGVEVDMTEGGGLTIPKVV  493
AK454412  398:GYNVPSGTMLMVNAYAIHRDPAAWERPLEFVPERFEDGKAEGRFMIPFGMGRRRCPGETLALRTIGMVLATLVQCFDWERVDGAEVDMTEGGGLTIPKVV  497
KJ541960  400:GYNVPSGTMLMVNAYAIHRDPAAWERPLEFVPERFENGKAEGRFMIPFGMGRRRCPGETLALRTIGMVLATLVQCFDWERVDGAEVDMTEGGGLTIPKVV  499
             ***.* *.**.. ******** ** *  * ****  *     *.** ***********.  **.  ** * *** ********* ****************

CYP81A6   494:PLEAMCRPRDAMGGVLRELV  513
AK454412  498:PLEAVCRPRPAMRDVLQSL-  516
KJ541960  500:PLEAVCRPRPAMRDVLQSL-  518
             **** ****.**  **.*  .
```

1kb  (1)  (2)  (3)  (4) 100 bp (1): Tamarai, (2): Apache, (3): Norin No. 61, (4): Bolak

Fig. 10-1

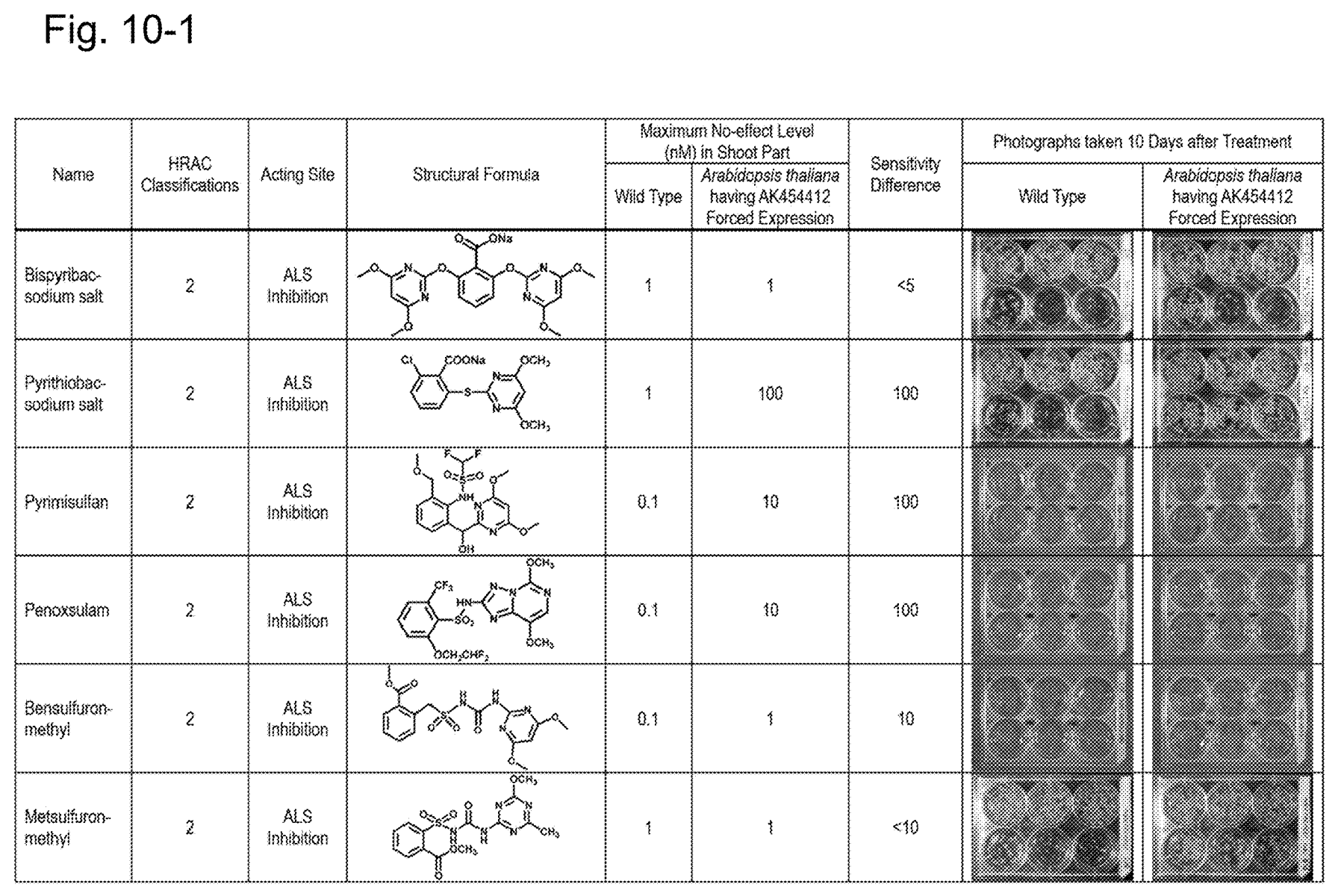

| Name | HRAC Classifications | Acting Site | Structural Formula | Maximum No-effect Level (nM) in Shoot Part | | Sensitivity Difference | Photographs taken 10 Days after Treatment | |
|---|---|---|---|---|---|---|---|---|
| | | | | Wild Type | Arabidopsis thaliana having AK454412 Forced Expression | | Wild Type | Arabidopsis thaliana having AK454412 Forced Expression |
| Bispyribac-sodium salt | 2 | ALS Inhibition | | 1 | 1 | <5 | | |
| Pyrithiobac-sodium salt | 2 | ALS Inhibition | | 1 | 100 | 100 | | |
| Pyrimisulfan | 2 | ALS Inhibition | | 0.1 | 10 | 100 | | |
| Penoxsulam | 2 | ALS Inhibition | | 0.1 | 10 | 100 | | |
| Bensulfuron-methyl | 2 | ALS Inhibition | | 0.1 | 1 | 10 | | |
| Metsulfuron-methyl | 2 | ALS Inhibition | | 1 | 1 | <10 | | |

Fig. 10-2

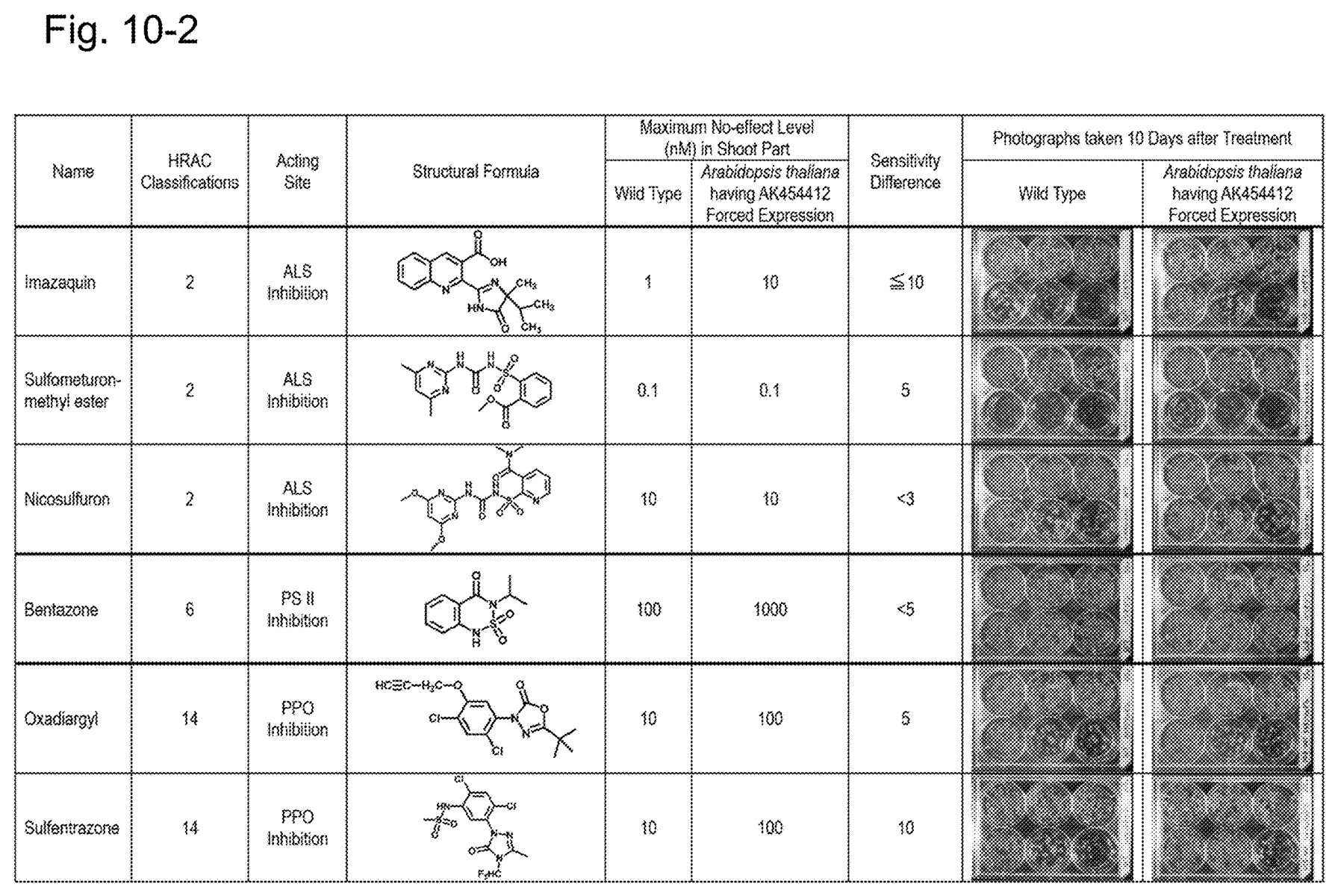

| Name | HRAC Classifications | Acting Site | Structural Formula | Maximum No-effect Level (nM) in Shoot Part | | Sensitivity Difference | Photographs taken 10 Days after Treatment | |
|---|---|---|---|---|---|---|---|---|
| | | | | Wild Type | Arabidopsis thaliana having AK454412 Forced Expression | | Wild Type | Arabidopsis thaliana having AK454412 Forced Expression |
| Imazaquin | 2 | ALS Inhibition | | 1 | 10 | ≦10 | | |
| Sulfometuron-methyl ester | 2 | ALS Inhibition | | 0.1 | 0.1 | 5 | | |
| Nicosulfuron | 2 | ALS Inhibition | | 10 | 10 | <3 | | |
| Bentazone | 6 | PS II Inhibition | | 100 | 1000 | <5 | | |
| Oxadiargyl | 14 | PPO Inhibition | | 10 | 100 | 5 | | |
| Sulfentrazone | 14 | PPO Inhibition | | 10 | 100 | 10 | | |

Fig. 10-3

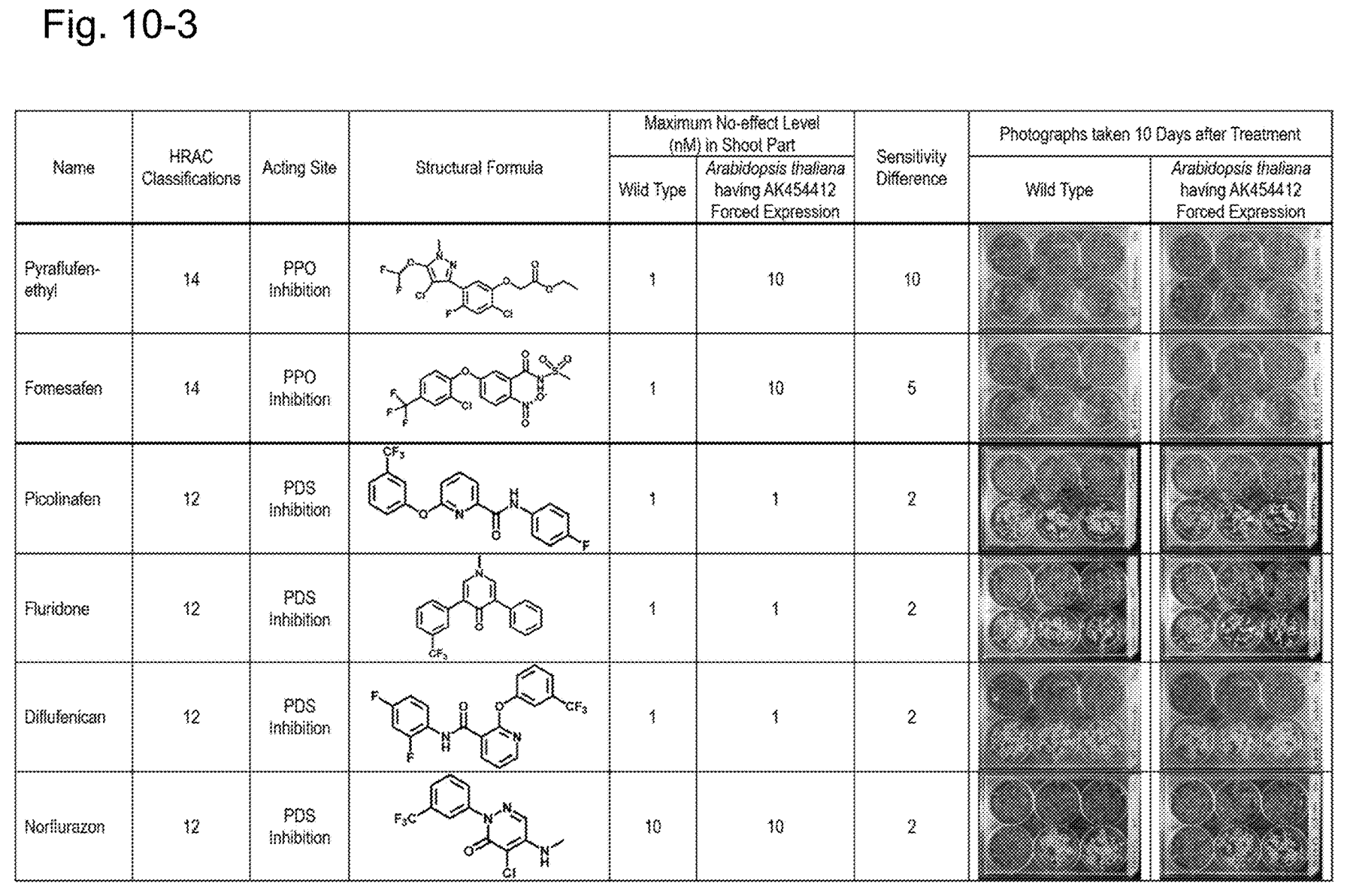

| Name | HRAC Classifications | Acting Site | Structural Formula | Maximum No-effect Level (nM) in Shoot Part | | Sensitivity Difference | Photographs taken 10 Days after Treatment | |
|---|---|---|---|---|---|---|---|---|
| | | | | Wild Type | Arabidopsis thaliana having AK454412 Forced Expression | | Wild Type | Arabidopsis thaliana having AK454412 Forced Expression |
| Pyraflufen-ethyl | 14 | PPO inhibition | | 1 | 10 | 10 | | |
| Fomesafen | 14 | PPO inhibition | | 1 | 10 | 5 | | |
| Picolinafen | 12 | PDS inhibition | | 1 | 1 | 2 | | |
| Fluridone | 12 | PDS inhibition | | 1 | 1 | 2 | | |
| Diflufenican | 12 | PDS inhibition | | 1 | 1 | 2 | | |
| Norflurazon | 12 | PDS inhibition | | 10 | 10 | 2 | | |

Fig. 10-4

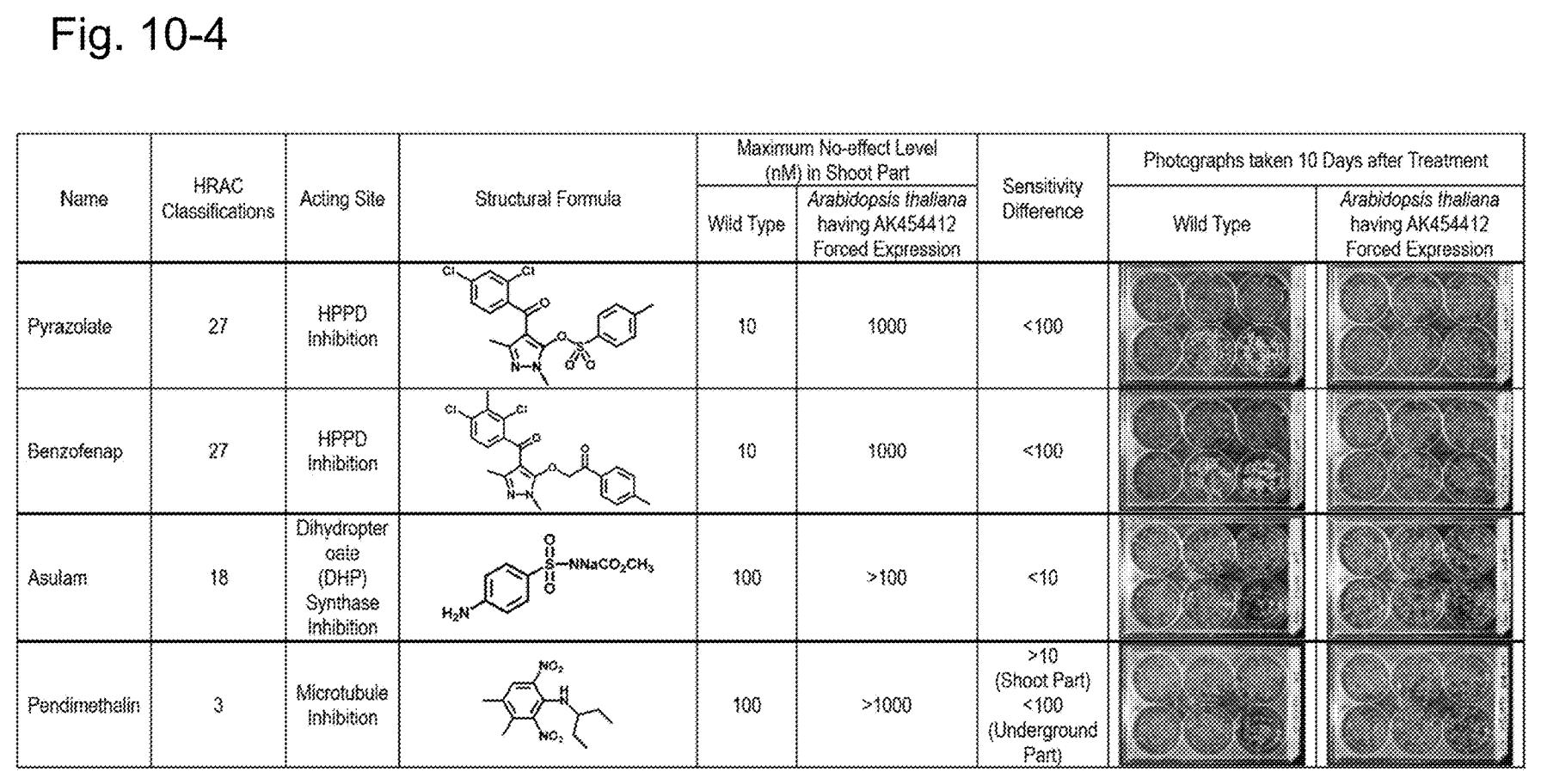

| Name | HRAC Classifications | Acting Site | Structural Formula | Maximum No-effect Level (nM) in Shoot Part | | Sensitivity Difference | Photographs taken 10 Days after Treatment | |
|---|---|---|---|---|---|---|---|---|
| | | | | Wild Type | Arabidopsis thaliana having AK454412 Forced Expression | | Wild Type | Arabidopsis thaliana having AK454412 Forced Expression |
| Pyrazolate | 27 | HPPD Inhibition | | 10 | 1000 | <100 | | |
| Benzofenap | 27 | HPPD Inhibition | | 10 | 1000 | <100 | | |
| Asulam | 18 | Dihydropteroate (DHP) Synthase Inhibition | | 100 | >100 | <10 | | |
| Pendimethalin | 3 | Microtubule Inhibition | | 100 | >1000 | >10 (Shoot Part) <100 (Underground Part) | | |

M1: 1 kbp ladder, M2: 100 bp ladder
(1): Yumekaori, (2): Hanamanten, (3): Yumeseiki, (4): Norin NO. 61, (5): Kitahonami,
(6): Kinuhikari, (7): Shunyou, (8): Bolak, (9): entinel, (10): EGA Wedgtail,
(11): Gatalina, (12): Yipti, (13): Orlo, (14): Mirabox, (15): Biensor, (16): Argeles,
(17): Tamarai, (18): Jandaroi
(Underlined: Durum wheat breeds)

GENE ENCODING CYTOCHROME P450 AND USE THEREOF

REFERENCE TO SEQUENCE LISTING

This application includes an electronically submitted sequence listing in .txt format. The .txt file contains a sequence listing entitled "1254-0666PUS1_ST25.txt" created on Dec. 23, 2024 and is 108,577 bytes in size. The sequence listing contained in this .txt file is part of the specification and is hereby incorporated by reference herein in its entirety.

TECHNICAL FIELD

The present invention relates to a gene encoding a cytochrome P450 having a characteristic substrate specificity, and use thereof.

BACKGROUND ART

Cytochrome P450 (hereinafter P450 or CYP) is a group of hemoproteins that are present in a wide range of species including microorganisms, plants, and animals. P450 has monooxygenase activity as its function, and there are a large number of molecular species having various substrate specificities. There are 57 molecular species of P450 in humans, and as for plants, there are about 250 molecular species in *Arabidopsis thaliana*, and about 450 molecular species in a rice plant. P450 is known as an enzyme involved mainly in drug metabolism in humans, and involved in secondary metabolism or drug metabolism in plants.

A P450 involved in drug metabolism in humans catalyzes, as each of the molecular species, a large number of substrates having different acting properties, and on the other hand, it has been revealed that a plant P450 has very high substrate specificity, and recognizes and metabolically degrades only limited compounds having limited acting properties (Non Patent Literature 1: Hideo Ohkawa and Hideyuki Inui, Pest Manag Sci 2015; 71: 824-828). In particular, there are a very small number of P450s specified to be involved in drug metabolism in crops including: CYP71A10 of soybean, CYP71C6v1 of wheat (Non Patent Literature 2: Balazs Siminszky, Phytochem Rev (2006) 5:445-458), and CYP81A6 (Non Patent Literature 3: Gang Pan et al, Plant Mol Biol (2006) 61:933-943) and CYP72A31 (Non Patent Literature 4: Hiroaki Saika et al, Plant Physiology (2014) Vol. 166, pp. 1232-1240) of a rice plant, and there are a very limited number of drugs that can be metabolically degraded by these P450s. Specifically, it has been revealed that CYP71A10, CYP71C6v1, and CYP72A31 respectively metabolically degrade a photosystem II inhibitor such as chlorotoluron, an ALS inhibitor such as chlorsulfuron, and an ALS inhibitor such as bispyribac-sodium salt.

In particular, as for CYP81A6 of a rice plant disclosed in Non Patent Literature 3, it is disclosed that CYP81A6 has substrate specificity to bentazone and sulfonylurea, and that a transformed plant having resistance to bentazone and sulfonylurea is produced by using CYP81A6 (Patent Literature 1: U.S. Pat. No. 8,049,063 B2). Besides, Non Patent Literature 5 (The 26th Asian-Pacific Weed Science Society Conference) discloses that CYP81A6 is involved in metabolism of fenquinotrione.

CITATION LIST

Non Patent Literature

Non Patent Literature 1: Hideo Ohkawa and Hideyuki Inui, Pest Manag Sci 2015; 71: 824-828

Non Patent Literature 2: Balazs Simiznszky, Phytochem Rev (2006) 5:445-458

Non Patent Literature 3: Gang Pan et al, Plant Mol Biol (2006) 61:933-943

Non Patent Literature 4: Hiroaki Saika et al, Plant Physiology (2014) Vol. 166, pp. 1232-1240

Non Patent Literature 5: The 26th Asian-Pacific Weed Science Society Conference program book (2017) pp. 232

PATENT LITERATURE

Patent Literature 1: U.S. Pat. No. 8,049,063 B2

SUMMARY OF INVENTION

Technical Problem

To date, no plant P450 has been known, however, to have metabolic activity against a large number of compounds. Therefore, in consideration of the above-described circumstances, an object of the present invention is to provide a gene encoding a novel cytochrome P450 having metabolic activity against a larger number of compounds as compared to known P450s, and use thereof.

Solution to Problem

The present inventors made earnest studies to solve the above-described problem, and as a result, have succeeded in identifying a gene encoding a cytochrome P450 having metabolic activity against a variety of compounds having different acting properties against plants, and thus, the present invention was accomplished.

Specifically, the present invention encompasses the following:

(1) A cytochrome P450 gene encoding a protein described in any of the following (a) to (c):

(a) a protein comprising an amino acid sequence of any of SEQ ID NOS: 2, 4, 6, and 8;

(b) a protein comprising an amino acid sequence having 80% or more identity to the amino acid sequence of any of SEQ ID NOS: 2, 4, 6, and 8, and having metabolic activity against a microtubule assembly inhibitor classified as code 3 of Herbicide Resistance Action Committee (HRAC) classifications, a carotenoid biosynthesis inhibitor in phytoene desaturase (PDS) classified as code 12 of HRAC classifications, a protoporphyrinogen oxidase inhibitor classified as code 14 of HRAC classifications, and a dihydropteroate synthase inhibitor classified as code 18 of HRAC classifications; and (c) a protein comprising an amino acid sequence encoded by a polynucleotide that hybridizes, under stringent conditions, with a polynucleotide consisting of a nucleotide sequence complementary to a nucleotide sequence of any of SEQ ID NO: 1, 3, 5, and 7, and having metabolic activity against a microtubule assembly inhibitor classified as code 3 of HRAC classifications, a carotenoid biosynthesis inhibitor in phytoene desaturase (PDS) classified as code 12 of HRAC classifications, a protoporphyrinogen oxidase inhibitor classified as code 14 of HRAC classifications, and a dihydropteroate synthase inhibitor classified as code 18 of HRAC classifications.

(2) The cytochrome P450 gene according to (1), wherein the protein consists of an amino acid sequence of (d) or (e):

(d) an amino acid sequence of any of SEQ ID NOS: 10, 12, 14, and 16; or (e) an amino acid sequence having 80% or more identity to the amino acid sequence of any of SEQ ID NOS: 10, 12, 14, and 16.

(3) The cytochrome P450 gene according to (1), wherein the protein has metabolic activity against an acetolactate synthase inhibitor classified as code 2 of HRAC classifications, a microtubule assembly inhibitor classified as code 3 of HRAC classifications, a photosystem II inhibitor classified as code 6 of HRAC classification, a carotenoid biosynthesis inhibitor in phytoene desaturase (PDS) classified as code 12 of HRAC classifications, a protoporphyrinogen oxidase inhibitor classified as code 14 of HRAC classifications, a dihydropteroate synthase inhibitor classified as code 18 of HRAC classifications, and a 4-hydroxyphenylpyruvate dioxygenase inhibitor classified as code 27 of HRAC classifications.

(4) An expression vector comprising the cytochrome P450 gene according to any of (1) to (3).

(5) A transformant comprising the expression vector according to (4).

(6) A transgenic plant comprising the expression vector according to (4).

(7) The transgenic plant according to (6), wherein the plant is a plant body, a plant organ, a plant tissue, or a cultured plant cell.

(8) A method for producing a plant having resistance to a microtubule assembly inhibitor classified as code 3 of HRAC classifications, a carotenoid biosynthesis inhibitor in phytoene desaturase (PDS) classified as code 12 of HRAC classifications, a protoporphyrinogen oxidase inhibitor classified as code 14 of HRAC classifications, and a dihydropteroate synthase inhibitor classified as code 18 of HRAC classifications, the method comprising culturing or cultivating the transgenic plant according to (6) or (7).

(9) A method for controlling weed noxious to the transgenic plant according to (6) or (7), comprising treating a field used for cultivating the transgenic plant with at least one inhibitor selected from the group consisting of an acetolactate synthase inhibitor classified as code 2 of HRAC classifications, a microtubule assembly inhibitor classified as code 3 of HRAC classifications, a photosystem II inhibitor classified as code 6 of HRAC classification, a carotenoid biosynthesis inhibitor in phytoene desaturase (PDS) classified as code 12 of HRAC classifications, a protoporphyrinogen oxidase inhibitor classified as code 14 of HRAC classifications, a dihydropteroate synthase inhibitor classified as code 18 of HRAC classifications, and a 4-hydroxyphenylpyruvate dioxygenase inhibitor classified as code 27 of HRAC classifications.

(10) A transformation method comprising: a step of introducing, into a host cell, an expression vector comprising the cytochrome P450 gene according to any of (1) to (3), and an additional gene; and a step of selecting, as a transformant, a cell that grows in the presence of at least one inhibitor selected from the group consisting of an acetolactate synthase inhibitor classified as code 2 of HRAC classifications, a microtubule assembly inhibitor classified as code 3 of HRAC classifications, a photosystem II inhibitor classified as code 6 of HRAC classification, a carotenoid biosynthesis inhibitor in phytoene desaturase (PDS) classified as code 12 of HRAC classifications, a protoporphyrinogen oxidase inhibitor classified as code 14 of HRAC classifications, a dihydropteroate synthase inhibitor classified as code 18 of HRAC classifications, and a 4-hydroxyphenylpyruvate dioxygenase inhibitor classified as code 27 of HRAC classifications.

The present specification encompasses the disclosed contents of JP Patent Application No. 2020-110269 and JP Patent Application No. 2020-134782, based on which the present application claims the benefit of priority.

Advantageous Effects of Invention

According to the present invention, a cytochrome P450 gene having metabolic activity against a large number of drugs having different acting properties can be provided. When the cytochrome P450 gene of the present invention is used, resistance to the large number of drugs having different acting properties can be imparted to plants. Besides, when the cytochrome P450 gene of the present invention is used as a selection marker gene, a totally novel transformation method can be constructed. In addition, the cytochrome P450 gene of the present invention can be used as a resistance marker gene serving as an index of resistance to a large number of drugs having different acting properties.

BRIEF DESCRIPTION OF DRAWINGS

FIG. 1 is a diagram illustrating results of multiple alignment analysis of CYP81A6 (SEQ ID NO: 39), AK375492 (SEQ ID NO: 16), and AK369081 (SEQ ID NO: 14).

FIG. 2 is a diagram illustrating results of multiple alignment analysis of CYP81A6 (SEQ ID NO: 39), KJ541960 (SEQ ID NO: 12), and AK454412 (SEQ ID NO: 10).

FIG. 7-1 is a characteristic diagram illustrating a result of LC/MS analysis performed on a negative control plot (empty vector expression crude enzyme reaction plot).

FIG. 7-2 is a characteristic diagram illustrating a result of LC/MS analysis performed on an AK454412-TaCPR co-expression crude enzyme reaction plot.

FIG. 10-1 is a table showing verification results on resistance to various herbicides in wild type *Arabidopsis thaliana* and *Arabidopsis thaliana* having AK454412 forced expression.

FIG. 10-2 is a table showing verification results on resistance to various herbicides in wild type *Arabidopsis thaliana* and *Arabidopsis thaliana* having AK454412 forced expression.

FIG. 10-3 is a table showing verification results on resistance to various herbicides of wild type *Arabidopsis thaliana* and *Arabidopsis thaliana* having AK454412 forced expression.

FIG. 10-4 is a table showing verification results on resistance to various herbicides of wild type *Arabidopsis thaliana* and *Arabidopsis thaliana* having AK454412 forced expression.

DESCRIPTION OF EMBODIMENTS

Figure 3:
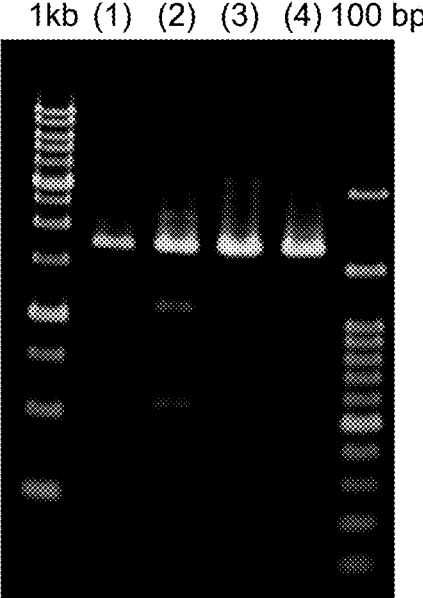
FIG. 3 is an electrophoresis photograph of a result of PCR using a primer set for amplifying AK454412 gene.

The present invention will now be described in detail.
1. Cytochrome P450 Gene

A cytochrome P450 gene according to the present invention (hereinafter sometimes simply referred to as the P450 gene) is a gene having a prescribed amino acid sequence, and encoding a P450 having metabolic activity against a large number of drugs having different acting properties. The P450 gene of the present invention has certain sequence similarity, at the amino acid level, to CYP81A6 of a rice plant, but is different therefrom in encoding a P450 having metabolic activity against a wider range of compounds than CYP81A6.

Generally, a protein classified as P450 has a structure including a transmembrane region on the N-terminal side, and an active region continuously to the transmembrane region. The P450 gene of the present invention may encode a protein comprising an amino acid sequence of a region involved in the metabolic activity excluding a transmembrane sequence, or may encode a protein comprising an amino acid sequence including the transmembrane region and the region involved in the metabolic activity.

In the P450 gene of the present invention, examples of an amino acid sequence of the region involved in the metabolic activity (namely, an amino acid sequence excluding the transmembrane sequence) include amino acid sequences of SEQ ID NOS: 2, 4, 6, and 8.

Here, the amino acid sequence of SEQ ID NO: 2 is an amino acid sequence of a wheat-derived P450 registered in GenBank as accession No. AK454412 excluding a transmembrane sequence, and is encoded by a nucleotide sequence of SEQ ID NO: 1. Besides, the amino acid sequence of SEQ ID NO: 4 is an amino acid sequence of a wheat-derived P450 registered in GenBank as accession No. KJ541960 excluding a transmembrane sequence, and is encoded by a nucleotide sequence of SEQ ID NO: 3. The amino acid sequence of SEQ ID NO: 6 is an amino acid sequence of a barley-derived P450 registered in GenBank as accession No. AK369081 excluding a transmembrane sequence, and is encoded by a nucleotide sequence of SEQ ID NO: 5. The amino acid sequence of SEQ ID NO: 8 is an amino acid sequence of a barley-derived P450 registered in GenBank as accession No. AK375492 excluding a transmembrane sequence, and is encoded by a nucleotide sequence of SEQ ID NO: 7. These P450s consisting of the amino acid sequences set forth in SEQ ID NOS: 2, 4, 6, and 8 (excluding the transmembrane region) are regions involved in the metabolic activity against a large number of drugs having different acting properties.

The amino acid sequence of SEQ ID NO: 4 (KJ541960) has 96% sequence identity, the amino acid sequence of SEQ ID NO: 6 (AK369081) has 80% sequence identity, and the amino acid sequence of SEQ ID NO: 8 (AK375492) has 93% sequence identity to the amino acid sequence of SEQ ID NO: 2 (AK454412). Besides, the nucleotide sequence of SEQ ID NO: 3 (KJ541960) has 96% sequence identity, the nucleotide sequence of SEQ ID NO: 5 (AK369081) has 85% sequence identity, and the nucleotide sequence of SEQ ID NO: 7 (AK375492) has 94% sequence identity to the nucleotide sequence of SEQ ID NO: 1 (AK454412).

The P450 gene of the present invention is not limited to those specified by SEQ ID NOS: 1 to 8, and, for example, may be a gene encoding a protein having an amino acid sequence having 80% or more, preferably 85% or more, more preferably 90% or more, and most preferably 95% or more sequence identity to the amino acid sequence of SEQ ID NO: 2, 4, 6, or 8, and having metabolic activity against a large number of drugs having different acting properties. A value of sequence identity can be calculated by BLASTN or BLASTX program implementing BLAST algorithm (default settings). It is noted that a value of sequence identity is calculated as a ratio, in the total number of all compared amino acid residues, of the number of completely matching amino acid residues calculated in pairwise alignment analysis of a pair of amino acid sequences.

Besides, the P450 gene of the present invention is not limited to those specified by SEQ ID NOS: 1 to 8, and, for example, may be a gene encoding a protein having an amino acid sequence obtained by substituting, deleting, inserting, or adding one or several amino acids in the amino acid sequence of SEQ ID NO: 2, 4, 6, or 8, and having metabolic activity against a large number of drugs having different acting properties. Here, several amino acids refer to, for example, 2 to 50, preferably 2 to 40, more preferably 2 to 30, more preferably 2 to 20, further preferably 2 to 10, and most preferably 2 to 5 amino acids.

Furthermore, the P450 gene of the present invention is not limited to those specified by SEQ ID NOS: 1 to 8, and, for example, may be a gene encoding a protein that hybridizes, under stringent conditions, with all or some of complementary strands of a DNA consisting of the nucleotide sequence of any of SEQ ID NO: 1, 3, 5, and 7, and having metabolic activity against a large number of drugs having different acting properties. The term "stringent conditions" used herein means conditions where what is called a specific hybrid is formed but a non-specific hybrid is not formed, and the conditions can be appropriately determined referring to, for example, Molecular Cloning: A Laboratory Manual (Third Edition). Specifically, stringency can be set in accordance with a temperature and a salt concentration in a solution in Southern hybridization, and a temperature and a salt concentration in a solution in a washing step in Southern hybridization. In more detail, stringent conditions are, for example, a sodium concentration of 25 to 500 mM, and preferably 25 to 300 mM, and a temperature of 42 to 68° C., and preferably 42 to 65° C. More specifically, the conditions are 5×SSC (83 mM NaCl and 83 mM sodium citrate), and a temperature of 42° C.

As described above, it can be confirmed whether or not a gene consisting of a nucleotide sequence different from SEQ ID NOS: 1, 3, 5, and 7, or a gene encoding an amino acid sequence different from SEQ ID NOS: 2, 4, 6, and 8 functions as a cytochrome P450 to encode a protein having a metabolic activity against a prescribed drug by producing a transformed plant using an expression vector obtained by integrating the gene between a Nos promoter derived from *Agrobacterium tumefaciens* and a terminator or the like, and examining whether or not the transformed plant can grow in the presence of the drug. It is noted that the drug can be appropriately selected from a large number of drugs having different acting properties described in detail below.

On the other hand, the P450 gene of the present invention may be a gene encoding a protein comprising an amino acid sequence comprising a transmembrane region and a region involved in metabolic activity for a drug. Examples of the amino acid sequence of the transmembrane region and the region involved in metabolic activity comprise amino acid sequences of SEQ ID NO: 10, 12, 14, and 16.

Here, the amino acid sequence of SEQ ID NO: 10 is an amino acid sequence comprising a transmembrane sequence in a wheat-derived P450 registered in GenBank as accession No. AK454412, and is encoded by a nucleotide sequence of SEQ ID NO: 9. Besides, the amino acid sequence of SEQ ID NO: 12 is an amino acid sequence comprising a transmembrane sequence in a wheat-derived P450 registered in GenBank as accession No. KJ541960, and is encoded by a nucleotide sequence of SEQ ID NO: 11. The amino acid sequence of SEQ ID NO: 14 is an amino acid sequence including a transmembrane sequence in a barley-derived P450 registered in GenBank as accession No. AK369081, and is encoded by a nucleotide sequence of SEQ ID NO: 13. The amino acid sequence of SEQ ID NO: 16 is an amino acid sequence including a transmembrane sequence in a barley-derived P450 registered in GenBank as accession No. AK375492, and is encoded by a nucleotide sequence of SEQ ID NO: 15.

It is noted that the amino acid sequence of SEQ ID NO: 2 described above is a partial sequence of the amino acid sequence of SEQ ID NO: 10. Similarly, the amino acid sequence of SEQ ID NO: 4 described above is a partial sequence of the amino acid sequence of SEQ ID NO: 12. Similarly, the amino acid sequence of SEQ ID NO: 6 described above is a partial sequence of the amino acid sequence of SEQ ID NO: 14. Similarly, the amino acid sequence of SEQ ID NO: 8 described above is a partial sequence of the amino acid sequence of SEQ ID NO: 16.

The amino acid sequence of SEQ ID NO: 12 (KJ541960) has 94% sequence identity, the amino acid sequence of SEQ ID NO: 14 (AK369081) has 79% sequence identity, and the amino acid sequence of SEQ ID NO: 16 (AK375492) has 90% sequence identity to the amino acid sequence of SEQ ID NO: 10 (AK454412). Besides, the nucleotide sequence of SEQ ID NO: 11 (KJ541960) has 95% sequence identity, the nucleotide sequence of SEQ ID NO: 13 (AK369081) has 85% sequence identity, and the nucleotide sequence of SEQ ID NO: 15 (AK375492) has 93% sequence identity to the nucleotide sequence of SEQ ID NO: 9 (AK454412).

The P450 gene of the present invention is not limited to those specified by SEQ ID NOS: 9 to 16, and, for example, may be a gene encoding a protein comprising an amino acid sequence having 80% or more, preferably 85% or more, more preferably 90% or more, and most preferably 95% or more sequence identity to the amino acid sequence of SEQ ID NO: 10, 12, 14, or 16, and having metabolic activity against a large number of drugs having different acting properties. A value of sequence identity can be calculated by BLASTN or BLASTX program implementing BLAST algorithm (default settings). It is noted that a value of sequence identity is calculated as a ratio, in the total number of all compared amino acid residues, of the number of completely matching amino acid residues calculated in pairwise alignment analysis of a pair of amino acid sequences.

Besides, the P450 gene of the present invention is not limited to those specified by SEQ ID NOS: 9 to 16, and, for example, may be a gene encoding a protein having an amino acid sequence obtained by substituting, deleting, inserting, or adding one or several amino acids in the amino acid sequence of SEQ ID NO: 10, 12, 14, or 16, and having metabolic activity against a large number of drugs having different acting properties. Here, several amino acids refer to, for example, 2 to 55, preferably 2 to 45, more preferably 2 to 35, more preferably 2 to 25, further preferably 2 to 15, and most preferably 2 to 5 amino acids.

Furthermore, the P450 gene of the present invention is not limited to those specified by SEQ ID NOS: 9 to 16, and, for example, may be a gene encoding a protein that hybridizes, under stringent conditions, with all or some of complementary strands of a DNA consisting of the nucleotide sequence of any of SEQ ID NO: 9, 11, 13, and 15, and having metabolic activity against a large number of drugs having different acting properties. The term "stringent conditions" used herein means conditions where what is called a specific hybrid is formed but a non-specific hybrid is not formed, and the conditions can be appropriately determined referring to, for example, Molecular Cloning: A Laboratory Manual (Third Edition). Specifically, stringency can be set in accordance with a temperature and a salt concentration in a solution in Southern hybridization, and a temperature and a salt concentration in a solution in a washing step in Southern hybridization. In more detail, stringent conditions are, for example, a sodium concentration of 25 to 500 mM, and preferably 25 to 300 mM, and a temperature of 42 to 68° C., and preferably 42 to 65° C. More specifically, the conditions are 5×SSC (83 mM NaCl and 83 mM sodium citrate), and a temperature of 42° C.

As described above, it can be confirmed whether or not a gene consisting of a nucleotide sequence different from SEQ ID NOS: 9, 11, 13, or 15, or a gene encoding an amino acid sequence different from SEQ ID NOS: 10, 12, 14, or 16 functions as a cytochrome P450 to encode a protein having metabolic activity against a prescribed drug by producing a transformed plant using an expression vector obtained by integrating the gene between a Nos promoter derived from *Agrobacterium tumefaciens* and a terminator or the like, and examining whether or not the transformed plant can grow in the presence of the drug. It is noted that the drug can be appropriately selected from a large number of drugs having different acting properties described in detail below.

The P450 of the present invention has metabolic activity against a large number of drugs having different acting properties as compared with conventional P450s, such as CYP81A6. Examples of the drugs against which the P450 of the present invention has metabolic activity include an acetolactate synthase inhibitor classified as code 2 of HRAC classifications, a microtubule assembly inhibitor classified as code 3 of HRAC classifications, a photosystem II inhibitor classified as code 6 of HRAC classifications, a carotenoid biosynthesis inhibitor in phytoene desaturase (PDS) classified as code 12 of HRAC classifications, a protoporphyrinogen oxidase inhibitor classified as code 14 of HRAC classifications, a dihydropteroate synthase inhibitor classified as code 18 of HRAC classifications, and a 4-hydroxyphenylpyruvate dioxygenase inhibitor classified as code 27 of HRAC classifications.

The P450 of the present invention is different from the conventionally known other P450s in having metabolic activity against a protoporphyrinogen oxidase inhibitor classified as code 14 of HRAC classifications, a carotenoid biosynthesis inhibitor in phytoene desaturase (PDS) classified as code 12 of HRAC classifications, a 4-hydroxyphenylpyruvate dioxygenase inhibitor classified as code 27 of HRAC classifications, a dihydropteroate synthase inhibitor classified as code 18 of HRAC classifications, and a microtubule assembly inhibitor classified as code 3 of HRAC classifications among those described above.

Here, an acetolactate synthase inhibitor means a compound exhibiting herbicidal activity by inhibiting acetolactate synthase. Examples of the acetolactate synthase inhibitor include sulfonylurea compounds such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfron, flupyrsulfron, foramsulfuron, halosulfuron-methyl, imazosulfuron, iodosulfuron, mesosulfuron, metsulfuron-methyl, nicosulfuron, oxasulfuron, primisulfuron, prosulfuron, pyrazosulfuronethyl, rimsulfuron, sulfometuron-methyl, sulfosulfuron, thifensulfuron-methyl, triasulfuron, tribenuron-methyl, trifloxysulfuron, triflusulfuron-methyl, and tritosulfuron; imidazolinone compounds such as imazapic, imazamethabenzmethyl, imazamox, imazapyr, imazaquin, and imazethapyr; triazolopyrimidine compounds such as cloransulam-methyl, diclosulam, florasulam, flumetsulam, metosulam, and penoxsulam; pyrimidinyl (thio)benzoate compounds such as bispyribac-sodium salt, pyribenzoxim, pyriftalid, pyrithiobac-sodium salt, and pyriminobac-methyl; sulfonylaminocarbonyltriazolinone compounds such as flucarbazonesodium salt, and propoxycarbazone-sodium salt; and sulphonanilide compounds such as pyrimisulfan and triafamone.

A photosystem II inhibitor classified as code 6 of HRAC classifications means a compound exhibiting herbicidal activity by inhibiting photosystem II involved in photosynthesis. Examples of the photosystem II inhibitor classified as code 6 of HRAC classifications include nitrile compounds such as bromophenoxim, bromoxynil, and ioxynil; benzothiadiazinone compounds such as bentazone; and phenylpyridazine compounds such as pyridate and pyridafol.

A protoporphyrinogen oxidase inhibitor means a compound exhibiting herbicidal activity by inhibiting protoporphyrinogen oxidase. Examples of the protoporphyrinogen oxidase inhibitor include diphenyl ether compounds such as acifluorfen, bifenox, chlomethoxynil (chlomethoxyfen), fluoroglycofen-ethyl, fomesafen, halosafen, lactofen, and oxyfluorfen; phenyl pyrazole compounds such as fluazolate and pyraflufen-ethyl; N-phenylphthalimide compounds such as cinidon-ethyl, flumioxazin, and flumiclorac-pentyl; thiadiazole compounds such as fluthiacet-methyl and thidiazimin; oxadiazole compounds such as oxadiazon and oxadiargyl; triazolinone compounds such as azafenidin, carfentrazone-ethyl, and sulfentrazone; oxazolidinedione compounds such as pentoxazone; pyrimidinedione compounds such as benzphendizone and butafenacil; phenylpyrazole compounds such as pyraflufen-ethyl and fluazolate; and pyraclonil, profluazole, and flufenpyr-ethyl.

A carotenoid biosynthesis inhibitor in phytoene desaturase (PDS) means a compound exhibiting herbicidal activity by inhibiting phytoene desaturase. Examples of the carotenoid biosynthesis inhibitor include pyridazinone compounds such as norflurazon; pyridinecarboxamide compounds such as diflufenican and picolinafen; and beflubutamid, fluridone, flurochloridone, and flurtamone.

A 4-hydroxyphenylpyruvate dioxygenase inhibitor means a compound exhibiting herbicidal activity by inhibiting 4-hydroxyphenylpyruvate dioxygenase. Examples of the 4-hydroxyphenylpyruvate dioxygenase inhibitor include triketone compounds such as fenquinotrione, mesotrione, and sulcotrione; isoxazole compounds such as isoxachlortole and isoxaflutole; pyrazole compounds such as benzofenap, pyrazolate (pyrazolynate), and pyrazoxyfen; and benzobicyclon.

A dihydropteroate synthase inhibitor means a compound exhibiting herbicidal activity by inhibiting dihydropteroate synthase. Examples of the dihydropteroate synthase include carbamate compounds such as asulam.

A microtubule assembly inhibitor is a compound exhibiting herbicidal activity by acting on a globular protein, tubulin to inhibit polymerization of microtubule. Examples of the microtubule assembly inhibitor include dinitroaniline compounds such as bethrodine (benfluralin), butralin, dinitramine, ethalfluralin, oryzalin, pendimethalin, and trifluralin; phosphoramidate compounds such as amiprophosmethyl and butamifos; pyridine compounds such as dithiopyr and thiazopyr; benzamide compounds such as propyzamide and tebutam; and benzoic acid compounds such as TCTP (chlorthal-dimethyl).

The P450 of the present invention has excellent metabolic activity particularly against pyrimisulfan, penoxsulam, bensulfuron-methyl, metsulfuron-methyl, imazaquin, nicosulfuron, sulfometuron-methyl, bentazone, oxadiargyl, sulfentrazone, pyraflufen-ethyl, fomesafen, diflufenican, picolinafen, fluridone, norflurazon, pyrazolate, benzofenap, fenquinotrione, asulam, and pendimethalin among the exemplarily described specific compounds.

2. Expression Vector An expression vector of the present invention can be obtained by linking (inserting) the cytochrome P450 gene of the present invention to (into) an appropriate vector. The vector for inserting the cytochrome P450 gene of the present invention thereinto is not especially limited as long as it is replicable in a host, and examples include a plasmid, a shuttle vector, and a helper plasmid.

Examples of a plasmid DNA include plasmids derived from *E. coli* (such as pBR322, pBR325, pUC118, pUC119, pUC18, pCU19, and pBluescript), plasmids derived from *Bacillus subtilis* (such as pUB110 and pTP5), and plasmids derived from yeast (such as YEp13 and YCp50), and examples of a phage DNA include λ phages (Charon 4A, Charon 21A, EMBL3, EMBL4, λgt10, λgt11, and λZAP). Alternatively, an animal virus such as a retrovirus or vaccinia virus, or an insect virus vector such as baculovirus can be used.

For inserting the cytochrome P450 gene of the present invention into a vector, a method in which a DNA fragment comprising the cytochrome P450 gene is first purified, the purified DNA fragment is cleaved with an appropriate restriction enzyme, and the resultant is inserted into a restriction enzyme site or a multicloning site of an appropriate vector DNA to be linked to the vector, or the like is employed.

In the present invention, to express an arbitrary gene, the arbitrary gene can be further inserted into the expression vector. A method for inserting the arbitrary gene is the same as the method for inserting the cytochrome P450 gene of the present invention into a vector.

The cytochrome P450 gene of the present invention can be examined for the herbicide resistance after being linked between a Nos promoter derived from *Agrobacterium tume-faciens* and a terminator or the like to be introduced into a plant. Examples of the promoter include, in addition to a Nos promoter, cauliflower mosaic virus 35S promoter (CaMV35S), various actin gene promoters, various ubiquitin gene promoters, a nopaline synthase gene promoter, a tobacco PR1a gene promoter, a tomato ribulose 1,5-diphosphate carboxylase/oxidase small subunit gene promoter, a napin gene promoter, and an oleosin gene promoter. Among these, cauliflower mosaic virus 35S promoter, an actin gene promoter, or a ubiquitin gene promoter can be more preferably used.

In this manner, various vectors can be used in the present invention. Besides, a target arbitrary gene can be connected to the cytochrome P450 gene of the present invention in the sense or antisense direction, so that the resultant can be inserted into a vector designated as a binary vector, such as pBI101 (Clontech).

3. Production of Transformant

A transformant of the present invention can be obtained, for example, by introducing the above-described expression vector of the present invention into a host. Here, the host is not especially limited as long as it can express the cytochrome P450 gene of the present invention, and is preferably a plant. When the expression vector of the present invention is introduced into a host, the resistance to a large number of drugs having different acting properties described above can be obtained through the expression of the cytochrome P450 gene of the present invention. Therefore, it can be confirmed whether or not the above-described expression vector of the present invention has been able to be introduced into the host by evaluation using, as an index, the resistance to the drug. In other words, the cytochrome P450 gene of the present invention can be used also as a selection marker in introducing an additional gene.

The plant to be transformed in the present invention means any of an entire plant body, a plant organ (such as a leaf, a petal, a stem, a root, or a seed), a plant tissue (such as an epidermis, a phloem, a parenchyma, a xylem, or a vascular bundle), and a cultured plant cell. Examples of the plant to be used in the transformation include, but are not limited to, plants belonging to the *Arabidopsis* family, the Poaceae family, the Solanaceae family, and the Fabaceae family (see the following):

*Arabidopsis* family: *Arabidopsis thaliana*
   Solanaceae family: tobacco (*Nicotiana tabacum*)
   Poaceae family: corn (*Zea mays*) and rice (*Oryza sativa*)
   Fabaceae family: soybean (*Glycine max*)

The above-described expression vector can be introduced into a plant by a usual transformation method, such as an electroporation method, an *Agrobacterium* method, a particle gun method, or a PEG method.

For example, when an electroporation method is employed, a treatment is performed with an electroporation device equipped with a pulse controller under conditions of a voltage of 500 to 1,600 V, 25 to 1,000 μF, and 20 to 30 msec to introduce the gene into a host.

Alternatively, when a particle gun method is employed, a plant body, plant organ, or plant tissue itself may be directly used, may be used after preparing a section, or may be used with a protoplast prepared. A sample thus prepared can be treated with a gene transfer device (such as PDS-1000/He available from Bio-Rad Laboratories, Inc.). Treatment conditions are varied depending on a plant or a sample, and the treatment is usually performed at a pressure of about 1,000 to 1,800 psi at a distance of about 5 to 6 cm.

Besides, the cytochrome P450 gene of the present invention can be introduced into a plant body by utilizing a plant virus as a vector. An example of the usable plant virus includes cauliflower mosaic virus. Specifically, a recombinant is first prepared by inserting a virus genome into an *E. coli*-derived vector or the like, and then, the cytochrome P450 gene of the present invention is inserted into the virus genome. The virus genome thus modified is cleaved from the recombinant with a restriction enzyme, and inoculated in a plant host, and thus, the cytochrome P450 gene of the present invention can be introduced into the plant host.

In a method utilizing *Agrobacterium* Ti plasmid, the cytochrome P450 gene of the present invention is introduced into a plant host by utilizing the following property: in a plant infected with a bacterium belonging to the genus *Agrobacterium*, part of its plasmid DNA is transferred into the plant genome. Among bacteria belonging to the genus *Agrobacterium*, *Agrobacterium tumefaciens* forms a tumor designated as crown gall through infection of a plant, and *Agrobacterium rhizogenes* generates a capillary root through infection of a plant. This is because a region designated as T-DNA region (transferred DNA) on a plasmid present in various bacteria designated as a Ti plasmid or Ri plasmid is transferred into a plant through infection to be integrated into a genome of the plant.

If a DNA desired to be integrated into a plant genome has been inserted into a T-DNA region on a Ti or Ri plasmid, the target DNA can be integrated into the plant genome when a bacterium belonging to the genus *Agrobacterium* infects the plant host.

A tumor tissue, a shoot, a capillary root, or the like resulting from the transformation can be directly used in cell culture, tissue culture, or organ culture, and can be regenerated into a plant body by a conventionally known plant tissue culture method with administration of an appropriate concentration of a plant hormone (such as auxin, cytokinin, gibberellin, abscisic acid, ethylene, or brassinolide) or the like.

A transformant obtained by introducing the cytochrome P450 gene of the present invention can be used for screening a compound usable as a novel herbicide for plants. Specifically, a candidate substance is contacted with a transformant obtained by introducing the cytochrome P450 gene of the present invention. Besides, the same candidate substance is contacted also with a cell into which the cytochrome P450 gene of the present invention has not been introduced (preferably, a host cell from which the transformant is obtained). Then, a compound with which the transformant grows but the cell not having the cytochrome P450 gene of the present invention introduced dies is selected. It can be concluded that the selected compound is a compound usable as a herbicide detoxified/metabolized by the cytochrome P450 gene of the present invention.

The screened compound is not toxic to a plant having the cytochrome P450 gene of the present invention, but is toxic to a plant not having the cytochrome P450 gene. Therefore, the screened compound can be used as a herbicide in selectively growing a plant having the cytochrome P450 gene of the present invention.

A transformant can be obtained by introducing the expression vector of the present invention not only into the plant host described above but also into bacteria belonging to the genus *Escherichia* such as *E. coli*, the genus *Bacillus* such as *Bacillus subtilis*, or the genus *Pseudomonas* such as *Pseudomonas putida*, yeasts such as *Saccharomyces cerevisiae* and *Schizosaccharomyces pombe*, animal cells such as COS cell and CHO cell, or insect cells such as Sf9. When a bacterium such as *E. coli* or yeast is used as a host, the expression vector of the present invention is preferably autonomously replicable in the bacterium, and at the same time, constructed to include the cytochrome P450 gene of the present invention, a ribosome binding sequence, a target gene, and a transcription termination sequence. Besides, a gene controlling the cytochrome P450 gene of the present invention may be included.

A method for introducing a recombinant vector into a bacterium is not especially limited as long as it is a method for introducing a DNA into a bacterium. Examples include a method using a calcium ion, and an electroporation method.

When yeast is used as the host, for example, *Saccharomyces cerevisiae* and *Schizosaccharomyces pombe* are used. A method for introducing a recombinant vector into yeast is not especially limited as long as it is a method for introducing a DNA into yeast, and examples include an electroporation method, a spheroplast method, and a lithium acetate method.

When an animal cell is used as the host, monkey cell COS-7, Vero, Chinese hamster ovarian cell (CHO cell), mouse L cell and the like are used. Examples of a method for introducing a recombinant vector into an animal cell include an electroporation method, a calcium phosphate method, and a lipofection method.

When an insect cell is used as the host, Sf9 cell and the like are used. Examples of a method for introducing a recombinant vector into an insect cell include a calcium phosphate method, a lipofection method, and an electroporation method.

It can be confirmed whether or not the gene has been integrated into the host by a PCR method, Southern hybridization method, Northern hybridization method, or the like. For example, a DNA is prepared from the transformant, and a DNA specific primer is designed to perform PCR. The PCR is performed under the same conditions as those employed for preparing the plasmid. Thereafter, an amplification product is subjected to agarose gel electrophoresis, polyacrylamide gel electrophoresis, capillary electrophoresis, or the like, the resultant is dyed with ethidium bromide, SYBR Green solution, or the like to detect the amplification product as one band, and thus, the transformation is confirmed. Alternatively, the amplification product can be detected by performing PCR using a primer precedently labeled with a fluorescent dye or the like. Further alternatively, a method in which the amplification product is bound to a solid phase such as a microplate to confirm the amplification product with a fluorescent or enzymatic reaction, or the like may be employed.

4. Production of Plant

In the present invention, a transformed plant body can be regenerated from the transformed plant cell or the like. As a regeneration method, a method in which transformed cells in a callus state are each transferred to media varied in the type and the concentration of hormones to be cultured therein, and adventitious embryos are thus formed to obtain a complete plant body is employed. Examples of the medium used include LS medium and MS medium.

A "method for producing a plant body" of the present invention comprises steps of obtaining a transformed plant cell by introducing, into a host cell, a plant expression vector comprising the cytochrome P450 gene of the present invention inserted thereinto, regenerating a transformed plant body from the transformed plant cell, obtaining a plant seed from the transformed plant obtained, and producing a plant body from the plant seed.

In order to obtain a plant seed from the transformed plant body, for example, the transformed plant body is collected from a rooting medium, transplanted in a pot holding soil containing water, and grown at a constant temperature to grow a flower, and ultimately to produce a seed. Besides, in order to produce a plant body from a seed, for example, when a seed grown on a transformed plant matures, the seed is isolated to be seeded in soil containing water, and grown at a constant temperature and constant brightness to produce a plant body. A plant thus produced expresses the cytochrome P450 gene of the present invention, and hence is resistant to the large number of drugs having different acting properties described above. Here, the term "being resistant to drugs" has the same meaning as being resistant to the drugs with a statistically significant difference as compared with before introducing the cytochrome P450 gene of the present invention. Resistance to a drug can be determined based on a mortality rate of a plant body, a growth inhibition rate of a stem and leaf portion, a root portion and the like, or the like obtained through contact with the drug at a prescribed concentration.

5. Method for Controlling Noxious Weed

A transgenic plant obtained by introducing the P450 gene of the present invention into a plant is resistant to a large number of drugs having different acting properties as described above. Therefore, when the transgenic plant obtained by introducing the P450 gene of the present invention into a plant is cultivated in a field, a drug selected from the large number of drugs having different acting properties described above can be used as a herbicide to wither weed excluding the transgenic plant.

As described so far, a transgenic plant obtained by introducing the P450 gene of the present invention into a plant can be cultivated with weed easily removed because a drug for removing weed in a field can be selected from a wide range.

EXAMPLES

Now, the present invention will be described in more detail with reference to examples, and it is noted that the technical scope of the present invention is not limited to the following examples.

Example 1

1. Search for Novel Wheat P450 Metabolizing Herbicide
1) Search and Isolation of Wheat P450 Gene Metabolizing Fenquinotrione It is currently known that CYP81A6 of a rice plant has metabolic activity against three drugs having different mechanisms of action, that is, an ALS inhibitor, a photosystem II inhibitor, and an HPPD inhibitor in HRAC classifications. Among these, fenquinotrione, that is, an HPPD inhibitor for paddy rice, is metabolically degraded through demethylation with CYP81A6, and hence has been revealed to have high safety for a rice plant. This drug also has high safety for wheat, and a main metabolite of this drug in wheat is a demethylated product as in a rice plant, and hence, it was suggested that a P450 having a similar function to CYP81A6 is present in wheat.

Figures 1, 7:
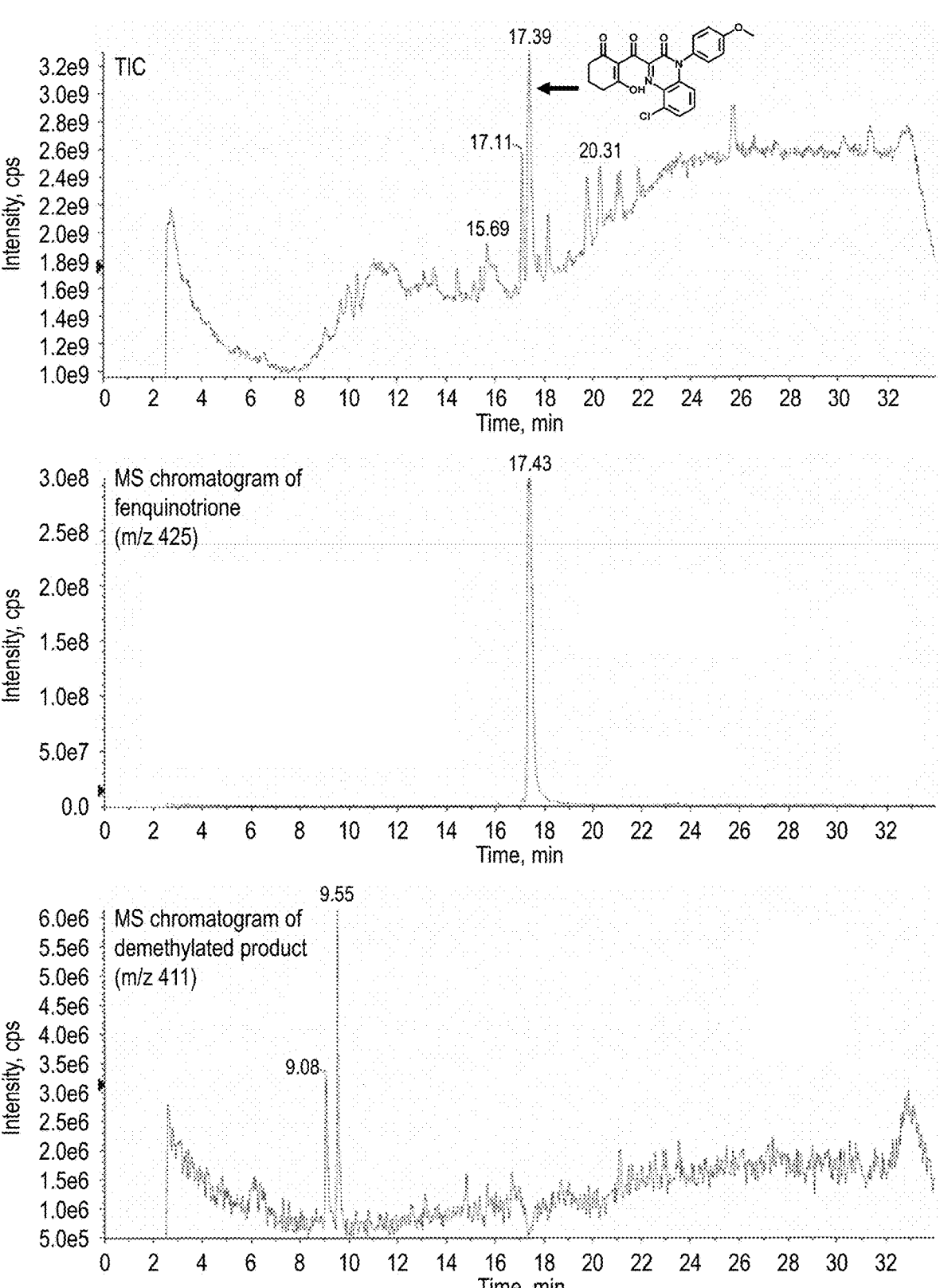
Figures 2, 7:
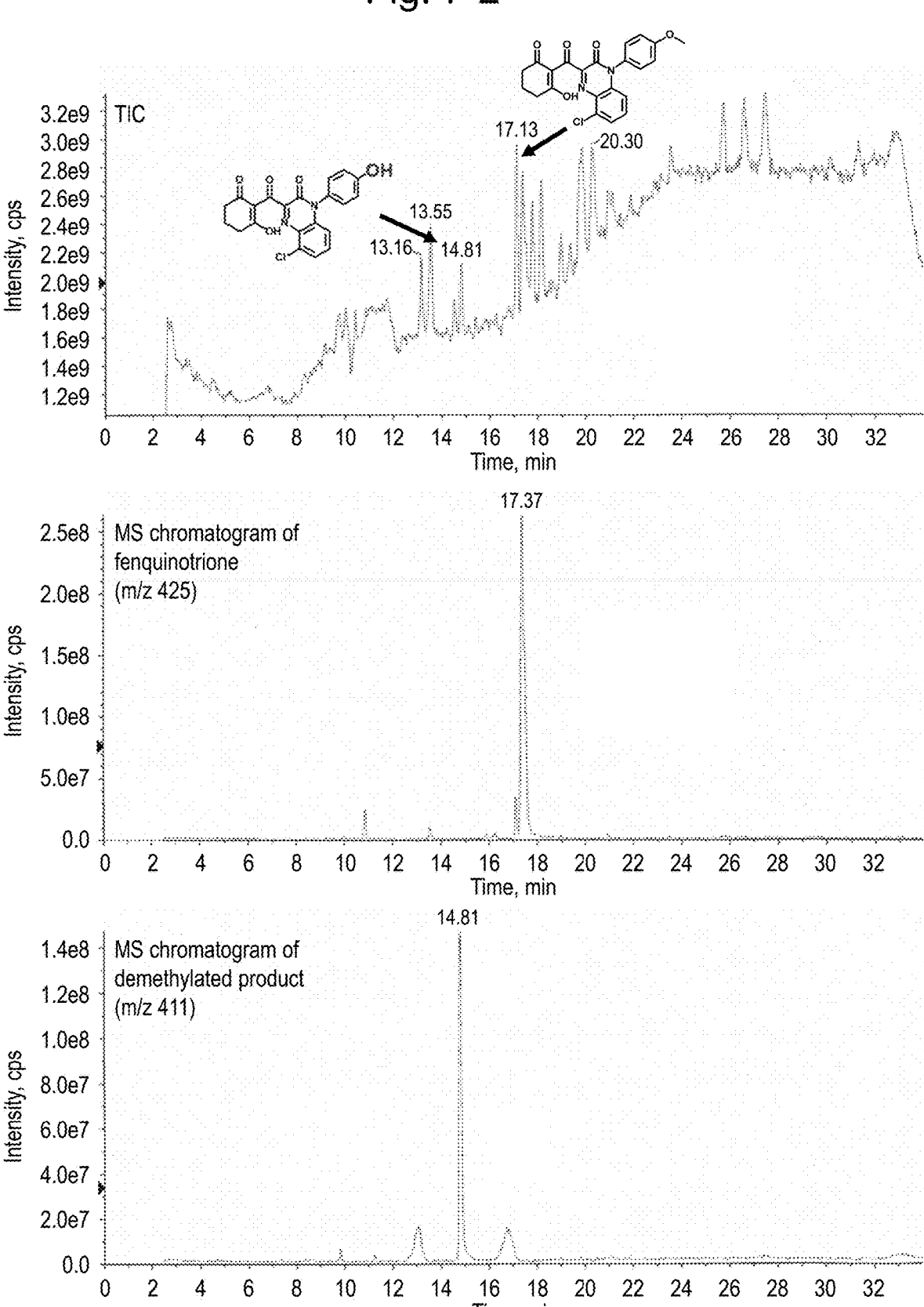

Since CYP71C6v1 known as a P450 for metabolizing a herbicide in wheat was, however, not highly homologous to CYP81A6, it was presumed that metabolically degrading activity against fenquinotrione is caused by an unknown P450 different from CYP71C6v1. Therefore, genes similar to CYP81A6 in wheat were searched for. With the ORF sequence of CYP81A6 used as a query, blastn search was performed on GenBank. As a result, two barley-derived P450s (accession No. AK375492 (80%) and AK369081 (80%)) and one wheat-derived P450 (accession No. AK454412 (clone ID: tplb0005j01) (81%)) were hit. Besides, with the ORF sequence of AK454412 used as a query, blastn search was performed on GenBank, and as a result, another wheat-derived P450 of Accession No. KJ541960 (80%) was hit (it is noted that each parenthesized numeral indicates identity to CDS sequence of CY81A6 gene). FIG. 1 illustrates multiple alignment of CYP81A6, AK375492, and AK369081, and FIG. 2 illustrates multiple alignment of CYP81A6, AK454412, and KJ541960.

In order to verify fenquinotrione metabolic activity in vitro of AK454412 gene, that is, the wheat-derived putative P450 gene hit, this gene was cloned, and it was verified whether or not it is present in various breeds of wheat. The breeds of wheat tested were Norin No. 61 produced in Japan, Bolak produced in Australia, Apache produced in Europe, and Tamarai as durum wheat. A full length of the CDS region sandwiching the UTR region was amplified via PCR with a cDNA of each of these four breeds used as a template and using a primer set of AK454412 5'-UTR (Fd) and AK454412 3'-UTR (Rv). As a result, a band (1,791 bp) was confirmed in a predicted position in all of the breeds, and hence it was suggested that this gene may be present regardless of breed (FIG. 3). Subsequently, to clone this gene, PCR was performed again with a DNA fragment amplified with a genome of the Apache wheat used as a template, and using a primer set of AK454412 IF (Fd) and AK454412 IF (Rv), and thus, the CDS sequence of the AK454412 gene was amplified. This DNA fragment and pET-22b(+) vector, having been treated with restriction enzymes NdeI and XhoI, were linked to each other with In-Fusion HD Cloning Kit (TaKaRa) to produce pET-22b-AK454412. The thus obtained construct was subjected to sequence analysis, resulting in finding that, as compared with the sequence described in GenBank, the 453rd C was mutated to T, and the 1,137th T was mutated to C, both of which were mutations not involving amino acid mutation.

The sequences of the primers used were as follows:

```
AK454412 5'-UTR (Fd):
                                    (SEQ ID No. 17)
5'-CAACCTGAGACCTCAAGTGTCAC-3'

AK454412 3'-UTR (Rv):
                                    (SEQ ID No. 18)
5'-GTACTACCTGGATCCACGAGC-3'

AK454412 IF (Fd):
                                    (SEQ ID No. 19)
5'-AAGGAGATATACATATGGATAAGGCGTACATTGCC-3'

AK454412 IF (Rv):
                                    (SEQ ID No. 20)
5'-GTGGTGGTGCTCGAGTCAGAGGCTCTGAAGCACGT-3'
```

2) Search and Isolation of Wheat-Derived P450 Reductase

In general, for monooxygenase reaction of P450, two-electron reduction, and accompanying proton transfer are indispensable. An enzyme catalyzing this reaction is P450 reductase (CPR), and wheat-derived CPR is necessary for AK454412, presumed as one of wheat P450s, to function. Therefore, it was decided to search and clone wheat-derived CPR. First, with Os09g0558900, that is, rice P450 reductase (CPR), used as a query, Blast search was performed on GenBank. As a result, two genes of accession No. AK333516 (derived from Chinese Spring, SEQ ID NO: 21)

and AJ303373 (derived from Darius, SEQ ID NO: 22) were found, and since the CDS sequences of these genes were substantially the same (with the 1,665th A replaced with G (amino acid: I555V) when seen in AJ303373), these genes were regarded as the same gene, and hence, it was here decided to perform cloning from AJ303373 (hereinafter referred to as TaCPR).

First, in the same manner as in the search for a wheat P450, with a cDNA of each of the four breeds, Norin No. 61, Bolak, Apache, and Tamarai, used as a template, a full length of the CDS region sandwiching the UTR region was amplified via PCR using a primer set of CPR_AJ303373_UTR (Fd) and CPR UTR (Rv). As a result, a band (2,397 bp) in a predicted position was confirmed in all of the breeds tested here, and hence it was suggested that this gene may be present regardless of breed. Subsequently, to clone this gene, PCR was performed again with a DNA fragment amplified with a genome of the Apache wheat used as a template, and using a primer set of TaCPR (AJ303373) IF (Fd) and TaCPR IF (Rv), and thus, the CDS sequence of the AJ303373 gene was amplified. This DNA fragment and pACYC Duet-2 vector (Novagen), having been treated with restriction enzymes NdeI/XhoI, were linked to each other with In-Fusion HD Cloning Kit (TaKaRa) to produce pACYC-TaCPR. The thus obtained construct was subjected to sequence analysis, resulting in finding that the sequence of the cloned AJ303373 gene completely matched the sequence described in database.

The sequences of the primers used were as follows:

```
CP_RAJ303373_UTR (Fd):
                                    (SEQ ID No. 23)
5'-CACGCGTCCGATCGAACCAAC-3'

CPR_UTR (Rv):
                                    (SEQ ID No. 24)
5'-CGATGAATCGTCATCCTCTGTTCCAC-3'

TaCPR(AJ303373) IF (Fd):
                                    (SEQ ID No. 25)
5'-AAGGAGATATACATATGGACTCCGCCGCCGCGGGG-3'

TaCPR IF (Rv):
                                    (SEQ ID No. 26)
5'-CTTTACCAGACTCGATTACCAGACGTCTCTCAGGT-3'
```

3) Preparation of AK454412 Construct for Expressing *E. coli*

Figure 4:
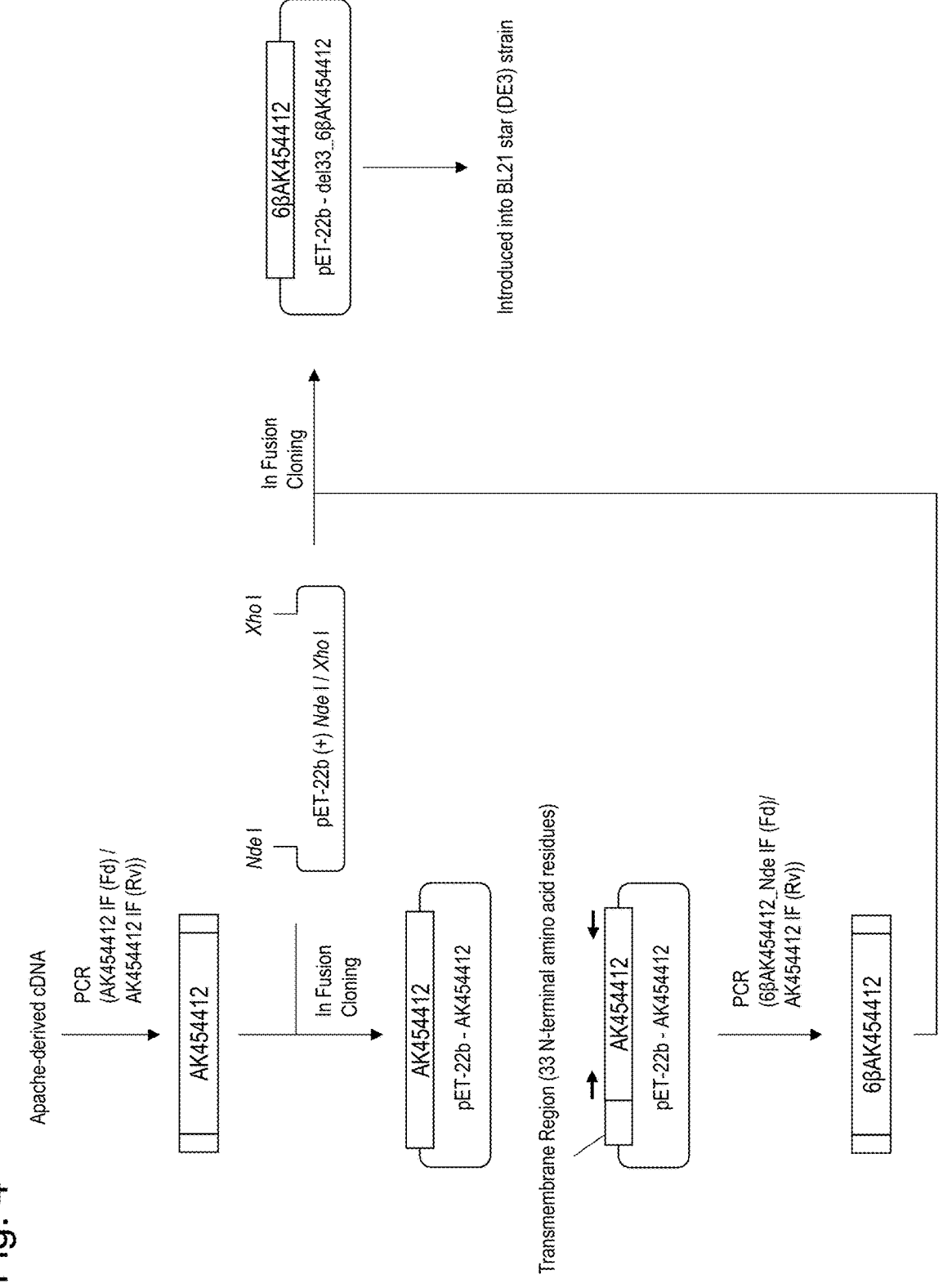
FIG. 4 is a characteristic diagram illustrating production process of *E. coli* expression construct of AK454412 gene.

A P450 of a eukaryote usually has a transmembrane region (membrane anchoring region) at the N-terminal, and it is known that expression possibility is increased in expression of *E. coli* by removing this region, and adding, to the N-terminal, Barnes sequence (MALLLAV) or rabbit 6β-hydroxylase-derived sequence (6β sequence: MAKKTSS). Therefore, with the above-described pET-22b-AK454412 plasmid used as a template, PCR was performed using a primer set of 6 AK454412_Nde IF (Fd) and AK454412 IF (Rv) to obtain a DNA fragment in which 15 bases complementary to the vector side terminal were further added to both terminals of a nucleotide sequence encoding a sequence obtained by deleting 33 N-terminal amino acid residues of AK454412, and adding 7 amino acid residues (6β sequence: MAKKTSS). This DNA fragment and pET-22b(+), having been treated with NdeI/XhoI, were linked to each other with In-Fusion HD Cloning Kit (Clontech) to construct pET-22b-del33_6β AK454412. The prepared construct was introduced into *E. coli* BL21 star (DE3) strain (FIG. 4).

The sequences of the primers used were as follows:

```
6βAK454412_NdeIF (Fd):
                                    (SEQ ID No. 27)
5'-AAGGAGATATACATATGGCTAAGAAGACTTCTTCT-3'

AK454412 IF (Rv):
                                    (SEQ ID No. 28)
5'-GTGGTGGTGCTCGAGTCAGAGGCTCTGAAGCACGT-3'
```

4) Preparation of AJ303373 Construct for Expressing *E. coli*

Figure 5:
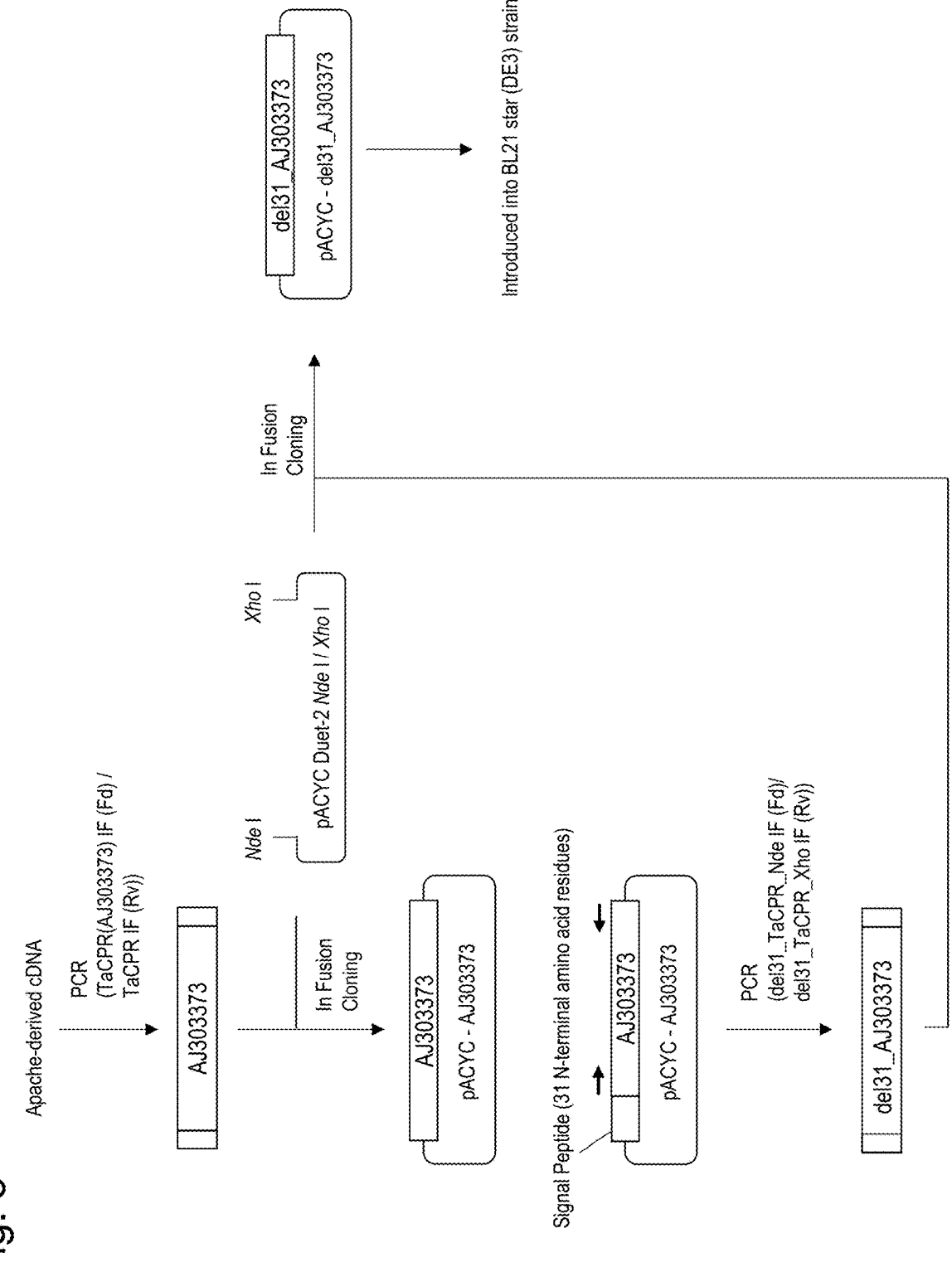
FIG. 5 is a characteristic diagram illustrating production process of *E. coli* expression construct of AJ303373 gene.

CPR has chloroplast transfer signal peptide at the N-terminal, and heterologous expression can be caused in *E. coli* by removing this sequence. Therefore, with the above-described pACYC-TaCPR plasmid used as a template, PCR was performed using a primer set of del31_TaCPR_Nde IF (Fd) and del31_TaCPR_Xho IF (Rv) to obtain a DNA fragment in which 15 bases complementary to the vector side terminal were further added to both terminals of a nucleotide sequence encoding a sequence obtained by deleting 31 N-terminal amino acid residues of AJ303374. This DNA fragment and pACYC Duet-2, having been treated with NdeI/XhoI, were linked to each other with In-Fusion Cloning HD (Clontech) to construct pACYC-del31_TaCPR. The prepared construct was introduced into *E. coli* BL21 star (DE3) strain (FIG. 5).

The sequences of the primers used were as follows:

```
del31_TaCPR_Nde IF (Fd):
                                    (SEQ ID No. 29)
5'-AAGGAGATATACATATGGACCAGAACCGCCGCCTG-3' del31_TaCPR_Xho IF (Rv):
                                    (SEQ ID No. 30)
5'-TTTACCAGACTCGAGTTACCAGACGTCTCTCAGGT-3'
```

Figure 6:
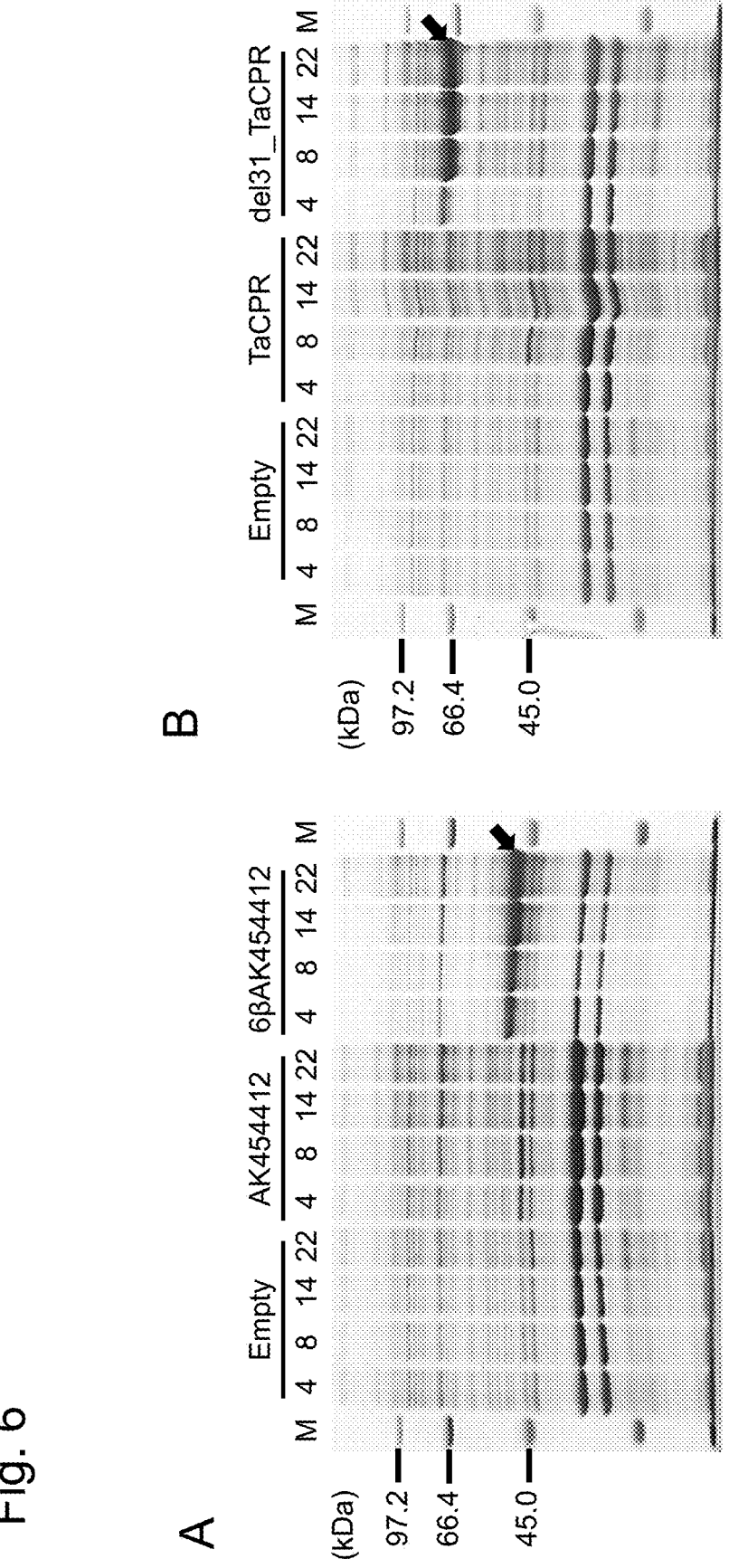
FIG. 6 is a SDS-PAGE photograph illustrating expression of AK454412 protein and TaCPR protein.

5) Protein Co-Expression of AK454412 and AJ303373 in *E. coli* Expression System A single colony of the recombinant *E. coli* into which each of the above-described two expression constructs had been introduced was inoculated in 3 ml of LB liquid medium, followed by culturing at 37° C. and 200 rpm overnight. 2.5 mL of the resultant culture fluid was added to 250 mL of TB medium (containing 100 ppm carbenicillin and 50 ppm chloramphenicol) held in a 1 L Erlenmeyer flask, followed by culturing at 37° C. and 200 rpm until an $OD_{600}$ of about 0.5 to 0.6 was obtained. After the resultant flask was cooled with ice, IPTG and aminolaevulinic acid were added thereto to final concentrations of 1 mM and 0.5 mM, respectively, followed by culturing at 20° C. and 110 rpm. 22 hours after the IPTG induction, the resultant culture fluid was centrifuged (4° C., 15,000 rpm, 1 min). A bacterial cell in the obtained 500 mL of culture fluid was suspended in 35 mL of P450 Buffer [50 mM potassium phosphate buffer (pH 7.3), 20% glycerol, 1 mM EDTA, and 1 mM DTT] to be sonicated, followed by centrifugation at 4° C. and at 6,000×g for 10 minutes. The supernatant was centrifuged at 4° C. and at 100,000×g for 1 hour, and a solution obtained by adding P450 Buffer by 1 mL to the obtained precipitate and homogenizing the resultant with a Teflon homogenizer was used as a co-expression crude enzyme solution for AK454412 and TaCPR. This crude enzyme solution was used to examine protein expression by SDS-PAGE (CBB dyeing), and bands of AK454412 and TaCPR were confirmed in the vicinity of 54 kDa and 75 kDa, respectively, and thus, these enzymes were successfully expressed. Results of the SDS-PAGE are illustrated in FIG. 6. FIG. 6(A) illustrates a result (with an arrow) of the expression of AK454412 (6β AK454412) in which 33 N-terminal amino acid residues were removed and the 6β sequence was added, and FIG. 6(B) illustrates a result (with an arrow) of the expression of TaCPR (del31_TaCPR) in which 31 N-terminal amino acid residues were removed.

6) In Vitro Metabolism Test Using Co-expression Crude Enzyme of AK454412 and TaCPR It was verified by in vitro metabolism test whether or not a novel wheat-derived P450 of AK454412 is involved in herbicide metabolism. As a compound having high safety against wheat, fenquinotrione was used. A reaction solution had a composition of 50 mM potassium phosphate buffer (pH 7.3), 1 mg of the crude enzyme, 1 mM β-NADPH, and 10 μM fenquinotrione, and the reaction was performed at 30° C. for 1 hour, and then stopped by vortex. A solution after completing the enzymatic reaction was centrifuged at 15,000 rpm for 1 minute, and the obtained supernatant was filtered through a 0.45 μm filter and then tested by LC/MS. LC/MS conditions were as follows:

<HPLC Conditions> apparatus: Prominence UFLC (Shimadzu Corporation)

detector: UV 254 nm temperature: 35° C.

flow rate: 0.3 mL/min column: TSKgel ODS-80 Ts (0.5 μm, 2.0 mm×150 mm, TOSOH)

mobile phase: acetonitrile (containing 0.5% acetic acid)/ water (containing 0.5% acetic acid)=20/80 (5 min hold)→(15 min)→80/20 (10 min hold)→(4 min)→20/ 80 (6 min hold)

<MS Conditions> apparatus: Triple Quad™ 4500 (SCIEX)

interface: ESI scan mode: Q1 Scan, Product ion scan m/z 140-700 polarity: positive ion spray voltage: 4,500 source temperature: 400 curtain gas: 40 ion source gas 1: 50 ion source gas 2: 50 declustering potential: 20 entrance potential: 4.5

Results of the LC/MS analysis are illustrated in FIGS. 7-1 and 7-2. FIG. 7-1 illustrates a result of the LC/MS analysis performed on a negative control plot (empty vector expression crude enzyme reaction plot). FIG. 7-2 illustrates a result of LC/MS analysis performed on an AK454412-TaCPR co-expression crude enzyme reaction plot. As illustrated in FIG. 7-2, when the AK454412 and TaCPR co-expression crude enzyme solution was used, peaks were detected in the vicinity of RT of 17.4 and 14.8, and molecular weight of these peaks were m/z 425, and m/z 411, respectively. As a result of comparison with a preparation, it was revealed that the peak of m/z 425 corresponds to the parent compound of fenquinotrione, and the peak of m/z 411 corresponds to a demethylated product of fenquinotrione. This demethylated product is a main metabolite of fenquinotrione in a wheat body, and it has been known that this metabolite does not exhibit herbicidal activity. It was revealed, based on these, that AK454412 is a P450 that metabolically degrades fenquinotrione to the demethylated product to impart wheat selectivity.

[Example 2] Functional Analysis of Novel
Wheat-Derived P450, AK454412

1) Creation of *Arabidopsis thaliana* Having AK454412
Forced Expression

In order to examine the influence of the demethylation reaction of fenquinotrione verified in the in vitro test on a plant body, recombinant *Arabidopsis thaliana* having the AK454412 gene introduced thereinto was created to examine a difference in fenquinotrione sensitivity from wild type.

Figure 8:
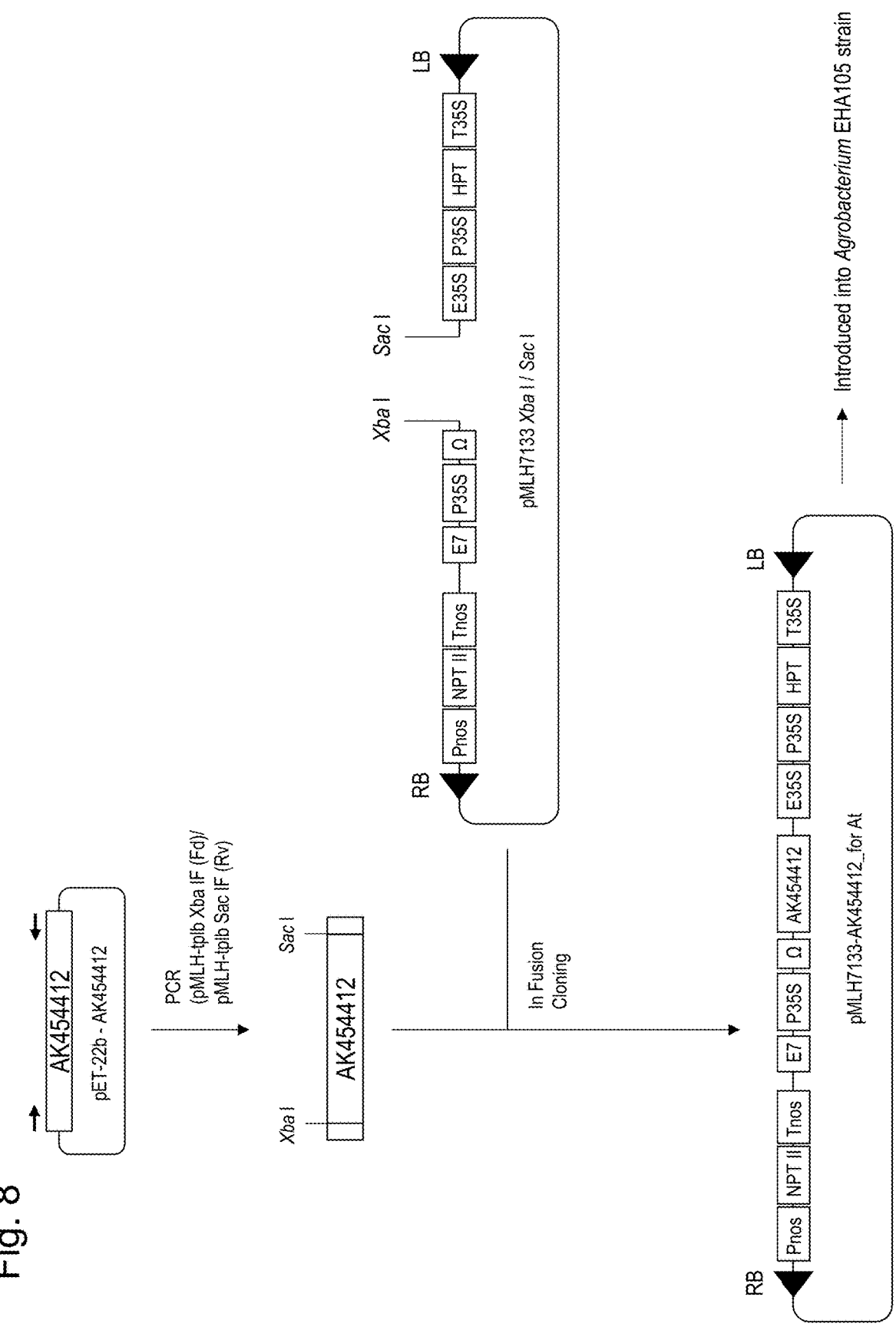
FIG. 8 is a characteristic diagram illustrating production process of an AK454412 gene forced expression binary vector.

First, a binary vector, pMLH7133-AK454412_for At, for transforming *Arabidopsis thaliana* was produced. With the pET-22b-AK454412 produced in Example 1 used as a template, PCR was performed using a primer set of pMLH-tplb Xba IF (Fd) and pMLH-tplb Sac IF (Rv) to obtain a DNA fragment in which XbaI/SacI recognition sequence and 15 bases of In-Fusion recognition sequence were added to a terminal of full length CDS sequence of the AK454412 gene. The obtained DNA fragment and pMLH7133 vector, having been digested with the restriction enzymes XbaI/SacI, were linked to each other with In-Fusion HD Cloning Kit (Clontech) to produce a binary vector, pMLH7133-AK454412_for At, for transforming *Arabidopsis thaliana* (FIG. 8). The obtained construct was introduced into *Agrobacterium* EHA105 strain by an electroporation method. The transformation of *Arabidopsis thaliana* was performed by a floral dip method using this recombinant *Agrobacterium*.

The sequences of the primers used were as follows:

```
pMLH-tplb Xba IF (Fd):
                                (SEQ ID No. 31)
5'-TACAACTACATCTAGAATGGATAAGGCGTACATTG-3'
pMLH-tplb Sac IF (Rv):
                                (SEQ ID No. 32)
5'-GGGGAAATTCGAGCTCTCAGAGGCTCTGAAGCACG-3'
```

Figure 9:
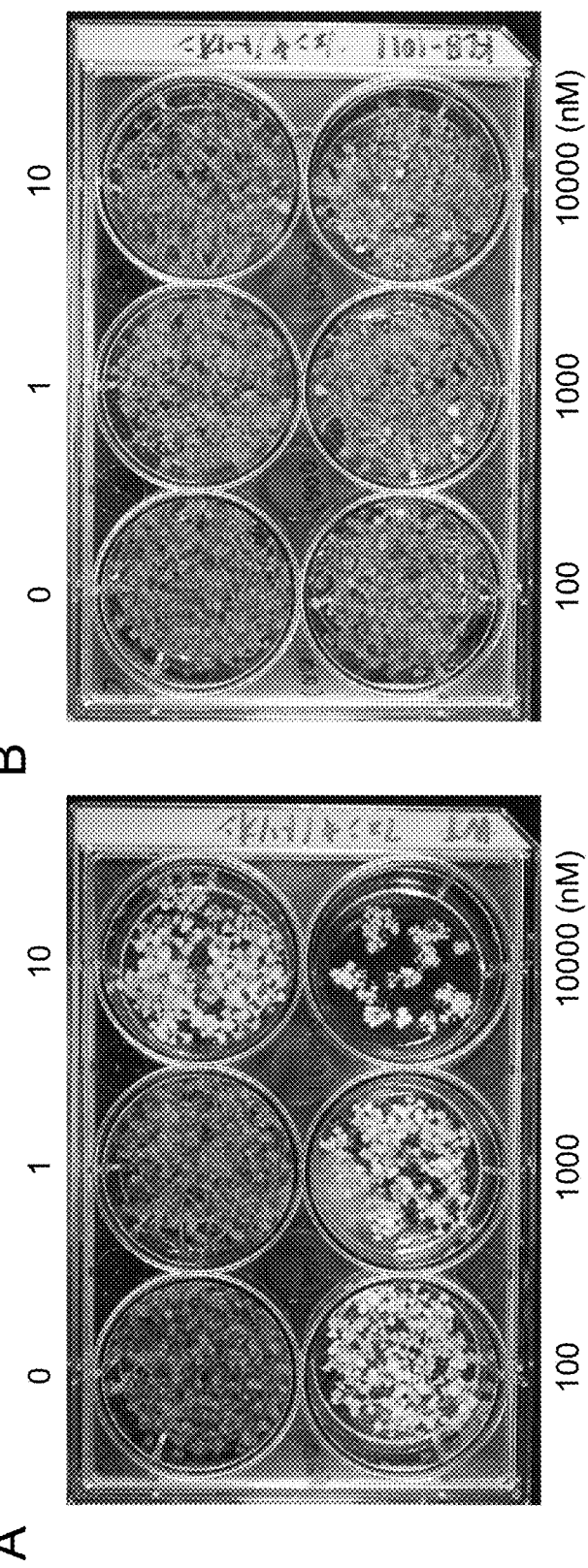
FIG. 9 illustrates photographs of verification results on fenquinotrione resistance in wild type *Arabidopsis thaliana* and *Arabidopsis thaliana* having AK454412 forced expression.

2) Fenquinotrione Sensitivity Test Using *Arabidopsis thaliana* Having AK454412 Forced Expression With a sensitivity difference from wild type *Arabidopsis thaliana* used as an index, it was verified whether or not the created transformant had resistance to fenquinotrione. In MS solid media in each of which fenquinotrione was added to a final concentration of 10,000, 1,000, 100, 10, or 1 nM, or 0.1% of DMSO was added as an untreated plot, sterilized seeds of *Arabidopsis thaliana* having AK454412 forced expression and wild type *Arabidopsis thaliana* were each seeded, and grown at 22° C. for about 10 days. The sensitivity to this drug was evaluated subjectively in accordance with the degree of chlorosis of acting symptom. The results are illustrated in FIG. 9. FIG. 9(A) illustrates results obtained in using the wild type *Arabidopsis thaliana*, and FIG. 9(B) illustrates results obtained in using the *Arabidopsis thaliana* having AK454412 forced expression. As illustrated in FIG. 9, 90% or more of the wild type *Arabidopsis thaliana* had chlorosis through the treatment with 10 nM fenquinotrione, but the chlorosis symptom was not observed in the *Arabidopsis thaliana* having AK454412 forced expression even with 10,000 nM fenquinotrione. This result revealed that the AK454412 gene is greatly involved in metabolic degradation of fenquinotrione, and imparts resistance to fenquinotrione to a plant when expressed therein.

[Example 3] Test of Sensitivity to Various Drugs
Using *Arabidopsis thaliana* Having AK454412
Forced Expression It was revealed that the safety factor of fenquinotrione in wheat is metabolic degradation caused by AK454412. On the other hand, it has been shown that CYP81A6 metabolically degrades fenquinotrione in a rice plant, and it has been reported that it is involved in metabolic degradation of not only fenquinotrione but also sulfonylurea-based ALS inhibitors such as bentazone and bensulfuron-methyl (Gang Pan et al, Plant Mol Biol (2006) 61:933-943). This CYP81A6 and the wheat P450 of AK454412 are comparatively highly homologous to each other, and hence it was presumed that the AK454412 gene may be also involved in the metabolic degradation of these drugs similarly to CYP81A6.

Therefore, similar tests were performed on compounds having various acting properties described in HRAC including these sulfonylurea-based ALS inhibitors to search for a compound that can be metabolically degraded by AK454412. Specifically, 61 compounds arbitrarily selected from all of the 25 classifications of HRAC 2020 were subjected to sensitivity examination in *Arabidopsis thaliana* having AK454412 introduced thereinto and wild type. The sensitivity to each of the drugs was evaluated subjectively with respect to every acting symptom.

As a result, compounds found to have a difference in the sensitivity between the wild type and the recombinant *Arabidopsis thaliana* are illustrated in FIGS. 10-1 to 10-4. It is noted that concentrations of the drug in respective wells of a plate shown in each photograph in FIGS. 10-1 to 10-4 are 0, 0.1, and 1 nM in the stated order in the rightward direction in an upper portion, and 10, 100, and 1,000 nM in the stated order in the rightward direction in a lower portion. Besides, the compound found to have a sensitivity difference are listed below. Each parenthesized numeral indicates an approximate sensitivity difference evaluated subjectively based on a drug concentration exhibiting the effect.

HRAC code 2 (ALS inhibitors)

Bispyribac-sodium salt (<5), pyrithiobac-sodium salt (100), pyrimisulfan (100), penoxsulam (100), bensulfuron-methyl (10), metsulfuron-methyl (<10), imazaquin (≤10), nicosulfuron (<10), sulfometuron-methyl (5)

HRAC code 6 (PS II inhibitor)

bentazone (<5)

HRAC code 14 (PPO inhibitors)

oxadiargyl (2), sulfentrazone (10), pyraflufen-ethyl (10), fomesafen (3)

HRAC code 12 (PDS inhibitors)

diflufenican (2), picolinafen (2), fluridone (2), norflurazon (2)

HRAC code 27 (HPPD inhibitors)

pyrazolate (<100), benzofenap (<100)

HRAC code 18 (DHP synthase inhibitor)

asulam (<10)

HRAC code 3 (microtubule assembly inhibitor)

pendimethalin (<100)

Based on these results, it was revealed that the compounds that can be metabolically degraded by AK454412 are 23 compounds among all the 62 compounds including fenquinotrione, and are the acetolactate synthase inhibitors classified as code 2 of HRAC classifications, the photosystem II inhibitor classified as code 6 of HRAC classifications, the protoporphyrinogen oxidase inhibitors classified as code 14 of HRAC classifications, the carotenoid biosynthesis inhibitors in the phytoene desaturase (PDS) classified as code 12 of HRAC classifications, the 4-hydroxyphenylpyruvate dioxygenase inhibitors classified as code 27 of HRAC classifications, the dihydropteroate synthase inhibitor classified as code 18 of HRAC classifications, and the microtubule assembly inhibitor classified as code 3 of HRAC classifications.

On the other hand, it is only bentazone, sulfonylurea-based ALS inhibitors such as bensulfuron-methyl, fenquinotrione, pyrimisulfan, and pyriminobac-methyl (three acting properties in HRAC classifications) that have been reported so far as compounds against which CYP81A6 exhibits metabolic reactivity. This also revealed that the AK454412 gene is highly homologous to the CYP81A6 gene, but encodes a P450 largely different in substrate recognition. In particular, it was revealed that the wheat-derived AK454412 gene can metabolically degrade a larger number of drugs having different acting properties as compared with the rice-derived homologous gene CYP81A6 and the conventionally known P450 genes.

[Example 4] Verification of Conservation of AK454412 Gene in Respective Wheat Breeds As described above, it was revealed that the AK454412 gene of a wheat-derived novel P450 can detoxify/metabolize the largest number of drugs among all P450s of plants found so far. In the above-described examples, the AK454412 gene isolated from Apache, which is a breed of bread wheat, was used for the examination, and in order to verify whether or not this gene functions regardless of wheat breed, conservation of this gene in various wheat breeds was examined.

Specifically, the verification was conducted by performing gene sequence analysis and gene expression level analysis on 13 breeds of bread wheat (Yumekaori, Hanamanten, Yumeseiki, Norin No. 61, Kitahonami, Kinuhikari, Shunyou, Bolak, Sentinel, EGA Wedgetail, Gatalina, Yopti, and Apache), and 5 breeds of durum wheat (Orlo, Miradoux, Argeles, Tamarai, and Jandaroi).

A method for the gene sequence analysis will be described below. A wheat seedling cultivated in Hoagland's No. 2 (Sigma-Aldrich) solid medium for about 1 week was frozen crushed with liquid nitrogen, and a total RNA was extracted therefrom with RNeasy Plant Mini Kit (Qiagen). The obtained total RNA was subjected to DNase I treatment with Deoxyribonuclease RT Grade for Heat Stop (NIPPON GENE CO., LTD.), and then a cDNA was synthesized with Transcriptor First Strand cDNA Synthesis Kit (Roche). For a reverse transcription reaction, Oligo dT Primer and Random Hexamer Primer were both used. With the produced cDNA of each wheat breed used as a template, PCR was performed using a primer set of AK454412 5'-UTR (Fd) and AK454412 3'-UTR (Rv) to amplify a region from 5'-UTR to 3'-UTR of the gene. The resultant DNA fragments were purified with GFX PCR DNA and Gel Band Purification Kit (GE Healthcare Science), and subjected to sequence analysis using various primers.

As a result of the sequence analysis performed on the 18 breeds of bread wheat and durum wheat, Norin No. 61, Kinuhikari, Sentinel, and EGA Wedgetail of the bread wheat breeds had a gene sequence completely matching the nucleotide sequence of the AK454412 gene described in GenBank. Besides, Miradoux, Argeles, Tamarai, and Jandaroi of the durum wheat breeds had a gene sequence obtained by mutating the 1,137th T to C (C1137T) in the nucleotide sequence of the AK454412 gene. In addition, Yumekaori, Hanamanten, Yumeseiki, Kitahonami, Shunyou, Bolak, Gatalina, Yipti, and Apache of the bread wheat breeds had a gene sequence obtained by mutating the 453rd C to T (C453T) and the 1,137th T to C (T1137C) in the nucleotide sequence of the AK454412 gene. It is noted that these two mutations are silent mutations, and did not affect the amino acid sequences. Besides, Orlo of the durum wheat breed had a gene sequence including C453T, G1114A, T1137C, and C1179T mutations in the nucleotide sequence of the AK454412 gene. Among these mutations, the G1114A (V372M) mutation alone was a mutation involving amino acid mutation. It was found, based on these results, that almost all the breeds tested in the present example have the same gene as or functionally equivalent gene to the AK454412 gene.

Figure 11:
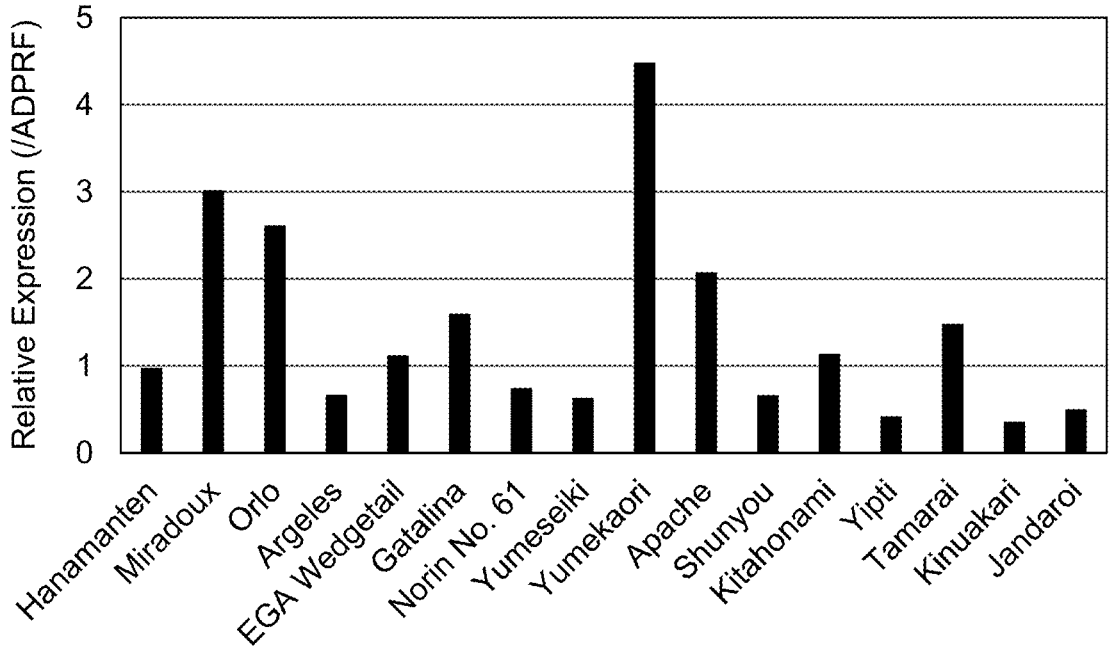
FIG. 11 is a characteristic diagram illustrating results of expression analysis of AK454412 gene in various wheats.

Subsequently, the expression analysis was performed as follows. Real time PCR was performed with the cDNA of each wheat breed produced as described above used a template. In order to prepare a reaction system of the real time PCR, GoTaq qPCR Master Mix (Promega Corporation) was used, and Thermal Cycler Dice Real Time System TP800 (TaKaRa) was used as a thermal cycler. As reaction conditions for the PCR, initial denaturation was performed at 95° C. for 30 seconds, denaturation was performed at 95° C. for 5 seconds, and annealing/elongation was performed at 60° C. for 30 seconds (45 cycles). As a reference gene, ADP-Ribosylation Factor gene (accession No. AB050957) was used. As an analysis method for a Ct value, a Crossing Point method was employed, and relative quantification was calculated by a calibration curve method. The results are illustrated in FIG. 11. As illustrated in FIG. 11, the gene expression level was about 0.5 to 4.5 in terms of a ratio to reference gene expression in all the breeds, and thus, it was found that they had comparatively high expression levels equivalent to or higher than that of the reference gene.

It was thus reveled that the AK454412 gene is conserved in various wheat breeds, and functions therein.

The sequences of the primers used were as follows:

```
                                      (SEQ ID No. 33)
ADP-RF (Fd); 5'-GCTCTCCAACAACATTGCCAAC-3'

(SEQ ID No. 34)
ADP-RF (Rv); 5'-GCTTCTGCCTGTCACATACGC-3'

(SEQ ID No. 35)
AK454412 RT (Fd); 5'-CTCTGCGCGAATTTATTTGG-3'

(SEQ ID No. 36)
AK454412 RT (Rv); 5'-TCACGATGCACTGCAGGTAG-3'
```

[Example 5] Functional Analysis of KJ541960, Homologous Gene to AK454412

Figure 12:
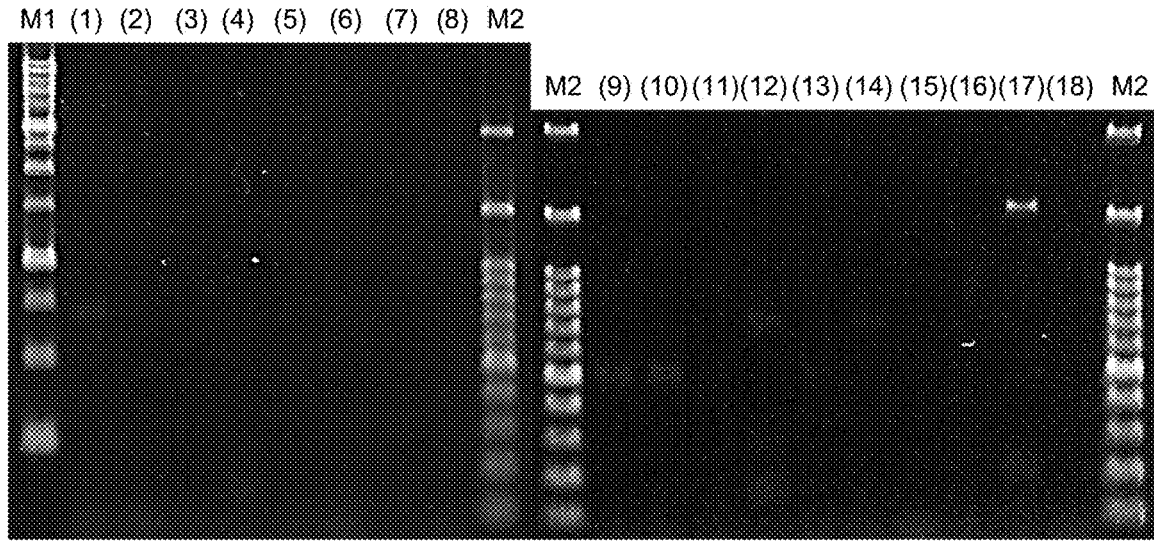
FIG. 12 is an electrophoresis photograph illustrating a result of PCR using a primer set for amplifying KJ541960 gene.

As described in Example 1, when blast search was performed on GenBank with the AK454412 gene used as a query, Accession No. KJ541960 (having homology of 96% identity in an amino acid sequence excluding a transmembrane region to the AK454412 gene) was hit as the wheat-derived putative P450 gene. Because of high homology to the AK454412 gene, it was also verified whether or not the KJ541960 gene has the similar function to the AK454412 gene. With a cDNA of each of the 18 wheat breeds used as a template, PCR was performed using a primer set of KJ541960 5'-UTR (Fd) and KJ541960 3'-UTR (Rv) to amplify a region from 5'-UTR to 3'-UTR of KJ541960. As a result, a band was found in the vicinity of a predicted position in only one breed (Tamarai) (FIG. 12). In order to check whether or not this DNA fragment matches the target gene, this DNA fragment was subjected to sequence analysis, and it was revealed that this was not the target gene. Based on these results, it was presumed that this gene may not be present in the wheat breeds tested here.

Figure 13:
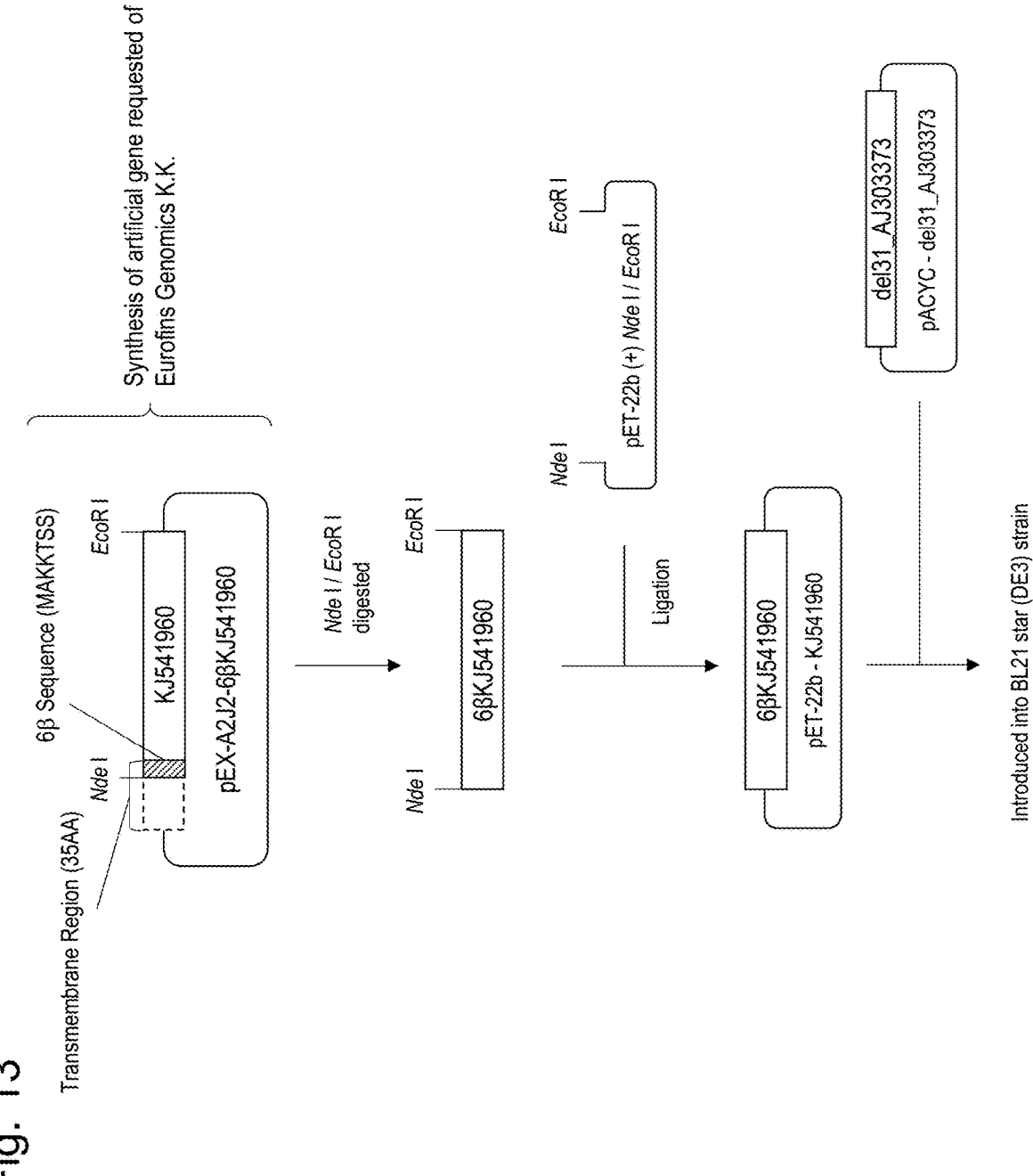
FIG. 13 is a characteristic diagram illustrating production process of a KJ541960 gene expression vector.

Therefore, synthesis of an artificial gene of the KJ541960 gene was requested of Eurofins Genomics K.K. Here, NdeI and EcoRI sites were respectively added to the 5' and 3' terminals of the CDS sequence of the gene. A DNA fragment of the KJ541960 gene was cleaved through NdeI/EcoRI treatment from the synthesized pEX-A2J2-KJ541960 plasmid, and was linked to pET-22b(+) vector, similarly having been subjected to NdeI/EcoRI treatment, with Ligation-Convenience Kit, and thus pET-22b-KJ541960 was produced (FIG. 13). This expression construct was co-introduced into BL21 star (DE3) strain together with pACYC-del31_TaCPR to be used for protein expression.

Figure 14:
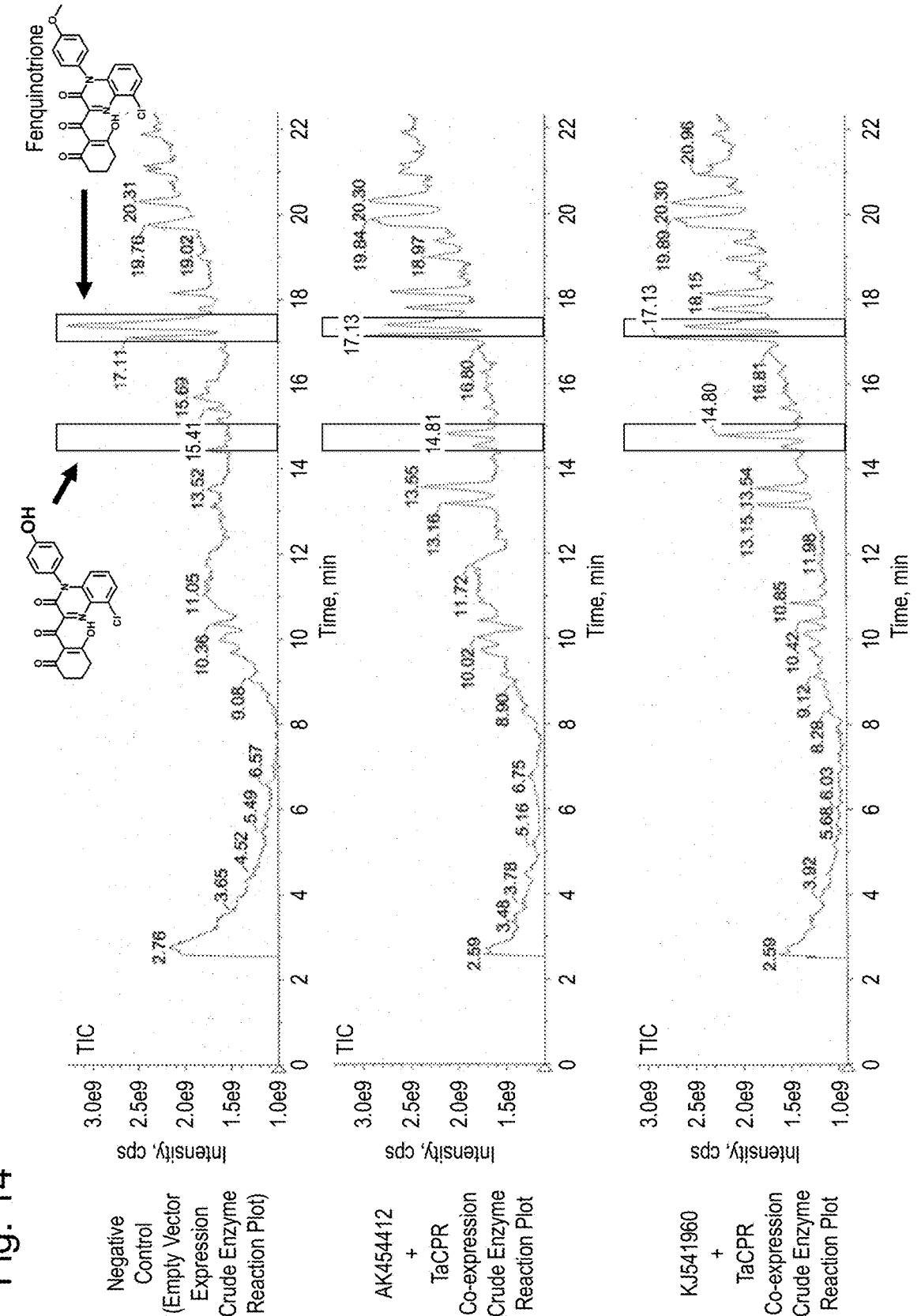
FIG. 14 is a characteristic diagram illustrating a result of in vitro drug metabolism test of KJ541960 protein performed against fenquinotrione.

It is noted that the KJ541960 gene, synthesized as the artificial gene, was set to encode an amino acid sequence, in which a membrane anchoring region of the 35 N-terminal amino acid residues was removed, and the 6β sequence (MAKKTSS) was added as the same conditions as in the AK454412 gene. The protein expression, enzyme preparation, in vitro reaction, and analysis performed thereafter were performed by employing the test method and conditions described in Example 1. In the in vitro drug metabolism test, fenquinotrione was used as a substrate to be reacted with recombinant protein, and evaluation was performed with production of a metabolite of a demethylated product used as an index. The results are illustrated in FIG. 14. As illustrated in FIG. 14, in an empty vector crude enzyme reaction plot, used as a negative control plot, the demethylated product was not detected, but in positive control plots of AK454412 reaction plot and KJ541960 reaction plot, a parent peak of fenquinotrione was reduced, and a peak of the demethylated product appeared. Besides, the intensity of the peak of the detected demethylated product was substantially the same in both the reaction plots. It was presumed, based on this, that KJ541960 has drug metabolic capacity similar to that of AK454412.

The sequences of the primers used were as follows:

```
KJ541960 5'-UTR(Fd):
                              (SEQ ID No. 37)
5'-CAACCTGAGACCTCAAGTGTCAC-3'

KJ541960 3'-UTR (Rv):
                              (SEQ ID No. 38)
5'-CAGTGCTACCGCAAGATAGCTAC-3'
```

[Example 6] Functional Analysis of Barley-Derived AK375492 and AK369081, Homologous Genes to AK454412

The barley-derived genes Accession Nos. AK375492 and AK369081, which are homologous genes to CYP81A6, described in Example 1 respectively have homology of 93% and 80% identity in the amino acid sequence excluding the transmembrane region to the AK454412 gene. Since these barley-derived genes thus also have high homology to the AK454412 gene, it was also verified whether or not these genes have fenquinotrione metabolic activity.

Figure 15:
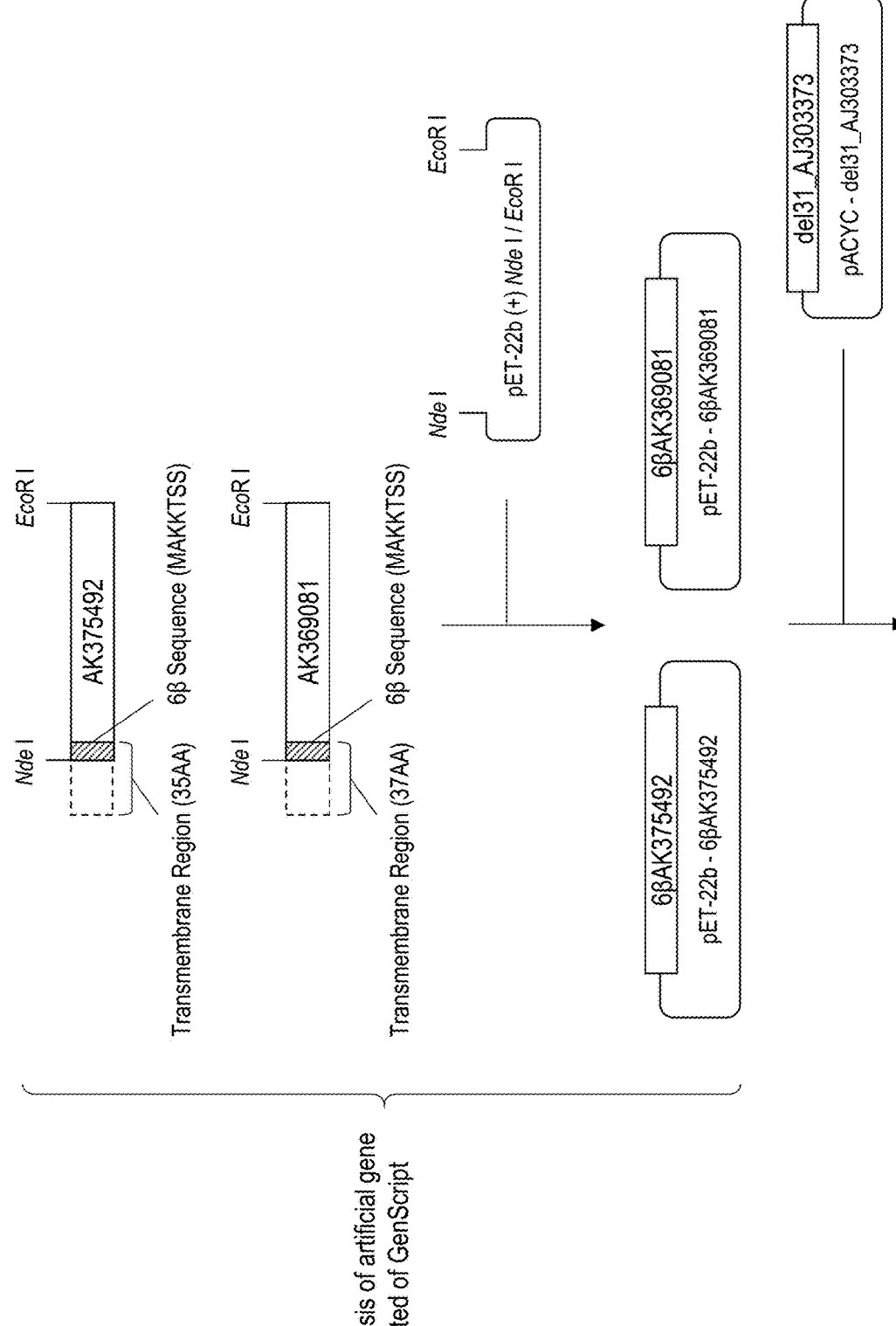
FIG. 15 is a characteristic diagram illustrating production process of AK375492 and AK369081 gene expression vectors.

Specifically, in the same manner as in KJ541960, recombinant proteins of these genes were prepared to evaluate, by in vitro test, whether or not these have fenquinotrione metabolic activity. First, an expression vector was designed by inserting, between NdeI and EcoRI sites of pET-22b(+), a nucleotide sequence, which encoded a sequence obtained by removing the transmembrane region (AK375492: 35 N-terminal amino acid residues, AK369081: 37 N-terminal amino acid residues) of each of the genes of Accession Nos. AK375492 and AK369081, and adding the 6β sequence (MAKKTSS) to the N-terminal, and synthesis of artificial genes was requested of GenScript. Each of the synthesized expression vectors (6β AK375492 in pET-22b, 6β AK369081 in pET-22b) was co-introduced, together with pACYC-del31_TaCPR, into E. coli BL21 star (DE3) strain for protein expression (FIG. 15). The protein expression, enzyme preparation, in vitro reaction, and analysis performed thereafter were performed by employing the test method and conditions described in Example 1.

Figure 16:
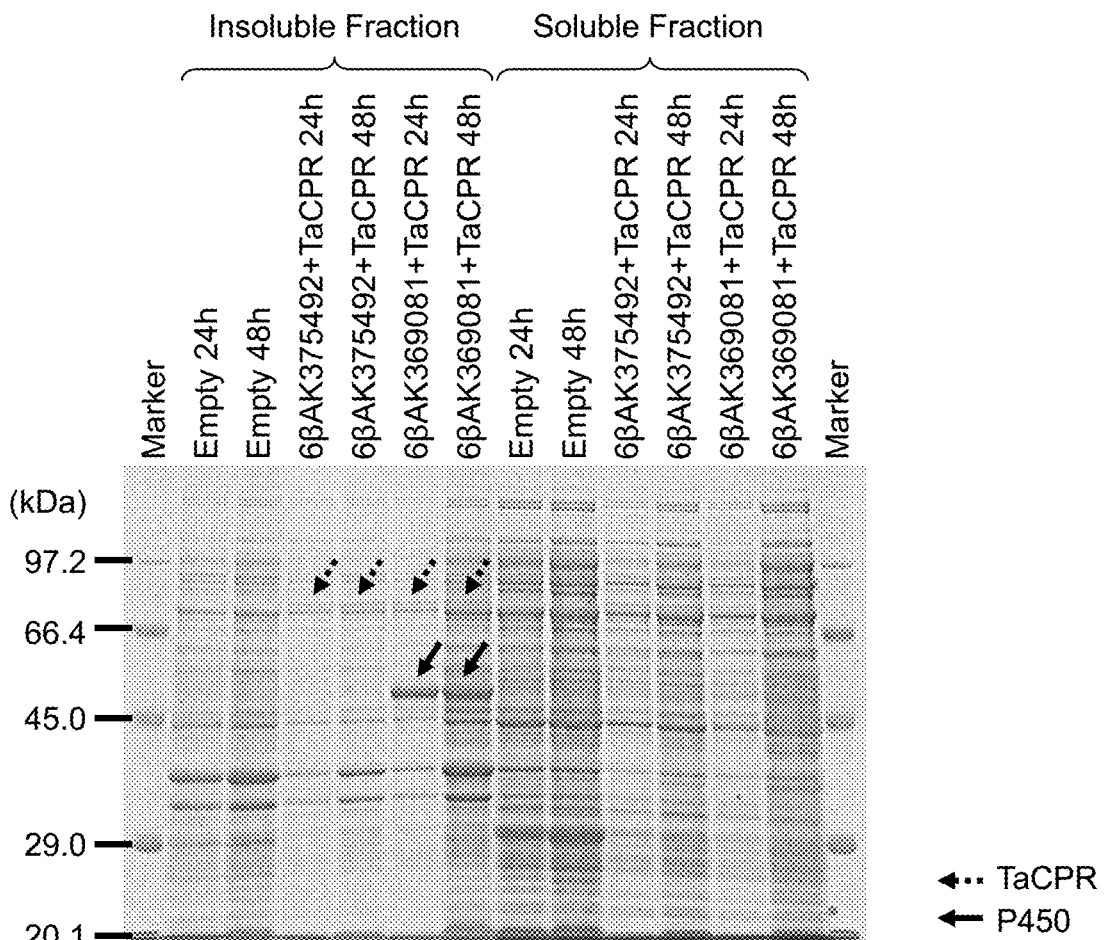
FIG. 16 is a SDS-PAGE photograph illustrating expression of AK375492 and AK369081 proteins and TaCPR protein.
Figure 17:
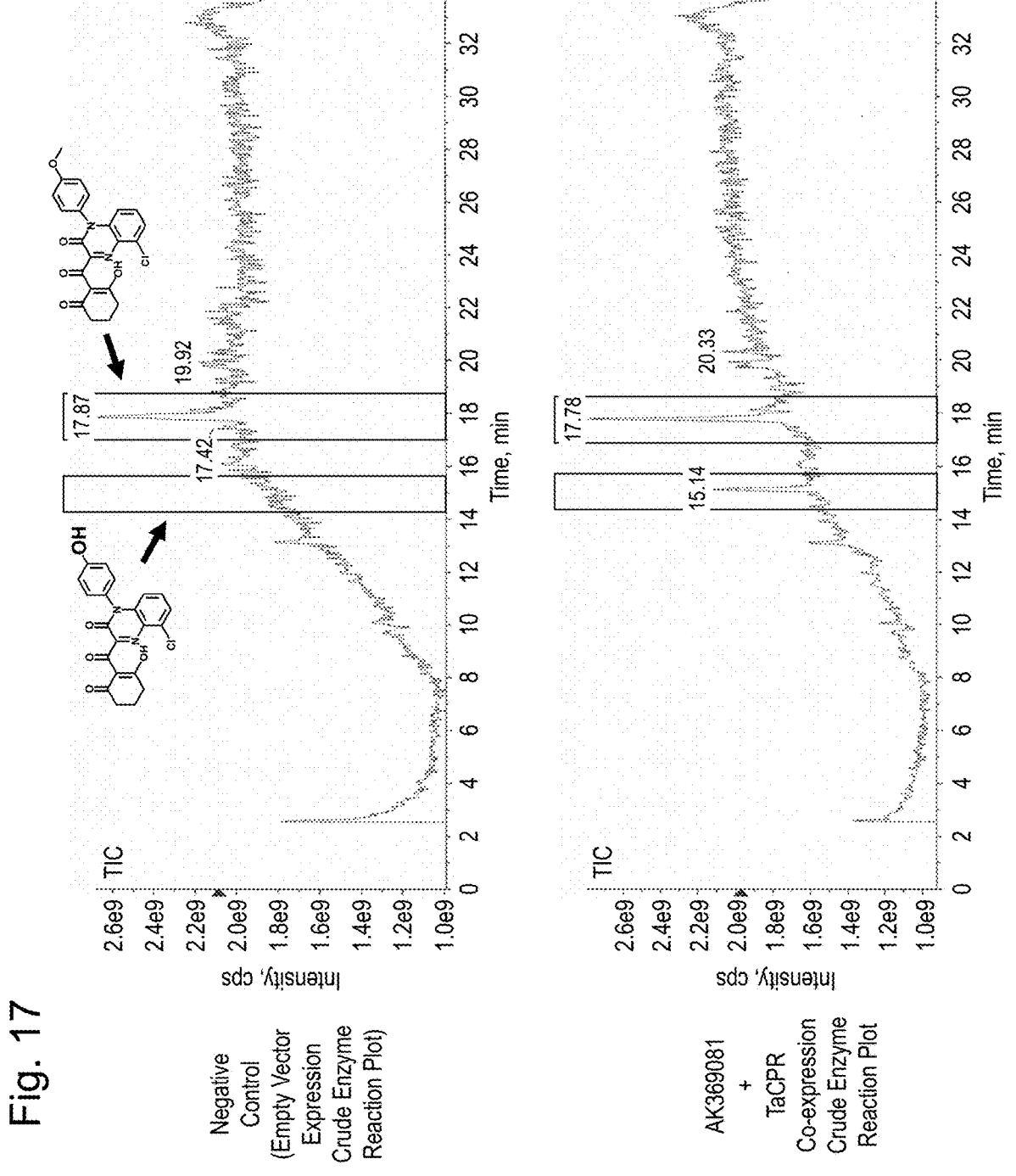
FIG. 17 is a characteristic diagram illustrating a result of in vitro drug metabolism test of AK369081 protein performed against fenquinotrione.

As a result of the protein expression, the expression was confirmed in an insoluble fraction in only AK369081, and the target protein was not expressed in AK375492 in this expression system (FIG. 16). Therefore, the in vitro drug metabolism test was performed on AK369081 alone. In the in vitro drug metabolism test, fenquinotrione was used as a substrate to be reacted with a recombinant protein, and evaluation was performed with generation of a metabolite of a demethylated product used as an index. The results are illustrated in FIG. 17. As illustrated in FIG. 17, a peak was not detected except for that of the parent compound in an empty vector crude enzyme reaction plot used as a negative control plot, but a peak of the demethylated product (RT=in the vicinity of 15.1) appeared in the AK369081 reaction plot. Based on this, it was presumed that AK369081 has fenquinotrione metabolic capacity similarly to AK454412.

It is noted that all publications, patents, and patent applications cited herein are incorporated herein by reference in their entirety.

The invention claimed is:

1. A transformation method comprising the steps of: introducing, into a host cell, an expression vector comprising a cytochrome P450 gene encoding a protein comprising the amino acid sequence of SEQ ID NO:2 and an additional gene; and selecting, as a transformant, a cell that grows in the presence of at least one inhibitor selected from the group consisting of an acetolactate synthase inhibitor classified as code 2 of Herbicide Resistance Action Committee (HRAC) classifications, a microtubule assembly inhibitor classified as code 3 of HRAC classifications, a photosystem II inhibitor classified as code 6 of HRAC classification, a carotenoid biosynthesis inhibitor in phytoene desaturase (PDS) classified as code 12 of HRAC classifications, a protoporphyrinogen oxidase inhibitor classified as code 14 of HRAC classifications, a dihydropteroate synthase inhibitor classified as code 18 of HRAC classifications, and a 4-hydroxyphenylpyruvate dioxygenase inhibitor classified as code 27 of HRAC classifications.

2. The method according to claim 1, wherein the protein consists of the amino acid sequence of SEQ ID NO: 10.

* * * * *

SEQUENCE LISTING

```
<160> NUMBER OF SEQ ID NOS: 39

<210> SEQ ID NO 1
<211> LENGTH: 1452
<212> TYPE: DNA
<213> ORGANISM: Triticum aestivum
<220> FEATURE:
<221> NAME/KEY: CDS
<222> LOCATION: (1)..(1452)

<400> SEQUENCE: 1 ctg ccg ccg agc ccc ccg gcc atc ccg ttc ctc ggc cac ctc cac ctc      48
Leu Pro Pro Ser Pro Pro Ala Ile Pro Phe Leu Gly His Leu His Leu
1               5                   10                  15 ctg gag aag ccg ttc cat gcc gcg ctg cgc cgc ctc gcc gcg cgc ctc      96
Leu Glu Lys Pro Phe His Ala Ala Leu Arg Arg Leu Ala Ala Arg Leu
```

-continued

```
              20                    25                    30
ggc ccg gtc ttc tcg ctg cgg ctc ggc tcg cgc cgc gcc gtt gtg gtc          144
Gly Pro Val Phe Ser Leu Arg Leu Gly Ser Arg Arg Ala Val Val Val
         35                    40                    45 tcc tcg gcg gag tgc gcc agg gag tgc ttc acg gag cac gac gtg acg          192
Ser Ser Ala Glu Cys Ala Arg Glu Cys Phe Thr Glu His Asp Val Thr
         50                    55                    60 ttc gcc aac cgg ccc cgg ttc ccc tcg cag ctg ctc gtc tcc ttc gac          240
Phe Ala Asn Arg Pro Arg Phe Pro Ser Gln Leu Leu Val Ser Phe Asp
65                    70                    75                    80 ggc gcc gcg ctc gtc acg tcc agc tac ggc ccg cac tgg cgc aac ctc          288
Gly Ala Ala Leu Val Thr Ser Ser Tyr Gly Pro His Trp Arg Asn Leu
                   85                    90                    95 cgc cgc gtc gcc gcc gtg cag ctg ctc tcc gcg cac cgc gtc gcc tgc          336
Arg Arg Val Ala Ala Val Gln Leu Leu Ser Ala His Arg Val Ala Cys
              100                   105                   110 atg tct ggc gtc atc gcc ggc gag gtg cgc gcc atg gcg cgc cgg ctg          384
Met Ser Gly Val Ile Ala Gly Glu Val Arg Ala Met Ala Arg Arg Leu
              115                   120                   125 ttc cgc gcc gcc gcg gcg tcc ccc ggc ggc gat ggc gcc gcg cgg gtc          432
Phe Arg Ala Ala Ala Ala Ser Pro Gly Gly Asp Gly Ala Ala Arg Val
         130                   135                   140 cag ctg aag cgg agg ctc ttc gag ctc tcc ctc agc gtg ctc atg gag          480
Gln Leu Lys Arg Arg Leu Phe Glu Leu Ser Leu Ser Val Leu Met Glu
145                   150                   155                   160 acc atc gcc cag acc aag gcg acc cgg tcg gag gcc gac gcc gac acg          528
Thr Ile Ala Gln Thr Lys Ala Thr Arg Ser Glu Ala Asp Ala Asp Thr
                   165                   170                   175 gac atg tcc gtg gag gcc cag gag ttc aag aag gtg gtg gac gag ctc          576
Asp Met Ser Val Glu Ala Gln Glu Phe Lys Lys Val Val Asp Glu Leu
              180                   185                   190 atc ccg tac ctc ggc gcc gcc aac acg tgg gat tac ctg ccg gtg ttg          624
Ile Pro Tyr Leu Gly Ala Ala Asn Thr Trp Asp Tyr Leu Pro Val Leu
              195                   200                   205 cgg tgg ttc gac gtg ttc ggc gtg agg aac aag atc ctg gcc gcc gtg          672
Arg Trp Phe Asp Val Phe Gly Val Arg Asn Lys Ile Leu Ala Ala Val
         210                   215                   220 agc agg agg gac gcc ttc atg ctg cgt ctc atc gac aac gag cgc cgg          720
Ser Arg Arg Asp Ala Phe Met Leu Arg Leu Ile Asp Asn Glu Arg Arg
225                   230                   235                   240 agg ctc gac gac gct ggc acc gaa ggc gac aag aag agc atg atc gcc          768
Arg Leu Asp Asp Ala Gly Thr Glu Gly Asp Lys Lys Ser Met Ile Ala
                   245                   250                   255 gtg ctc ctc aat ctg cag aag acg gag ccg gag gtg tac gcc gat acc          816
Val Leu Leu Asn Leu Gln Lys Thr Glu Pro Glu Val Tyr Ala Asp Thr
              260                   265                   270 atg atc acg gct ctc tgc gcg aat tta ttt ggg gcc gga acg gag acc          864
Met Ile Thr Ala Leu Cys Ala Asn Leu Phe Gly Ala Gly Thr Glu Thr
         275                   280                   285 acg tcg acg acg acg gag tgg gcg atg tcg ctg ctg ctg aac cac ccg          912
Thr Ser Thr Thr Thr Glu Trp Ala Met Ser Leu Leu Leu Asn His Pro
         290                   295                   300 gcg gcg ctc aaa aag gcg cag gcc gag atc gac gcg gcc gtg ggc acc          960
Ala Ala Leu Lys Lys Ala Gln Ala Glu Ile Asp Ala Ala Val Gly Thr
305                   310                   315                   320 tcc cgg ctg gtg acc gcc gac gac gtg cca cgg ctg gcc tac ctg cag         1008
Ser Arg Leu Val Thr Ala Asp Asp Val Pro Arg Leu Ala Tyr Leu Gln
                   325                   330                   335 tgc atc gtg agc gag acg ctg cgg ctg tat ccg gcg gcg ccg atg ctg         1056
```

-continued

```
Cys Ile Val Ser Glu Thr Leu Arg Leu Tyr Pro Ala Ala Pro Met Leu
            340                 345                 350 ctg ccg cac gag tcc tcg gca gac tgc aag gtg ggc ggc tac aac gtg        1104
Leu Pro His Glu Ser Ser Ala Asp Cys Lys Val Gly Gly Tyr Asn Val
            355                 360                 365 ccg agc ggc acg atg ctg atg gtg aac gcg tac gcc atc cac cgg gac        1152
Pro Ser Gly Thr Met Leu Met Val Asn Ala Tyr Ala Ile His Arg Asp
370                 375                 380 ccg gcg gcg tgg gag cgg ccg ctg gag ttc gtc ccg gag cgg ttc gag        1200
Pro Ala Ala Trp Glu Arg Pro Leu Glu Phe Val Pro Glu Arg Phe Glu
385                 390                 395                 400 gac ggg aag gcc gag ggg cgg ttc atg atc ccg ttc ggg atg ggc cgc        1248
Asp Gly Lys Ala Glu Gly Arg Phe Met Ile Pro Phe Gly Met Gly Arg
                405                 410                 415 cgg cgg tgc ccc ggg gag acg ctg gcg ctg cgg acc atc ggc atg gtg        1296
Arg Arg Cys Pro Gly Glu Thr Leu Ala Leu Arg Thr Ile Gly Met Val
            420                 425                 430 ctg gcc acg ctg gtg cag tgc ttc gac tgg gag cgc gtc gac ggc gcg        1344
Leu Ala Thr Leu Val Gln Cys Phe Asp Trp Glu Arg Val Asp Gly Ala
            435                 440                 445 gag gtg gac atg acg gag ggc ggc ggg ctc acc atc ccc aag gtc gtg        1392
Glu Val Asp Met Thr Glu Gly Gly Gly Leu Thr Ile Pro Lys Val Val
            450                 455                 460 cca ctc gag gcc gtg tgc agg ccg cgc ccg gcc atg cgc gac gtg ctt        1440
Pro Leu Glu Ala Val Cys Arg Pro Arg Pro Ala Met Arg Asp Val Leu
465                 470                 475                 480 cag agc ctc tga                                                        1452
Gln Ser Leu <210> SEQ ID NO 2
<211> LENGTH: 483
<212> TYPE: PRT
<213> ORGANISM: Triticum aestivum

<400> SEQUENCE: 2

Leu Pro Pro Ser Pro Pro Ala Ile Pro Phe Leu Gly His Leu His Leu
1               5                   10                  15

Leu Glu Lys Pro Phe His Ala Ala Leu Arg Arg Leu Ala Ala Arg Leu
                20                  25                  30

Gly Pro Val Phe Ser Leu Arg Leu Gly Ser Arg Arg Ala Val Val Val
            35                  40                  45

Ser Ser Ala Glu Cys Ala Arg Glu Cys Phe Thr Glu His Asp Val Thr
        50                  55                  60

Phe Ala Asn Arg Pro Arg Phe Pro Ser Gln Leu Leu Val Ser Phe Asp
65                  70                  75                  80

Gly Ala Ala Leu Val Thr Ser Ser Tyr Gly Pro His Trp Arg Asn Leu
                85                  90                  95

Arg Arg Val Ala Ala Val Gln Leu Leu Ser Ala His Arg Val Ala Cys
                100                 105                 110

Met Ser Gly Val Ile Ala Gly Glu Val Arg Ala Met Ala Arg Arg Leu
            115                 120                 125

Phe Arg Ala Ala Ala Ala Ser Pro Gly Gly Asp Gly Ala Ala Arg Val
            130                 135                 140

Gln Leu Lys Arg Arg Leu Phe Glu Leu Ser Leu Ser Val Leu Met Glu
145                 150                 155                 160

Thr Ile Ala Gln Thr Lys Ala Thr Arg Ser Glu Ala Asp Ala Asp Thr
                165                 170                 175
```

```
Asp Met Ser Val Glu Ala Gln Glu Phe Lys Lys Val Val Asp Glu Leu
            180                 185                 190

Ile Pro Tyr Leu Gly Ala Ala Asn Thr Trp Asp Tyr Leu Pro Val Leu
            195                 200                 205

Arg Trp Phe Asp Val Phe Gly Val Arg Asn Lys Ile Leu Ala Ala Val
            210                 215                 220

Ser Arg Arg Asp Ala Phe Met Leu Arg Leu Ile Asp Asn Glu Arg Arg
225                 230                 235                 240

Arg Leu Asp Asp Ala Gly Thr Glu Gly Asp Lys Lys Ser Met Ile Ala
            245                 250                 255

Val Leu Leu Asn Leu Gln Lys Thr Glu Pro Glu Val Tyr Ala Asp Thr
            260                 265                 270

Met Ile Thr Ala Leu Cys Ala Asn Leu Phe Gly Ala Gly Thr Glu Thr
            275                 280                 285

Thr Ser Thr Thr Thr Glu Trp Ala Met Ser Leu Leu Leu Asn His Pro
            290                 295                 300

Ala Ala Leu Lys Lys Ala Gln Ala Glu Ile Asp Ala Ala Val Gly Thr
305                 310                 315                 320

Ser Arg Leu Val Thr Ala Asp Asp Val Pro Arg Leu Ala Tyr Leu Gln
            325                 330                 335

Cys Ile Val Ser Glu Thr Leu Arg Leu Tyr Pro Ala Ala Pro Met Leu
            340                 345                 350

Leu Pro His Glu Ser Ser Ala Asp Cys Lys Val Gly Gly Tyr Asn Val
            355                 360                 365

Pro Ser Gly Thr Met Leu Met Val Asn Ala Tyr Ala Ile His Arg Asp
            370                 375                 380

Pro Ala Ala Trp Glu Arg Pro Leu Glu Phe Val Pro Glu Arg Phe Glu
385                 390                 395                 400

Asp Gly Lys Ala Glu Gly Arg Phe Met Ile Pro Phe Gly Met Gly Arg
            405                 410                 415

Arg Arg Cys Pro Gly Glu Thr Leu Ala Leu Arg Thr Ile Gly Met Val
            420                 425                 430

Leu Ala Thr Leu Val Gln Cys Phe Asp Trp Glu Arg Val Asp Gly Ala
            435                 440                 445

Glu Val Asp Met Thr Glu Gly Gly Gly Leu Thr Ile Pro Lys Val Val
            450                 455                 460

Pro Leu Glu Ala Val Cys Arg Pro Arg Pro Ala Met Arg Asp Val Leu
465                 470                 475                 480

Gln Ser Leu
```

```
<210> SEQ ID NO 3
<211> LENGTH: 1452
<212> TYPE: DNA
<213> ORGANISM: Triticum aestivum
<220> FEATURE:
<221> NAME/KEY: CDS
<222> LOCATION: (1)..(1452)

<400> SEQUENCE: 3 ctg ccg ccg agc ccc cag gcc atc ccg ttc ctc ggc cac ctc cac ctc       48
Leu Pro Pro Ser Pro Gln Ala Ile Pro Phe Leu Gly His Leu His Leu
1               5                   10                  15 ctg gag aag ccg ttc cac gcc gct ctg tgc cgc ctc gcc gag cgc ctc       96
Leu Glu Lys Pro Phe His Ala Ala Leu Cys Arg Leu Ala Glu Arg Leu
            20                  25                  30 ggc ccg gtc ttc tcg ctg cgc ctc ggc tcg cgc cgc gcc gtg gtc gtc      144
```

-continued

```
                    Gly Pro Val Phe Ser Leu Arg Leu Gly Ser Arg Arg Ala Val Val Val
                        35                  40                  45 tcc tcg gcg gag tgc gcc agg gag tgc ttc acg gag cac gac gtg atc          192
Ser Ser Ala Glu Cys Ala Arg Glu Cys Phe Thr Glu His Asp Val Ile
50                  55                  60 ttc gcc gac cgg ccc cag ttc ccc tcg cag ctg ctc gtg tcc ttc gac          240
Phe Ala Asp Arg Pro Gln Phe Pro Ser Gln Leu Leu Val Ser Phe Asp
65                  70                  75                  80 ggc atc gcg ctc tcc acg tcc agc tac ggc ccg cac tgg cgc aac ctc          288
Gly Ile Ala Leu Ser Thr Ser Ser Tyr Gly Pro His Trp Arg Asn Leu
                    85                  90                  95 cgc cgc gtc gcc gcc gtg cag ctg ctc tct gcg cac cgc gtc gcc tgc          336
Arg Arg Val Ala Ala Val Gln Leu Leu Ser Ala His Arg Val Ala Cys
                100                 105                 110 atg tcc ggc gtg atc ggg ggc gag gtg cgc gcc atg gcg cgc cgg ctc          384
Met Ser Gly Val Ile Gly Gly Glu Val Arg Ala Met Ala Arg Arg Leu
            115                 120                 125 ttc cgc gcc gcc gcg gcg tcc ccc ggt ggg gac ggc gcc gcg cgg gtc          432
Phe Arg Ala Ala Ala Ala Ser Pro Gly Gly Asp Gly Ala Ala Arg Val
        130                 135                 140 cag ctg aag cgg agg ctc ttc gag ctc tcc ctc agc gtg ctc atg gaa          480
Gln Leu Lys Arg Arg Leu Phe Glu Leu Ser Leu Ser Val Leu Met Glu
145                 150                 155                 160 acc atc gcc cag acc aag gcg acc cgg tcg gag gcc gac gcc gac acg          528
Thr Ile Ala Gln Thr Lys Ala Thr Arg Ser Glu Ala Asp Ala Asp Thr
                165                 170                 175 gac atg tca gag gag gcc cag gag ttc aag aag gtg gtg gac gag ctc          576
Asp Met Ser Glu Glu Ala Gln Glu Phe Lys Lys Val Val Asp Glu Leu
            180                 185                 190 atc ccg tac ctc ggc gcc gcc aac acg tgg gat tac ctg ccg gtg ttg          624
Ile Pro Tyr Leu Gly Ala Ala Asn Thr Trp Asp Tyr Leu Pro Val Leu
        195                 200                 205 cgg tgg ttc gac gtg ttc ggc gtg agg aac aag atc ctg gcc gcc gtg          672
Arg Trp Phe Asp Val Phe Gly Val Arg Asn Lys Ile Leu Ala Ala Val
    210                 215                 220 agc agg agg gac gcc ttc ctg cat cgt ctc atc gac aac gag cgc cgg          720
Ser Arg Arg Asp Ala Phe Leu His Arg Leu Ile Asp Asn Glu Arg Arg
225                 230                 235                 240 agg ctc gac aac gcc ggc acc gaa ggc gac aag aag agc atg atc gcc          768
Arg Leu Asp Asn Ala Gly Thr Glu Gly Asp Lys Lys Ser Met Ile Ala
                245                 250                 255 gtg ctc ctc aat ctg cag aag acg gag ccg gag gtg tac acc gat acc          816
Val Leu Leu Asn Leu Gln Lys Thr Glu Pro Glu Val Tyr Thr Asp Thr
            260                 265                 270 atg atc acg gct ctc tgc gcg aat tta ttc ggg gcc gga acg gag acc          864
Met Ile Thr Ala Leu Cys Ala Asn Leu Phe Gly Ala Gly Thr Glu Thr
        275                 280                 285 acg tcg acg acg acg gag tgg gcg atg tcg ctg ctg ctg aac cac ccg          912
Thr Ser Thr Thr Thr Glu Trp Ala Met Ser Leu Leu Leu Asn His Pro
    290                 295                 300 gcg gcg ctg agg aag gcg cag gcc gag atc gac gcg gcc gtg ggg acc          960
Ala Ala Leu Arg Lys Ala Gln Ala Glu Ile Asp Ala Ala Val Gly Thr
305                 310                 315                 320 tcc cgg ctg gtg acc gcc gac gac gtg ccc cgg ctg gcc tac ctg cag         1008
Ser Arg Leu Val Thr Ala Asp Asp Val Pro Arg Leu Ala Tyr Leu Gln
                325                 330                 335 tgc atc gtg agc gag acg ctg cgg ctg tac ccg gcg gcg ccg atg ctg         1056
Cys Ile Val Ser Glu Thr Leu Arg Leu Tyr Pro Ala Ala Pro Met Leu
            340                 345                 350
```

-continued

```
ctg ccg cac cag tcc tcg gcg gac tgc aag gtc ggc ggc tac aac gtg      1104
Leu Pro His Gln Ser Ser Ala Asp Cys Lys Val Gly Gly Tyr Asn Val
        355             360             365 ccg agc ggc acg atg ctg atg gtg aac gcg tac gcc atc cac cgg gac      1152
Pro Ser Gly Thr Met Leu Met Val Asn Ala Tyr Ala Ile His Arg Asp
    370             375             380 ccg gcg gcg tgg gag cgg ccg ctg gag ttc gtc ccg gag cgg ttc gag      1200
Pro Ala Ala Trp Glu Arg Pro Leu Glu Phe Val Pro Glu Arg Phe Glu
385             390             395             400 aac ggg aag gcc gag ggg cgg ttc atg atc ccg ttc ggg atg ggc cgg      1248
Asn Gly Lys Ala Glu Gly Arg Phe Met Ile Pro Phe Gly Met Gly Arg
            405             410             415 cgg cgg tgc ccc ggg gag acg ctg gcg ctg cgg acc att ggc atg gtg      1296
Arg Arg Cys Pro Gly Glu Thr Leu Ala Leu Arg Thr Ile Gly Met Val
            420             425             430 ctg gcc acg ctg gtg cag tgc ttc gac tgg gag cgc gtg gac ggc gcg      1344
Leu Ala Thr Leu Val Gln Cys Phe Asp Trp Glu Arg Val Asp Gly Ala
        435             440             445 gag gtg gac atg acg gag ggc gga ggg ctc acc atc ccc aag gtc gtg      1392
Glu Val Asp Met Thr Glu Gly Gly Gly Leu Thr Ile Pro Lys Val Val
        450             455             460 ccg ctc gag gcc gtg tgc agg ccg cgc ccg gcc atg cgc gac gtg ctt      1440
Pro Leu Glu Ala Val Cys Arg Pro Arg Pro Ala Met Arg Asp Val Leu
465             470             475             480 cag agc ctc tga                                                       1452
Gln Ser Leu
```

<210> SEQ ID NO 4
<211> LENGTH: 483
<212> TYPE: PRT
<213> ORGANISM: Triticum aestivum

<400> SEQUENCE: 4

```
Leu Pro Pro Ser Pro Gln Ala Ile Pro Phe Leu Gly His Leu His Leu
1               5                   10                  15

Leu Glu Lys Pro Phe His Ala Ala Leu Cys Arg Leu Ala Glu Arg Leu
                20                  25                  30

Gly Pro Val Phe Ser Leu Arg Leu Gly Ser Arg Arg Ala Val Val Val
            35                  40                  45

Ser Ser Ala Glu Cys Ala Arg Glu Cys Phe Thr Glu His Asp Val Ile
        50                  55                  60

Phe Ala Asp Arg Pro Gln Phe Pro Ser Gln Leu Leu Val Ser Phe Asp
65                  70                  75                  80

Gly Ile Ala Leu Ser Thr Ser Ser Tyr Gly Pro His Trp Arg Asn Leu
                85                  90                  95

Arg Arg Val Ala Ala Val Gln Leu Leu Ser Ala His Arg Val Ala Cys
            100                 105                 110

Met Ser Gly Val Ile Gly Gly Glu Val Arg Ala Met Ala Arg Arg Leu
        115                 120                 125

Phe Arg Ala Ala Ala Ala Ser Pro Gly Gly Asp Gly Ala Ala Arg Val
        130                 135                 140

Gln Leu Lys Arg Arg Leu Phe Glu Leu Ser Leu Ser Val Leu Met Glu
145                 150                 155                 160

Thr Ile Ala Gln Thr Lys Ala Thr Arg Ser Glu Ala Asp Ala Asp Thr
                165                 170                 175

Asp Met Ser Glu Glu Ala Gln Glu Phe Lys Lys Val Val Asp Glu Leu
            180                 185                 190
```

```
Ile Pro Tyr Leu Gly Ala Ala Asn Thr Trp Asp Tyr Leu Pro Val Leu
        195                 200                 205

Arg Trp Phe Asp Val Phe Gly Val Arg Asn Lys Ile Leu Ala Ala Val
    210                 215                 220

Ser Arg Arg Asp Ala Phe Leu His Arg Leu Ile Asp Asn Glu Arg Arg
225                 230                 235                 240

Arg Leu Asp Asn Ala Gly Thr Glu Gly Asp Lys Lys Ser Met Ile Ala
                245                 250                 255

Val Leu Leu Asn Leu Gln Lys Thr Glu Pro Glu Val Tyr Thr Asp Thr
                260                 265                 270

Met Ile Thr Ala Leu Cys Ala Asn Leu Phe Gly Ala Gly Thr Glu Thr
        275                 280                 285

Thr Ser Thr Thr Thr Glu Trp Ala Met Ser Leu Leu Leu Asn His Pro
    290                 295                 300

Ala Ala Leu Arg Lys Ala Gln Ala Glu Ile Asp Ala Ala Val Gly Thr
305                 310                 315                 320

Ser Arg Leu Val Thr Ala Asp Asp Val Pro Arg Leu Ala Tyr Leu Gln
                325                 330                 335

Cys Ile Val Ser Glu Thr Leu Arg Leu Tyr Pro Ala Ala Pro Met Leu
                340                 345                 350

Leu Pro His Gln Ser Ser Ala Asp Cys Lys Val Gly Gly Tyr Asn Val
        355                 360                 365

Pro Ser Gly Thr Met Leu Met Val Asn Ala Tyr Ala Ile His Arg Asp
    370                 375                 380

Pro Ala Ala Trp Glu Arg Pro Leu Glu Phe Val Pro Glu Arg Phe Glu
385                 390                 395                 400

Asn Gly Lys Ala Glu Gly Arg Phe Met Ile Pro Phe Gly Met Gly Arg
                405                 410                 415

Arg Arg Cys Pro Gly Glu Thr Leu Ala Leu Arg Thr Ile Gly Met Val
                420                 425                 430

Leu Ala Thr Leu Val Gln Cys Phe Asp Trp Glu Arg Val Asp Gly Ala
        435                 440                 445

Glu Val Asp Met Thr Glu Gly Gly Gly Leu Thr Ile Pro Lys Val Val
    450                 455                 460

Pro Leu Glu Ala Val Cys Arg Pro Arg Pro Ala Met Arg Asp Val Leu
465                 470                 475                 480

Gln Ser Leu
```

```
<210> SEQ ID NO 5
<211> LENGTH: 1446
<212> TYPE: DNA
<213> ORGANISM: Hordeum vulgare
<220> FEATURE:
<221> NAME/KEY: CDS
<222> LOCATION: (1)..(1446)

<400> SEQUENCE: 5 ctg ccg ccg agc ccc ccg gcc gtc ccg ttc ttc ggc cac ctc cac ctc      48
Leu Pro Pro Ser Pro Pro Ala Val Pro Phe Phe Gly His Leu His Leu
1               5                   10                  15 gtg gag aag ccg ttg cac gcc gca ctg tgc cgc ctc ggg gcg cgc cat      96
Val Glu Lys Pro Leu His Ala Ala Leu Cys Arg Leu Gly Ala Arg His
                20                  25                  30 ggg ccg gtc ttc tcg ctt cgg ctc ggc gcg cgc aac gcc gtg gtg gtg     144
Gly Pro Val Phe Ser Leu Arg Leu Gly Ala Arg Asn Ala Val Val Val
            35                  40                  45
```

```
tcc tcg ccg gcg tgc gcc agg gag tgc ttc acg gac cac gac gtg gcc        192
Ser Ser Pro Ala Cys Ala Arg Glu Cys Phe Thr Asp His Asp Val Ala
    50              55                  60 ttc gcc aac cgg ccc cag ttc ccc tcg cag atg ctc gtg tcc tac ggc        240
Phe Ala Asn Arg Pro Gln Phe Pro Ser Gln Met Leu Val Ser Tyr Gly
65              70                  75                  80 ggc acc tcg ctc gtc agc tcc agc tac ggc ccg cac tgg cgc aac ctc        288
Gly Thr Ser Leu Val Ser Ser Ser Tyr Gly Pro His Trp Arg Asn Leu
                85                  90                  95 cgc cgc gtc gcc gcc gtg cgc ctg ctc tcc gcg cat cgc gtc gcc ggc        336
Arg Arg Val Ala Ala Val Arg Leu Leu Ser Ala His Arg Val Ala Gly
                100                 105                 110 atg tcg ggc gtc atc gcc gcc gag gtg cgc gcc atg gcg cgc cgt ctg        384
Met Ser Gly Val Ile Ala Ala Glu Val Arg Ala Met Ala Arg Arg Leu
        115                 120                 125 tac cgc gcc gcc gcg gcg tcc ccc ggc ggc gcc gcg cgc gtg gag ctc        432
Tyr Arg Ala Ala Ala Ala Ser Pro Gly Gly Ala Ala Arg Val Glu Leu
    130                 135                 140 aag cgg agc ctg ttc gag ctc tcc ctg agc gtg ctc atg gag act atc        480
Lys Arg Ser Leu Phe Glu Leu Ser Leu Ser Val Leu Met Glu Thr Ile
145                 150                 155                 160 gcg cgg acc aag ggc acc cgc tcg gag gcg gac gcc gac acg gac atg        528
Ala Arg Thr Lys Gly Thr Arg Ser Glu Ala Asp Ala Asp Thr Asp Met
                165                 170                 175 tcg ctg gag gcg cag gag ttc aag cag gtg gtg gac gag atc atc ccg        576
Ser Leu Glu Ala Gln Glu Phe Lys Gln Val Val Asp Glu Ile Ile Pro
            180                 185                 190 ctc atc ggc gcg gcc aac ctg tgg gac tac ctg ccg gtg atg cgg tgg        624
Leu Ile Gly Ala Ala Asn Leu Trp Asp Tyr Leu Pro Val Met Arg Trp
            195                 200                 205 ttc gac gtg tcc ggc gtg agg agc agg atc ctg gcc acg gtg agc agg        672
Phe Asp Val Ser Gly Val Arg Ser Arg Ile Leu Ala Thr Val Ser Arg
    210                 215                 220 agg gac gcc ttc ctc cac cgg ctc att gac gcc gag cgg cgg agg atg        720
Arg Asp Ala Phe Leu His Arg Leu Ile Asp Ala Glu Arg Arg Arg Met
225                 230                 235                 240 gaa gag ggc ggc gac gag ggc gag aag aag agc atg att gcc gtg ctc        768
Glu Glu Gly Gly Asp Glu Gly Glu Lys Lys Ser Met Ile Ala Val Leu
                245                 250                 255 ctc act ctg caa aag acg gag ccg gag ctg tac act gat cag atg atc        816
Leu Thr Leu Gln Lys Thr Glu Pro Glu Leu Tyr Thr Asp Gln Met Ile
            260                 265                 270 atc gct ctg tgt gcg aat atg ttt gtg gcc gga aca gag acc acc tca        864
Ile Ala Leu Cys Ala Asn Met Phe Val Ala Gly Thr Glu Thr Thr Ser
            275                 280                 285 acc acg ata gaa tgg gcg atg tcg ctg ctg ctg aac cac ccg gcg gcg        912
Thr Thr Ile Glu Trp Ala Met Ser Leu Leu Leu Asn His Pro Ala Ala
    290                 295                 300 ctc aag aag gcc cag gcc gag atc gac gcg tcc atc ggg acc tcc cgc        960
Leu Lys Lys Ala Gln Ala Glu Ile Asp Ala Ser Ile Gly Thr Ser Arg
305                 310                 315                 320 atg gtt gcc gcc gac gac gtg ccc cgc ctc agc tac ctc cag tgc atc       1008
Met Val Ala Ala Asp Asp Val Pro Arg Leu Ser Tyr Leu Gln Cys Ile
                325                 330                 335 atc aac gag acg cta cgc atg tac ccg gcg gcg ccg ctg ctg ctg ccg       1056
Ile Asn Glu Thr Leu Arg Met Tyr Pro Ala Ala Pro Leu Leu Leu Pro
            340                 345                 350 cac gag tcc tcc gcc gac tgc aag gtc ggc ggc tac gac gtg ccg agc       1104
His Glu Ser Ser Ala Asp Cys Lys Val Gly Gly Tyr Asp Val Pro Ser
            355                 360                 365
```

-continued

```
ggc acc atg ctg atc gtg aac gcg tac gcc atc cac agg gac ccg gcg   1152
Gly Thr Met Leu Ile Val Asn Ala Tyr Ala Ile His Arg Asp Pro Ala
    370             375             380 acg tgg gag gac ccg acg gcg ttc cgg ccg gag cgg ttc gag gac ggc   1200
Thr Trp Glu Asp Pro Thr Ala Phe Arg Pro Glu Arg Phe Glu Asp Gly
385             390             395             400 aag ggc gac ggg ctg ctg ctg atg ccg ttc ggg atg ggg cgg cgg agg   1248
Lys Gly Asp Gly Leu Leu Leu Met Pro Phe Gly Met Gly Arg Arg Arg
            405             410             415 tgc ccc ggc gag gcg ctg gcg ctg cag acg gtc ggg gtt gtt ctc ggg   1296
Cys Pro Gly Glu Ala Leu Ala Leu Gln Thr Val Gly Val Val Leu Gly
            420             425             430 atg ctg gtg cag tgc ttc gac tgg gat cgg gtg gac ggc gtg gag gtg   1344
Met Leu Val Gln Cys Phe Asp Trp Asp Arg Val Asp Gly Val Glu Val
            435             440             445 gac atg acg gag ggg gtg ggg atc acc atg ccc aag tcc gtg gct ttg   1392
Asp Met Thr Glu Gly Val Gly Ile Thr Met Pro Lys Ser Val Ala Leu
            450             455             460 gag gcc gtg tgt agg ccg cgt gct gcc atg cgc gat gtc ctt cac aag   1440
Glu Ala Val Cys Arg Pro Arg Ala Ala Met Arg Asp Val Leu His Lys
465             470             475             480 ctg tga                                                            1446
Leu
```

```
<210> SEQ ID NO 6
<211> LENGTH: 481
<212> TYPE: PRT
<213> ORGANISM: Hordeum vulgare

<400> SEQUENCE: 6

Leu Pro Pro Ser Pro Pro Ala Val Pro Phe Phe Gly His Leu His Leu
1               5                   10                  15

Val Glu Lys Pro Leu His Ala Ala Leu Cys Arg Leu Gly Ala Arg His
                20                  25                  30

Gly Pro Val Phe Ser Leu Arg Leu Gly Ala Arg Asn Ala Val Val Val
            35                  40                  45

Ser Ser Pro Ala Cys Ala Arg Glu Cys Phe Thr Asp His Asp Val Ala
    50                  55                  60

Phe Ala Asn Arg Pro Gln Phe Pro Ser Gln Met Leu Val Ser Tyr Gly
65                  70                  75                  80

Gly Thr Ser Leu Val Ser Ser Ser Tyr Gly Pro His Trp Arg Asn Leu
                85                  90                  95

Arg Arg Val Ala Ala Val Arg Leu Leu Ser Ala His Arg Val Ala Gly
            100                 105                 110

Met Ser Gly Val Ile Ala Ala Glu Val Arg Ala Met Ala Arg Arg Leu
        115                 120                 125

Tyr Arg Ala Ala Ala Ala Ser Pro Gly Gly Ala Ala Arg Val Glu Leu
    130                 135                 140

Lys Arg Ser Leu Phe Glu Leu Ser Leu Ser Val Leu Met Glu Thr Ile
145                 150                 155                 160

Ala Arg Thr Lys Gly Thr Arg Ser Glu Ala Asp Ala Asp Thr Asp Met
                165                 170                 175

Ser Leu Glu Ala Gln Glu Phe Lys Gln Val Val Asp Glu Ile Ile Pro
            180                 185                 190

Leu Ile Gly Ala Ala Asn Leu Trp Asp Tyr Leu Pro Val Met Arg Trp
            195                 200                 205
```

-continued

```
Phe Asp Val Ser Gly Val Arg Ser Arg Ile Leu Ala Thr Val Ser Arg
    210             215                 220

Arg Asp Ala Phe Leu His Arg Leu Ile Asp Ala Glu Arg Arg Arg Met
225             230                 235                 240

Glu Glu Gly Gly Asp Glu Gly Glu Lys Lys Ser Met Ile Ala Val Leu
                245                 250                 255

Leu Thr Leu Gln Lys Thr Glu Pro Glu Leu Tyr Thr Asp Gln Met Ile
                260                 265                 270

Ile Ala Leu Cys Ala Asn Met Phe Val Ala Gly Thr Glu Thr Thr Ser
                275                 280                 285

Thr Thr Ile Glu Trp Ala Met Ser Leu Leu Leu Asn His Pro Ala Ala
    290                 295                 300

Leu Lys Lys Ala Gln Ala Glu Ile Asp Ala Ser Ile Gly Thr Ser Arg
305             310                 315                 320

Met Val Ala Ala Asp Asp Val Pro Arg Leu Ser Tyr Leu Gln Cys Ile
                325                 330                 335

Ile Asn Glu Thr Leu Arg Met Tyr Pro Ala Ala Pro Leu Leu Leu Pro
                340                 345                 350

His Glu Ser Ser Ala Asp Cys Lys Val Gly Gly Tyr Asp Val Pro Ser
                355                 360                 365

Gly Thr Met Leu Ile Val Asn Ala Tyr Ala Ile His Arg Asp Pro Ala
    370                 375                 380

Thr Trp Glu Asp Pro Thr Ala Phe Arg Pro Glu Arg Phe Glu Asp Gly
385                 390                 395                 400

Lys Gly Asp Gly Leu Leu Leu Met Pro Phe Gly Met Gly Arg Arg Arg
                405                 410                 415

Cys Pro Gly Glu Ala Leu Ala Leu Gln Thr Val Gly Val Val Leu Gly
                420                 425                 430

Met Leu Val Gln Cys Phe Asp Trp Asp Arg Val Asp Gly Val Glu Val
    435                 440                 445

Asp Met Thr Glu Gly Val Gly Ile Thr Met Pro Lys Ser Val Ala Leu
    450                 455                 460

Glu Ala Val Cys Arg Pro Arg Ala Ala Met Arg Asp Val Leu His Lys
465                 470                 475                 480

Leu
```

<210> SEQ ID NO 7
<211> LENGTH: 1452
<212> TYPE: DNA
<213> ORGANISM: Hordeum vulgare
<220> FEATURE:
<221> NAME/KEY: CDS
<222> LOCATION: (1)..(1452)

<400> SEQUENCE: 7

```
ctg ccg ccg agc ccc agg ccc atc ccg ttc ctc ggc cac ctc cac ctc      48
Leu Pro Pro Ser Pro Arg Pro Ile Pro Phe Leu Gly His Leu His Leu
1               5                   10                  15 ctg gag aag ccg ttc cac gtc gct ctg tgc cgc ctc gcc gcg cgc ctc      96
Leu Glu Lys Pro Phe His Val Ala Leu Cys Arg Leu Ala Ala Arg Leu
                20                  25                  30 ggc ccg gtc ttc tcg ctg cgg ctc ggc tcg cgc cgc gcc gtg gtg gtg     144
Gly Pro Val Phe Ser Leu Arg Leu Gly Ser Arg Arg Ala Val Val Val
                35                  40                  45 tcc tcg gcg gac tgc gcc agg gag tgc ttc acg gag cac gac gtg atc     192
Ser Ser Ala Asp Cys Ala Arg Glu Cys Phe Thr Glu His Asp Val Ile
    50                  55                  60
```

-continued

```
ttc gcc aac agg ccc cag ttc ccc tcg cag ctg ctc gtg tcc ttc gac        240
Phe Ala Asn Arg Pro Gln Phe Pro Ser Gln Leu Leu Val Ser Phe Asp
65                  70                  75                  80 ggc acc gcg ctc tcc acg tcc agc tac ggc ccg cac tgg cgc aac ctc        288
Gly Thr Ala Leu Ser Thr Ser Ser Tyr Gly Pro His Trp Arg Asn Leu
                85                  90                  95 cgt cgc gtc gcc gcc gtg cag ctg ctc tcc gcg cac cgc gtc gcc tgc        336
Arg Arg Val Ala Ala Val Gln Leu Leu Ser Ala His Arg Val Ala Cys
                100                 105                 110 atg tcc ggc gtc atc gcc ggc gag gtg cgc gcc atg gcc cgc cgg ctc        384
Met Ser Gly Val Ile Ala Gly Glu Val Arg Ala Met Ala Arg Arg Leu
                115                 120                 125 ttc cgc tcc gcc gag gcg tcc ccc ggc ggc ggt ggc gcc gcg cgg gtc        432
Phe Arg Ser Ala Glu Ala Ser Pro Gly Gly Gly Gly Ala Ala Arg Val
            130                 135                 140 cag ctg aag cgg agg ctg ttc gag ctc tca ttg agc gtg ctc atg gag        480
Gln Leu Lys Arg Arg Leu Phe Glu Leu Ser Leu Ser Val Leu Met Glu
145                 150                 155                 160 acc atc gct cag acc aag ggg acc cgg tcg gag gcc gac gcc gac acg        528
Thr Ile Ala Gln Thr Lys Gly Thr Arg Ser Glu Ala Asp Ala Asp Thr
                165                 170                 175 gac atg tcc gtg gag gcc cag gag ttc aag aag gtg gtg gac gag atc        576
Asp Met Ser Val Glu Ala Gln Glu Phe Lys Lys Val Val Asp Glu Ile
                180                 185                 190 atc ccg tac ctc ggc gcc gcc aac acg tgg gac tac ctg ccg gtg gtg        624
Ile Pro Tyr Leu Gly Ala Ala Asn Thr Trp Asp Tyr Leu Pro Val Val
                195                 200                 205 cgg tgg ttc gac gtg ttc ggc gtc agg aac aag atc ctg gcc gcc gtg        672
Arg Trp Phe Asp Val Phe Gly Val Arg Asn Lys Ile Leu Ala Ala Val
            210                 215                 220 agc agg agg gac gcc ttc ctc cat cgt ctc atc gac gcc gag cgg agg        720
Ser Arg Arg Asp Ala Phe Leu His Arg Leu Ile Asp Ala Glu Arg Arg
225                 230                 235                 240 agg ctg gac ggc ggc ggc gcc gaa gcc gac aag aag agc atg atc gcc        768
Arg Leu Asp Gly Gly Gly Ala Glu Ala Asp Lys Lys Ser Met Ile Ala
                245                 250                 255 gtg ctg ctc act ctg cag aag acg gag ccg gag gtg tac acc gat act        816
Val Leu Leu Thr Leu Gln Lys Thr Glu Pro Glu Val Tyr Thr Asp Thr
                260                 265                 270 atg atc acg gct ctc tgc tcg aat tta ttt ggg gcc gga acg gag acc        864
Met Ile Thr Ala Leu Cys Ser Asn Leu Phe Gly Ala Gly Thr Glu Thr
                275                 280                 285 acg tcg acg acg acg gag tgg gcc atg tcg ctg ctt ctg aac cac ccg        912
Thr Ser Thr Thr Thr Glu Trp Ala Met Ser Leu Leu Leu Asn His Pro
                290                 295                 300 gcg gcg ctg agg aag gcg cag gcc gag atc gac gcg gcc gtg ggc acc        960
Ala Ala Leu Arg Lys Ala Gln Ala Glu Ile Asp Ala Ala Val Gly Thr
305                 310                 315                 320 tcc cgg ctg gtg acc gcc gac gac gtg ccc cgg ctc gcc tac ctg cag       1008
Ser Arg Leu Val Thr Ala Asp Asp Val Pro Arg Leu Ala Tyr Leu Gln
                325                 330                 335 tgc atc gtg agc gag acg ctg cgg ctg tac ccg gcg acg ccg atg ctg       1056
Cys Ile Val Ser Glu Thr Leu Arg Leu Tyr Pro Ala Thr Pro Met Leu
                340                 345                 350 ctg ccg cac caa tcg tcg gcg gac tgc aag gtg ggc ggc tac aac gtg       1104
Leu Pro His Gln Ser Ser Ala Asp Cys Lys Val Gly Gly Tyr Asn Val
                355                 360                 365 ccg agc ggc acg atg ctg atg gtg aac gcg tac gcc atc cac cgc gac       1152
Pro Ser Gly Thr Met Leu Met Val Asn Ala Tyr Ala Ile His Arg Asp
```

-continued

```
          370              375              380 ccg gcg gcg tgg gag cgg ccg ctg gag ttc gtc ccg gag cgg ttc gag    1200
Pro Ala Ala Trp Glu Arg Pro Leu Glu Phe Val Pro Glu Arg Phe Glu
385              390              395              400 gac ggc aag gcc gag ggg cgg ttc atg atc ccg ttc ggg atg ggc cgc    1248
Asp Gly Lys Ala Glu Gly Arg Phe Met Ile Pro Phe Gly Met Gly Arg
             405              410              415 cgg cgg tgc ccc ggg gag acg ctg gcg ctg cgg acc atc ggc atg gtg    1296
Arg Arg Cys Pro Gly Glu Thr Leu Ala Leu Arg Thr Ile Gly Met Val
             420              425              430 ctg gcc acg ctg gtg cag tgc ttc gac tgg gac cgc gtc gac ggc aag    1344
Leu Ala Thr Leu Val Gln Cys Phe Asp Trp Asp Arg Val Asp Gly Lys
             435              440              445 gag gtg gac atg acg gag agc ggc ggg ctc acc atc ccc aag gcc gtg    1392
Glu Val Asp Met Thr Glu Ser Gly Gly Leu Thr Ile Pro Lys Ala Val
450              455              460 ccg ctc gag gcc gtc tgc agg ccg cgc gcg gcc atg cgc gac gtg ctc    1440
Pro Leu Glu Ala Val Cys Arg Pro Arg Ala Ala Met Arg Asp Val Leu
465              470              475              480 cag agc ctc tga                                                     1452
Gln Ser Leu
```

```
<210> SEQ ID NO 8
<211> LENGTH: 483
<212> TYPE: PRT
<213> ORGANISM: Hordeum vulgare

<400> SEQUENCE: 8

Leu Pro Pro Ser Pro Arg Pro Ile Pro Phe Leu Gly His Leu His Leu
1               5                   10                  15

Leu Glu Lys Pro Phe His Val Ala Leu Cys Arg Leu Ala Ala Arg Leu
            20                  25                  30

Gly Pro Val Phe Ser Leu Arg Leu Gly Ser Arg Arg Ala Val Val Val
            35                  40                  45

Ser Ser Ala Asp Cys Ala Arg Glu Cys Phe Thr Glu His Asp Val Ile
        50                  55                  60

Phe Ala Asn Arg Pro Gln Phe Pro Ser Gln Leu Leu Val Ser Phe Asp
65                  70                  75                  80

Gly Thr Ala Leu Ser Thr Ser Ser Tyr Gly Pro His Trp Arg Asn Leu
                85                  90                  95

Arg Arg Val Ala Ala Val Gln Leu Leu Ser Ala His Arg Val Ala Cys
            100                 105                 110

Met Ser Gly Val Ile Ala Gly Glu Val Arg Ala Met Ala Arg Arg Leu
            115                 120                 125

Phe Arg Ser Ala Glu Ala Ser Pro Gly Gly Gly Gly Ala Ala Arg Val
            130                 135                 140

Gln Leu Lys Arg Arg Leu Phe Glu Leu Ser Leu Ser Val Leu Met Glu
145                 150                 155                 160

Thr Ile Ala Gln Thr Lys Gly Thr Arg Ser Glu Ala Asp Ala Asp Thr
                165                 170                 175

Asp Met Ser Val Glu Ala Gln Glu Phe Lys Lys Val Val Asp Glu Ile
            180                 185                 190

Ile Pro Tyr Leu Gly Ala Ala Asn Thr Trp Asp Tyr Leu Pro Val Val
            195                 200                 205

Arg Trp Phe Asp Val Phe Gly Val Arg Asn Lys Ile Leu Ala Ala Val
            210                 215                 220
```

-continued

```
Ser Arg Arg Asp Ala Phe Leu His Arg Leu Ile Asp Ala Glu Arg Arg
225                 230                 235                 240

Arg Leu Asp Gly Gly Gly Ala Glu Ala Asp Lys Lys Ser Met Ile Ala
                245                 250                 255

Val Leu Leu Thr Leu Gln Lys Thr Glu Pro Glu Val Tyr Thr Asp Thr
                260                 265                 270

Met Ile Thr Ala Leu Cys Ser Asn Leu Phe Gly Ala Gly Thr Glu Thr
                275                 280                 285

Thr Ser Thr Thr Thr Glu Trp Ala Met Ser Leu Leu Leu Asn His Pro
                290                 295                 300

Ala Ala Leu Arg Lys Ala Gln Ala Glu Ile Asp Ala Ala Val Gly Thr
305                 310                 315                 320

Ser Arg Leu Val Thr Ala Asp Asp Val Pro Arg Leu Ala Tyr Leu Gln
                325                 330                 335

Cys Ile Val Ser Glu Thr Leu Arg Leu Tyr Pro Ala Thr Pro Met Leu
                340                 345                 350

Leu Pro His Gln Ser Ser Ala Asp Cys Lys Val Gly Gly Tyr Asn Val
                355                 360                 365

Pro Ser Gly Thr Met Leu Met Val Asn Ala Tyr Ala Ile His Arg Asp
                370                 375                 380

Pro Ala Ala Trp Glu Arg Pro Leu Glu Phe Val Pro Glu Arg Phe Glu
385                 390                 395                 400

Asp Gly Lys Ala Glu Gly Arg Phe Met Ile Pro Phe Gly Met Gly Arg
                405                 410                 415

Arg Arg Cys Pro Gly Glu Thr Leu Ala Leu Arg Thr Ile Gly Met Val
                420                 425                 430

Leu Ala Thr Leu Val Gln Cys Phe Asp Trp Asp Arg Val Asp Gly Lys
                435                 440                 445

Glu Val Asp Met Thr Glu Ser Gly Gly Leu Thr Ile Pro Lys Ala Val
                450                 455                 460

Pro Leu Glu Ala Val Cys Arg Pro Arg Ala Ala Met Arg Asp Val Leu
465                 470                 475                 480

Gln Ser Leu
```

```
<210> SEQ ID NO 9
<211> LENGTH: 1551
<212> TYPE: DNA
<213> ORGANISM: Triticum aestivum
<220> FEATURE:
<221> NAME/KEY: CDS
<222> LOCATION: (1)..(1551)

<400> SEQUENCE: 9 atg gat aag gcg tac att gcc atc ctc acc atc gcc ttc ctc ttc ctg      48
Met Asp Lys Ala Tyr Ile Ala Ile Leu Thr Ile Ala Phe Leu Phe Leu
1                   5                   10                  15 atc cac tac gtt ctg ggc aat ggc cgg cgc ggc ggc aag ggc gcc gcg      96
Ile His Tyr Val Leu Gly Asn Gly Arg Arg Gly Gly Lys Gly Ala Ala
                20                  25                  30 cag ctg ccg ccg agc ccc ccg gcc atc ccg ttc ctc ggc cac ctc cac     144
Gln Leu Pro Pro Ser Pro Pro Ala Ile Pro Phe Leu Gly His Leu His
            35                  40                  45 ctc ctg gag aag ccg ttc cat gcc gcg ctg cgc cgc ctc gcc gcg cgc     192
Leu Leu Glu Lys Pro Phe His Ala Ala Leu Arg Arg Leu Ala Ala Arg
        50                  55                  60 ctc ggc ccg gtc ttc tcg ctg cgg ctc ggc tcg cgc cgc gcc gtt gtg     240
Leu Gly Pro Val Phe Ser Leu Arg Leu Gly Ser Arg Arg Ala Val Val
```

-continued

```
65                      70                      75                      80 gtc tcc tcg gcg gag tgc gcc agg gag tgc ttc acg gag cac gac gtg      288
Val Ser Ser Ala Glu Cys Ala Arg Glu Cys Phe Thr Glu His Asp Val
                85                      90                      95 acg ttc gcc aac cgg ccc cgg ttc ccc tcg cag ctg ctc gtc tcc ttc      336
Thr Phe Ala Asn Arg Pro Arg Phe Pro Ser Gln Leu Leu Val Ser Phe
            100                     105                     110 gac ggc gcc gcg ctc gtc acg tcc agc tac ggc ccg cac tgg cgc aac      384
Asp Gly Ala Ala Leu Val Thr Ser Ser Tyr Gly Pro His Trp Arg Asn
            115                     120                     125 ctc cgc cgc gtc gcc gcc gtg cag ctg ctc tcc gcg cac cgc gtc gcc      432
Leu Arg Arg Val Ala Ala Val Gln Leu Leu Ser Ala His Arg Val Ala
            130                     135                     140 tgc atg tct ggc gtc atc gcc ggc gag gtg cgc gcc atg gcg cgc cgg      480
Cys Met Ser Gly Val Ile Ala Gly Glu Val Arg Ala Met Ala Arg Arg
145                     150                     155                     160 ctg ttc cgc gcc gcc gcg gcg tcc ccc ggc ggc gat ggc gcc gcg cgg      528
Leu Phe Arg Ala Ala Ala Ala Ser Pro Gly Gly Asp Gly Ala Ala Arg
                165                     170                     175 gtc cag ctg aag cgg agg ctc ttc gag ctc tcc ctc agc gtg ctc atg      576
Val Gln Leu Lys Arg Arg Leu Phe Glu Leu Ser Leu Ser Val Leu Met
            180                     185                     190 gag acc atc gcc cag acc aag gcg acc cgg tcg gag gcc gac gcc gac      624
Glu Thr Ile Ala Gln Thr Lys Ala Thr Arg Ser Glu Ala Asp Ala Asp
            195                     200                     205 acg gac atg tcc gtg gag gcc cag gag ttc aag aag gtg gtg gac gag      672
Thr Asp Met Ser Val Glu Ala Gln Glu Phe Lys Lys Val Val Asp Glu
            210                     215                     220 ctc atc ccg tac ctc ggc gcc gcc aac acg tgg gat tac ctg ccg gtg      720
Leu Ile Pro Tyr Leu Gly Ala Ala Asn Thr Trp Asp Tyr Leu Pro Val
225                     230                     235                     240 ttg cgg tgg ttc gac gtg ttc ggc gtg agg aac aag atc ctg gcc gcc      768
Leu Arg Trp Phe Asp Val Phe Gly Val Arg Asn Lys Ile Leu Ala Ala
                245                     250                     255 gtg agc agg agg gac gcc ttc atg ctg cgt ctc atc gac aac gag cgc      816
Val Ser Arg Arg Asp Ala Phe Met Leu Arg Leu Ile Asp Asn Glu Arg
                260                     265                     270 cgg agg ctc gac gac gct ggc acc gaa ggc gac aag aag agc atg atc      864
Arg Arg Leu Asp Asp Ala Gly Thr Glu Gly Asp Lys Lys Ser Met Ile
            275                     280                     285 gcc gtg ctc ctc aat ctg cag aag acg gag ccg gag gtg tac gcc gat      912
Ala Val Leu Leu Asn Leu Gln Lys Thr Glu Pro Glu Val Tyr Ala Asp
            290                     295                     300 acc atg atc acg gct ctc tgc gcg aat tta ttt ggg gcc gga acg gag      960
Thr Met Ile Thr Ala Leu Cys Ala Asn Leu Phe Gly Ala Gly Thr Glu
305                     310                     315                     320 acc acg tcg acg acg acg gag tgg gcg atg tcg ctg ctg ctg aac cac     1008
Thr Thr Ser Thr Thr Thr Glu Trp Ala Met Ser Leu Leu Leu Asn His
                325                     330                     335 ccg gcg gcg ctc aaa aag gcg cag gcc gag atc gac gcg gcc gtg ggc     1056
Pro Ala Ala Leu Lys Lys Ala Gln Ala Glu Ile Asp Ala Ala Val Gly
            340                     345                     350 acc tcc cgg ctg gtg acc gcc gac gac gtg cca cgg ctg gcc tac ctg     1104
Thr Ser Arg Leu Val Thr Ala Asp Asp Val Pro Arg Leu Ala Tyr Leu
            355                     360                     365 cag tgc atc gtg agc gag acg ctg cgg ctg tat ccg gcg gcg ccg atg     1152
Gln Cys Ile Val Ser Glu Thr Leu Arg Leu Tyr Pro Ala Ala Pro Met
            370                     375                     380 ctg ctg ccg cac gag tcc tcg gca gac tgc aag gtg ggc ggc tac aac     1200
```

-continued

```
Leu Leu Pro His Glu Ser Ser Ala Asp Cys Lys Val Gly Gly Tyr Asn
385             390                 395                 400 gtg ccg agc ggc acg atg ctg atg gtg aac gcg tac gcc atc cac cgg        1248
Val Pro Ser Gly Thr Met Leu Met Val Asn Ala Tyr Ala Ile His Arg
                405                 410                 415 gac ccg gcg gcg tgg gag cgg ccg ctg gag ttc gtc ccg gag cgg ttc        1296
Asp Pro Ala Ala Trp Glu Arg Pro Leu Glu Phe Val Pro Glu Arg Phe
            420                 425                 430 gag gac ggg aag gcc gag ggg cgg ttc atg atc ccg ttc ggg atg ggc        1344
Glu Asp Gly Lys Ala Glu Gly Arg Phe Met Ile Pro Phe Gly Met Gly
        435                 440                 445 cgc cgg cgg tgc ccc ggg gag acg ctg gcg ctg cgg acc atc ggc atg        1392
Arg Arg Arg Cys Pro Gly Glu Thr Leu Ala Leu Arg Thr Ile Gly Met
    450                 455                 460 gtg ctg gcc acg ctg gtg cag tgc ttc gac tgg gag cgc gtc gac ggc        1440
Val Leu Ala Thr Leu Val Gln Cys Phe Asp Trp Glu Arg Val Asp Gly
465                 470                 475                 480 gcg gag gtg gac atg acg gag ggc ggc ggg ctc acc atc ccc aag gtc        1488
Ala Glu Val Asp Met Thr Glu Gly Gly Gly Leu Thr Ile Pro Lys Val
                485                 490                 495 gtg cca ctc gag gcc gtg tgc agg ccg cgc ccg gcc atg cgc gac gtg        1536
Val Pro Leu Glu Ala Val Cys Arg Pro Arg Pro Ala Met Arg Asp Val
            500                 505                 510 ctt cag agc ctc tga                                                     1551
Leu Gln Ser Leu
        515
```

```
<210> SEQ ID NO 10
<211> LENGTH: 516
<212> TYPE: PRT
<213> ORGANISM: Triticum aestivum

<400> SEQUENCE: 10

Met Asp Lys Ala Tyr Ile Ala Ile Leu Thr Ile Ala Phe Leu Phe Leu
1               5                   10                  15

Ile His Tyr Val Leu Gly Asn Gly Arg Arg Gly Gly Lys Gly Ala Ala
                20                  25                  30

Gln Leu Pro Pro Ser Pro Pro Ala Ile Pro Phe Leu Gly His Leu His
            35                  40                  45

Leu Leu Glu Lys Pro Phe His Ala Ala Leu Arg Arg Leu Ala Ala Arg
        50                  55                  60

Leu Gly Pro Val Phe Ser Leu Arg Leu Gly Ser Arg Arg Ala Val Val
65                  70                  75                  80

Val Ser Ser Ala Glu Cys Ala Arg Glu Cys Phe Thr Glu His Asp Val
                85                  90                  95

Thr Phe Ala Asn Arg Pro Arg Phe Pro Ser Gln Leu Leu Val Ser Phe
                100                 105                 110

Asp Gly Ala Ala Leu Val Thr Ser Ser Tyr Gly Pro His Trp Arg Asn
            115                 120                 125

Leu Arg Arg Val Ala Ala Val Gln Leu Leu Ser Ala His Arg Val Ala
        130                 135                 140

Cys Met Ser Gly Val Ile Ala Gly Glu Val Arg Ala Met Ala Arg Arg
145                 150                 155                 160

Leu Phe Arg Ala Ala Ala Ala Ser Pro Gly Gly Asp Gly Ala Ala Arg
                165                 170                 175

Val Gln Leu Lys Arg Arg Leu Phe Glu Leu Ser Leu Ser Val Leu Met
            180                 185                 190
```

```
Glu Thr Ile Ala Gln Thr Lys Ala Thr Arg Ser Glu Ala Asp Ala Asp
        195             200             205

Thr Asp Met Ser Val Glu Ala Gln Glu Phe Lys Lys Val Val Asp Glu
    210             215             220

Leu Ile Pro Tyr Leu Gly Ala Ala Asn Thr Trp Asp Tyr Leu Pro Val
225             230             235             240

Leu Arg Trp Phe Asp Val Phe Gly Val Arg Asn Lys Ile Leu Ala Ala
                245             250             255

Val Ser Arg Arg Asp Ala Phe Met Leu Arg Leu Ile Asp Asn Glu Arg
            260             265             270

Arg Arg Leu Asp Asp Ala Gly Thr Glu Gly Asp Lys Lys Ser Met Ile
        275             280             285

Ala Val Leu Leu Asn Leu Gln Lys Thr Glu Pro Glu Val Tyr Ala Asp
        290             295             300

Thr Met Ile Thr Ala Leu Cys Ala Asn Leu Phe Gly Ala Gly Thr Glu
305             310             315             320

Thr Thr Ser Thr Thr Thr Glu Trp Ala Met Ser Leu Leu Leu Asn His
                325             330             335

Pro Ala Ala Leu Lys Lys Ala Gln Ala Glu Ile Asp Ala Ala Val Gly
            340             345             350

Thr Ser Arg Leu Val Thr Ala Asp Asp Val Pro Arg Leu Ala Tyr Leu
        355             360             365

Gln Cys Ile Val Ser Glu Thr Leu Arg Leu Tyr Pro Ala Ala Pro Met
    370             375             380

Leu Leu Pro His Glu Ser Ser Ala Asp Cys Lys Val Gly Gly Tyr Asn
385             390             395             400

Val Pro Ser Gly Thr Met Leu Met Val Asn Ala Tyr Ala Ile His Arg
                405             410             415

Asp Pro Ala Ala Trp Glu Arg Pro Leu Glu Phe Val Pro Glu Arg Phe
            420             425             430

Glu Asp Gly Lys Ala Glu Gly Arg Phe Met Ile Pro Phe Gly Met Gly
        435             440             445

Arg Arg Arg Cys Pro Gly Glu Thr Leu Ala Leu Arg Thr Ile Gly Met
    450             455             460

Val Leu Ala Thr Leu Val Gln Cys Phe Asp Trp Glu Arg Val Asp Gly
465             470             475             480

Ala Glu Val Asp Met Thr Glu Gly Gly Gly Leu Thr Ile Pro Lys Val
                485             490             495

Val Pro Leu Glu Ala Val Cys Arg Pro Arg Pro Ala Met Arg Asp Val
            500             505             510

Leu Gln Ser Leu
        515

<210> SEQ ID NO 11
<211> LENGTH: 1557
<212> TYPE: DNA
<213> ORGANISM: Triticum aestivum
<220> FEATURE:
<221> NAME/KEY: CDS
<222> LOCATION: (1)..(1557)

<400> SEQUENCE: 11 atg gat aag gca tat atc gcc atc ctc tcc ttc gcc ttc ctc ttc ctg        48
Met Asp Lys Ala Tyr Ile Ala Ile Leu Ser Phe Ala Phe Leu Phe Leu
1               5                   10                  15 ctc cac tac att cta ggc aag gtc agc aat ggc agg cgc agc aag ggc        96
```

```
                Leu His Tyr Ile Leu Gly Lys Val Ser Asn Gly Arg Arg Ser Lys Gly
                             20                  25                  30 gcc gtc cag ctg ccg ccg agc ccc cag gcc atc ccg ttc ctc ggc cac                    144
Ala Val Gln Leu Pro Pro Ser Pro Gln Ala Ile Pro Phe Leu Gly His
             35                  40                  45 ctc cac ctc ctg gag aag ccg ttc cac gcc gct ctg tgc cgc ctc gcc                    192
Leu His Leu Leu Glu Lys Pro Phe His Ala Ala Leu Cys Arg Leu Ala
     50                  55                  60 gag cgc ctc ggc ccg gtc ttc tcg ctg cgc ctc ggc tcg cgc cgc gcc                    240
Glu Arg Leu Gly Pro Val Phe Ser Leu Arg Leu Gly Ser Arg Arg Ala
65                  70                  75                  80 gtg gtc gtc tcc tcg gcg gag tgc gcc agg gag tgc ttc acg gag cac                    288
Val Val Val Ser Ser Ala Glu Cys Ala Arg Glu Cys Phe Thr Glu His
                     85                  90                  95 gac gtg atc ttc gcc gac cgg ccc cag ttc ccc tcg cag ctg ctc gtg                    336
Asp Val Ile Phe Ala Asp Arg Pro Gln Phe Pro Ser Gln Leu Leu Val
             100                 105                 110 tcc ttc gac ggc atc gcg ctc tcc acg tcc agc tac ggc ccg cac tgg                    384
Ser Phe Asp Gly Ile Ala Leu Ser Thr Ser Ser Tyr Gly Pro His Trp
             115                 120                 125 cgc aac ctc cgc cgc gtc gcc gcc gtg cag ctg ctc tct gcg cac cgc                    432
Arg Asn Leu Arg Arg Val Ala Ala Val Gln Leu Leu Ser Ala His Arg
     130                 135                 140 gtc gcc tgc atg tcc ggc gtg atc ggg ggc gag gtg cgc gcc atg gcg                    480
Val Ala Cys Met Ser Gly Val Ile Gly Gly Glu Val Arg Ala Met Ala
145                 150                 155                 160 cgc cgg ctc ttc cgc gcc gcc gcg gcg tcc ccc ggt ggg gac ggc gcc                    528
Arg Arg Leu Phe Arg Ala Ala Ala Ala Ser Pro Gly Gly Asp Gly Ala
                     165                 170                 175 gcg cgg gtc cag ctg aag cgg agg ctc ttc gag ctc tcc ctc agc gtg                    576
Ala Arg Val Gln Leu Lys Arg Arg Leu Phe Glu Leu Ser Leu Ser Val
             180                 185                 190 ctc atg gaa acc atc gcc cag acc aag gcg acc cgg tcg gag gcc gac                    624
Leu Met Glu Thr Ile Ala Gln Thr Lys Ala Thr Arg Ser Glu Ala Asp
             195                 200                 205 gcc gac acg gac atg tca gag gag gcc cag gag ttc aag aag gtg gtg                    672
Ala Asp Thr Asp Met Ser Glu Glu Ala Gln Glu Phe Lys Lys Val Val
     210                 215                 220 gac gag ctc atc ccg tac ctc ggc gcc gcc aac acg tgg gat tac ctg                    720
Asp Glu Leu Ile Pro Tyr Leu Gly Ala Ala Asn Thr Trp Asp Tyr Leu
225                 230                 235                 240 ccg gtg ttg cgg tgg ttc gac gtg ttc ggc gtg agg aac aag atc ctg                    768
Pro Val Leu Arg Trp Phe Asp Val Phe Gly Val Arg Asn Lys Ile Leu
                     245                 250                 255 gcc gcc gtg agc agg agg gac gcc ttc ctg cat cgt ctc atc gac aac                    816
Ala Ala Val Ser Arg Arg Asp Ala Phe Leu His Arg Leu Ile Asp Asn
                     260                 265                 270 gag cgc cgg agg ctc gac aac gcc ggc acc gaa ggc gac aag aag agc                    864
Glu Arg Arg Arg Leu Asp Asn Ala Gly Thr Glu Gly Asp Lys Lys Ser
             275                 280                 285 atg atc gcc gtg ctc ctc aat ctg cag aag acg gag ccg gag gtg tac                    912
Met Ile Ala Val Leu Leu Asn Leu Gln Lys Thr Glu Pro Glu Val Tyr
             290                 295                 300 acc gat acc atg atc acg gct ctc tgc gcg aat tta ttc ggg gcc gga                    960
Thr Asp Thr Met Ile Thr Ala Leu Cys Ala Asn Leu Phe Gly Ala Gly
305                 310                 315                 320 acg gag acc acg tcg acg acg acg gag tgg gcg atg tcg ctg ctg ctg                   1008
Thr Glu Thr Thr Ser Thr Thr Thr Glu Trp Ala Met Ser Leu Leu Leu
                     325                 330                 335
```

-continued

```
aac cac ccg gcg gcg ctg agg aag gcg cag gcc gag atc gac gcg gcc    1056
Asn His Pro Ala Ala Leu Arg Lys Ala Gln Ala Glu Ile Asp Ala Ala
            340             345             350 gtg ggg acc tcc cgg ctg gtg acc gcc gac gac gtg ccc cgg ctg gcc    1104
Val Gly Thr Ser Arg Leu Val Thr Ala Asp Asp Val Pro Arg Leu Ala
            355             360             365 tac ctg cag tgc atc gtg agc gag acg ctg cgg ctg tac ccg gcg gcg    1152
Tyr Leu Gln Cys Ile Val Ser Glu Thr Leu Arg Leu Tyr Pro Ala Ala
        370             375             380 ccg atg ctg ctg ccg cac cag tcc tcg gcg gac tgc aag gtc ggc ggc    1200
Pro Met Leu Leu Pro His Gln Ser Ser Ala Asp Cys Lys Val Gly Gly
385             390             395             400 tac aac gtg ccg agc ggc acg atg ctg atg gtg aac gcg tac gcc atc    1248
Tyr Asn Val Pro Ser Gly Thr Met Leu Met Val Asn Ala Tyr Ala Ile
            405             410             415 cac cgg gac ccg gcg gcg tgg gag cgg ccg ctg gag ttc gtc ccg gag    1296
His Arg Asp Pro Ala Ala Trp Glu Arg Pro Leu Glu Phe Val Pro Glu
            420             425             430 cgg ttc gag aac ggg aag gcc gag ggg cgg ttc atg atc ccg ttc ggg    1344
Arg Phe Glu Asn Gly Lys Ala Glu Gly Arg Phe Met Ile Pro Phe Gly
            435             440             445 atg ggc cgg cgg cgg tgc ccc ggg gag acg ctg gcg ctg cgg acc att    1392
Met Gly Arg Arg Arg Cys Pro Gly Glu Thr Leu Ala Leu Arg Thr Ile
        450             455             460 ggc atg gtg ctg gcc acg ctg gtg cag tgc ttc gac tgg gag cgc gtg    1440
Gly Met Val Leu Ala Thr Leu Val Gln Cys Phe Asp Trp Glu Arg Val
465             470             475             480 gac ggc gcg gag gtg gac atg acg gag ggc gga ggg ctc acc atc ccc    1488
Asp Gly Ala Glu Val Asp Met Thr Glu Gly Gly Gly Leu Thr Ile Pro
            485             490             495 aag gtc gtg ccg ctc gag gcc gtg tgc agg ccg cgc ccg gcc atg cgc    1536
Lys Val Val Pro Leu Glu Ala Val Cys Arg Pro Arg Pro Ala Met Arg
            500             505             510 gac gtg ctt cag agc ctc tga                                        1557
Asp Val Leu Gln Ser Leu
            515
```

```
<210> SEQ ID NO 12
<211> LENGTH: 518
<212> TYPE: PRT
<213> ORGANISM: Triticum aestivum

<400> SEQUENCE: 12

Met Asp Lys Ala Tyr Ile Ala Ile Leu Ser Phe Ala Phe Leu Phe Leu
1               5               10              15

Leu His Tyr Ile Leu Gly Lys Val Ser Asn Gly Arg Arg Ser Lys Gly
            20              25              30

Ala Val Gln Leu Pro Pro Ser Pro Gln Ala Ile Pro Phe Leu Gly His
            35              40              45

Leu His Leu Leu Glu Lys Pro Phe His Ala Ala Leu Cys Arg Leu Ala
        50              55              60

Glu Arg Leu Gly Pro Val Phe Ser Leu Arg Leu Gly Ser Arg Arg Ala
65              70              75              80

Val Val Val Ser Ser Ala Glu Cys Ala Arg Glu Cys Phe Thr Glu His
                85              90              95

Asp Val Ile Phe Ala Asp Arg Pro Gln Phe Pro Ser Gln Leu Leu Val
            100             105             110

Ser Phe Asp Gly Ile Ala Leu Ser Thr Ser Ser Tyr Gly Pro His Trp
            115             120             125
```

-continued

```
Arg Asn Leu Arg Arg Val Ala Ala Val Gln Leu Leu Ser Ala His Arg
    130                 135                 140

Val Ala Cys Met Ser Gly Val Ile Gly Gly Glu Val Arg Ala Met Ala
145                 150                 155                 160

Arg Arg Leu Phe Arg Ala Ala Ala Ala Ser Pro Gly Gly Asp Gly Ala
                165                 170                 175

Ala Arg Val Gln Leu Lys Arg Arg Leu Phe Glu Leu Ser Leu Ser Val
                180                 185                 190

Leu Met Glu Thr Ile Ala Gln Thr Lys Ala Thr Arg Ser Glu Ala Asp
        195                 200                 205

Ala Asp Thr Asp Met Ser Glu Glu Ala Gln Glu Phe Lys Lys Val Val
    210                 215                 220

Asp Glu Leu Ile Pro Tyr Leu Gly Ala Ala Asn Thr Trp Asp Tyr Leu
225                 230                 235                 240

Pro Val Leu Arg Trp Phe Asp Val Phe Gly Val Arg Asn Lys Ile Leu
                245                 250                 255

Ala Ala Val Ser Arg Arg Asp Ala Phe Leu His Arg Leu Ile Asp Asn
                260                 265                 270

Glu Arg Arg Arg Leu Asp Asn Ala Gly Thr Glu Gly Asp Lys Lys Ser
        275                 280                 285

Met Ile Ala Val Leu Leu Asn Leu Gln Lys Thr Glu Pro Glu Val Tyr
    290                 295                 300

Thr Asp Thr Met Ile Thr Ala Leu Cys Ala Asn Leu Phe Gly Ala Gly
305                 310                 315                 320

Thr Glu Thr Thr Ser Thr Thr Thr Glu Trp Ala Met Ser Leu Leu Leu
                325                 330                 335

Asn His Pro Ala Ala Leu Arg Lys Ala Gln Ala Glu Ile Asp Ala Ala
                340                 345                 350

Val Gly Thr Ser Arg Leu Val Thr Ala Asp Asp Val Pro Arg Leu Ala
        355                 360                 365

Tyr Leu Gln Cys Ile Val Ser Glu Thr Leu Arg Leu Tyr Pro Ala Ala
    370                 375                 380

Pro Met Leu Leu Pro His Gln Ser Ser Ala Asp Cys Lys Val Gly Gly
385                 390                 395                 400

Tyr Asn Val Pro Ser Gly Thr Met Leu Met Val Asn Ala Tyr Ala Ile
                405                 410                 415

His Arg Asp Pro Ala Ala Trp Glu Arg Pro Leu Glu Phe Val Pro Glu
                420                 425                 430

Arg Phe Glu Asn Gly Lys Ala Glu Gly Arg Phe Met Ile Pro Phe Gly
        435                 440                 445

Met Gly Arg Arg Arg Cys Pro Gly Glu Thr Leu Ala Leu Arg Thr Ile
    450                 455                 460

Gly Met Val Leu Ala Thr Leu Val Gln Cys Phe Asp Trp Glu Arg Val
465                 470                 475                 480

Asp Gly Ala Glu Val Asp Met Thr Glu Gly Gly Gly Leu Thr Ile Pro
                485                 490                 495

Lys Val Val Pro Leu Glu Ala Val Cys Arg Pro Arg Pro Ala Met Arg
                500                 505                 510

Asp Val Leu Gln Ser Leu
        515
```

<210> SEQ ID NO 13
<211> LENGTH: 1557

-continued

```
<212> TYPE: DNA
<213> ORGANISM: Hordeum vulgare
<220> FEATURE:
<221> NAME/KEY: CDS
<222> LOCATION: (1)..(1557)

<400> SEQUENCE: 13 atg gat aag gca tcc att gcc gtc ctc tcc ttg gcc ttc ctc ttc ctg        48
Met Asp Lys Ala Ser Ile Ala Val Leu Ser Leu Ala Phe Leu Phe Leu
1               5                   10                  15 ctc cac tac att ctg ggc aag agg agc gat ggc agg cgc ggc aag ggc        96
Leu His Tyr Ile Leu Gly Lys Arg Ser Asp Gly Arg Arg Gly Lys Gly
            20                  25                  30 aag ggc gcc gtg cag ctg ccg ccg agc ccc ccg gcc gtc ccg ttc ttc       144
Lys Gly Ala Val Gln Leu Pro Pro Ser Pro Pro Ala Val Pro Phe Phe
        35                  40                  45 ggc cac ctc cac ctc gtg gag aag ccg ttg cac gcc gca ctg tgc cgc       192
Gly His Leu His Leu Val Glu Lys Pro Leu His Ala Ala Leu Cys Arg
    50                  55                  60 ctc ggg gcg cgc cat ggg ccg gtc ttc tcg ctt cgg ctc ggc gcg cgc       240
Leu Gly Ala Arg His Gly Pro Val Phe Ser Leu Arg Leu Gly Ala Arg
65                  70                  75                  80 aac gcc gtg gtg gtg tcc tcg ccg gcg tgc gcc agg gag tgc ttc acg       288
Asn Ala Val Val Val Ser Ser Pro Ala Cys Ala Arg Glu Cys Phe Thr
                85                  90                  95 gac cac gac gtg gcc ttc gcc aac cgg ccc cag ttc ccc tcg cag atg       336
Asp His Asp Val Ala Phe Ala Asn Arg Pro Gln Phe Pro Ser Gln Met
            100                 105                 110 ctc gtg tcc tac ggc ggc acc tcg ctc gtc agc tcc agc tac ggc ccg       384
Leu Val Ser Tyr Gly Gly Thr Ser Leu Val Ser Ser Ser Tyr Gly Pro
        115                 120                 125 cac tgg cgc aac ctc cgc cgc gtc gcc gcc gtg cgc ctg ctc tcc gcg       432
His Trp Arg Asn Leu Arg Arg Val Ala Ala Val Arg Leu Leu Ser Ala
    130                 135                 140 cat cgc gtc gcc ggc atg tcg ggc gtc atc gcc gcc gag gtg cgc gcc       480
His Arg Val Ala Gly Met Ser Gly Val Ile Ala Ala Glu Val Arg Ala
145                 150                 155                 160 atg gcg cgc cgt ctg tac cgc gcc gcc gcg gcg tcc ccc ggc ggc gcc       528
Met Ala Arg Arg Leu Tyr Arg Ala Ala Ala Ala Ser Pro Gly Gly Ala
                165                 170                 175 gcg cgc gtg gag ctc aag cgg agc ctg ttc gag ctc tcc ctg agc gtg       576
Ala Arg Val Glu Leu Lys Arg Ser Leu Phe Glu Leu Ser Leu Ser Val
            180                 185                 190 ctc atg gag act atc gcg cgg acc aag ggc acc cgc tcg gag gcg gac       624
Leu Met Glu Thr Ile Ala Arg Thr Lys Gly Thr Arg Ser Glu Ala Asp
        195                 200                 205 gcc gac acg gac atg tcg ctg gag gcg cag gag ttc aag cag gtg gtg       672
Ala Asp Thr Asp Met Ser Leu Glu Ala Gln Glu Phe Lys Gln Val Val
    210                 215                 220 gac gag atc atc ccg ctc atc ggc gcg gcc aac ctg tgg gac tac ctg       720
Asp Glu Ile Ile Pro Leu Ile Gly Ala Ala Asn Leu Trp Asp Tyr Leu
225                 230                 235                 240 ccg gtg atg cgg tgg ttc gac gtg tcc ggc gtg agg agc agg atc ctg       768
Pro Val Met Arg Trp Phe Asp Val Ser Gly Val Arg Ser Arg Ile Leu
                245                 250                 255 gcc acg gtg agc agg agg gac gcc ttc ctc cac cgg ctc att gac gcc       816
Ala Thr Val Ser Arg Arg Asp Ala Phe Leu His Arg Leu Ile Asp Ala
            260                 265                 270 gag cgg cgg agg atg gaa gag ggc ggc gac gag ggc gag aag aag agc       864
Glu Arg Arg Arg Met Glu Glu Gly Gly Asp Glu Gly Glu Lys Lys Ser
        275                 280                 285
```

-continued

```
atg att gcc gtg ctc ctc act ctg caa aag acg gag ccg gag ctg tac      912
Met Ile Ala Val Leu Leu Thr Leu Gln Lys Thr Glu Pro Glu Leu Tyr
    290             295             300 act gat cag atg atc atc gct ctg tgt gcg aat atg ttt gtg gcc gga      960
Thr Asp Gln Met Ile Ile Ala Leu Cys Ala Asn Met Phe Val Ala Gly
305             310             315             320 aca gag acc acc tca acc acg ata gaa tgg gcg atg tcg ctg ctg ctg     1008
Thr Glu Thr Thr Ser Thr Thr Ile Glu Trp Ala Met Ser Leu Leu Leu
            325             330             335 aac cac ccg gcg gcg ctc aag aag gcc cag gcc gag atc gac gcg tcc     1056
Asn His Pro Ala Ala Leu Lys Lys Ala Gln Ala Glu Ile Asp Ala Ser
            340             345             350 atc ggg acc tcc cgc atg gtt gcc gcc gac gac gtg ccc cgc ctc agc     1104
Ile Gly Thr Ser Arg Met Val Ala Ala Asp Asp Val Pro Arg Leu Ser
            355             360             365 tac ctc cag tgc atc atc aac gag acg cta cgc atg tac ccg gcg gcg     1152
Tyr Leu Gln Cys Ile Ile Asn Glu Thr Leu Arg Met Tyr Pro Ala Ala
    370             375             380 ccg ctg ctg ctg ccg cac gag tcc tcc gcc gac tgc aag gtc ggc ggc     1200
Pro Leu Leu Leu Pro His Glu Ser Ser Ala Asp Cys Lys Val Gly Gly
385             390             395             400 tac gac gtg ccg agc ggc acc atg ctg atc gtg aac gcg tac gcc atc     1248
Tyr Asp Val Pro Ser Gly Thr Met Leu Ile Val Asn Ala Tyr Ala Ile
            405             410             415 cac agg gac ccg gcg acg tgg gag gac ccg acg gcg ttc cgg ccg gag     1296
His Arg Asp Pro Ala Thr Trp Glu Asp Pro Thr Ala Phe Arg Pro Glu
            420             425             430 cgg ttc gag gac ggc aag ggc gac ggg ctg ctg ctg atg ccg ttc ggg     1344
Arg Phe Glu Asp Gly Lys Gly Asp Gly Leu Leu Leu Met Pro Phe Gly
            435             440             445 atg ggg cgg cgg agg tgc ccc ggc gag gcg ctg gcg ctg cag acg gtc     1392
Met Gly Arg Arg Arg Cys Pro Gly Glu Ala Leu Ala Leu Gln Thr Val
    450             455             460 ggg gtt gtt ctc ggg atg ctg gtg cag tgc ttc gac tgg gat cgg gtg     1440
Gly Val Val Leu Gly Met Leu Val Gln Cys Phe Asp Trp Asp Arg Val
465             470             475             480 gac ggc gtg gag gtg gac atg acg gag ggg gtg ggg atc acc atg ccc     1488
Asp Gly Val Glu Val Asp Met Thr Glu Gly Val Gly Ile Thr Met Pro
            485             490             495 aag tcc gtg gct ttg gag gcc gtg tgt agg ccg cgt gct gcc atg cgc     1536
Lys Ser Val Ala Leu Glu Ala Val Cys Arg Pro Arg Ala Ala Met Arg
            500             505             510 gat gtc ctt cac aag ctg tga                                         1557
Asp Val Leu His Lys Leu
            515
```

```
<210> SEQ ID NO 14
<211> LENGTH: 518
<212> TYPE: PRT
<213> ORGANISM: Hordeum vulgare

<400> SEQUENCE: 14

Met Asp Lys Ala Ser Ile Ala Val Leu Ser Leu Ala Phe Leu Phe Leu
1               5               10              15

Leu His Tyr Ile Leu Gly Lys Arg Ser Asp Gly Arg Arg Gly Lys Gly
            20              25              30

Lys Gly Ala Val Gln Leu Pro Pro Ser Pro Pro Ala Val Pro Phe Phe
            35              40              45

Gly His Leu His Leu Val Glu Lys Pro Leu His Ala Ala Leu Cys Arg
```

-continued

```
             50               55               60

Leu Gly Ala Arg His Gly Pro Val Phe Ser Leu Arg Leu Gly Ala Arg
65                  70               75                  80

Asn Ala Val Val Val Ser Ser Pro Ala Cys Ala Arg Glu Cys Phe Thr
                85               90               95

Asp His Asp Val Ala Phe Ala Asn Arg Pro Gln Phe Pro Ser Gln Met
            100              105              110

Leu Val Ser Tyr Gly Gly Thr Ser Leu Val Ser Ser Ser Tyr Gly Pro
        115              120              125

His Trp Arg Asn Leu Arg Arg Val Ala Ala Val Arg Leu Leu Ser Ala
    130              135              140

His Arg Val Ala Gly Met Ser Gly Val Ile Ala Ala Glu Val Arg Ala
145              150              155              160

Met Ala Arg Arg Leu Tyr Arg Ala Ala Ala Ala Ser Pro Gly Gly Ala
                165              170              175

Ala Arg Val Glu Leu Lys Arg Ser Leu Phe Glu Leu Ser Leu Ser Val
            180              185              190

Leu Met Glu Thr Ile Ala Arg Thr Lys Gly Thr Arg Ser Glu Ala Asp
        195              200              205

Ala Asp Thr Asp Met Ser Leu Glu Ala Gln Glu Phe Lys Gln Val Val
    210              215              220

Asp Glu Ile Ile Pro Leu Ile Gly Ala Ala Asn Leu Trp Asp Tyr Leu
225              230              235              240

Pro Val Met Arg Trp Phe Asp Val Ser Gly Val Arg Ser Arg Ile Leu
                245              250              255

Ala Thr Val Ser Arg Arg Asp Ala Phe Leu His Arg Leu Ile Asp Ala
            260              265              270

Glu Arg Arg Arg Met Glu Glu Gly Gly Asp Glu Gly Glu Lys Lys Ser
        275              280              285

Met Ile Ala Val Leu Leu Thr Leu Gln Lys Thr Glu Pro Glu Leu Tyr
    290              295              300

Thr Asp Gln Met Ile Ile Ala Leu Cys Ala Asn Met Phe Val Ala Gly
305              310              315              320

Thr Glu Thr Thr Ser Thr Thr Ile Glu Trp Ala Met Ser Leu Leu Leu
                325              330              335

Asn His Pro Ala Ala Leu Lys Lys Ala Gln Ala Glu Ile Asp Ala Ser
            340              345              350

Ile Gly Thr Ser Arg Met Val Ala Ala Asp Asp Val Pro Arg Leu Ser
        355              360              365

Tyr Leu Gln Cys Ile Ile Asn Glu Thr Leu Arg Met Tyr Pro Ala Ala
    370              375              380

Pro Leu Leu Leu Pro His Glu Ser Ser Ala Asp Cys Lys Val Gly Gly
385              390              395              400

Tyr Asp Val Pro Ser Gly Thr Met Leu Ile Val Asn Ala Tyr Ala Ile
                405              410              415

His Arg Asp Pro Ala Thr Trp Glu Asp Pro Thr Ala Phe Arg Pro Glu
            420              425              430

Arg Phe Glu Asp Gly Lys Gly Asp Gly Leu Leu Leu Met Pro Phe Gly
        435              440              445

Met Gly Arg Arg Arg Cys Pro Gly Glu Ala Leu Ala Leu Gln Thr Val
    450              455              460

Gly Val Val Leu Gly Met Leu Val Gln Cys Phe Asp Trp Asp Arg Val
465              470              475              480
```

-continued

```
Asp Gly Val Glu Val Asp Met Thr Glu Gly Val Gly Ile Thr Met Pro
                485                 490                 495

Lys Ser Val Ala Leu Glu Ala Val Cys Arg Pro Arg Ala Ala Met Arg
            500                 505                 510

Asp Val Leu His Lys Leu
        515

<210> SEQ ID NO 15
<211> LENGTH: 1557
<212> TYPE: DNA
<213> ORGANISM: Hordeum vulgare
<220> FEATURE:
<221> NAME/KEY: CDS
<222> LOCATION: (1)..(1557)

<400> SEQUENCE: 15 atg gat aag gca tac att gcc atc ctc tcc ttc act ttc ctc ttc ctg      48
Met Asp Lys Ala Tyr Ile Ala Ile Leu Ser Phe Thr Phe Leu Phe Leu
1               5                   10                  15 ctc cac tac att cta ggc aag gtc agc aat ggc agg cgc agc aag ggt      96
Leu His Tyr Ile Leu Gly Lys Val Ser Asn Gly Arg Arg Ser Lys Gly
            20                  25                  30 gac gtc cag ctg ccg ccg agc ccc agg ccc atc ccg ttc ctc ggc cac     144
Asp Val Gln Leu Pro Pro Ser Pro Arg Pro Ile Pro Phe Leu Gly His
        35                  40                  45 ctc cac ctc ctg gag aag ccg ttc cac gtc gct ctg tgc cgc ctc gcc     192
Leu His Leu Leu Glu Lys Pro Phe His Val Ala Leu Cys Arg Leu Ala
    50                  55                  60 gcg cgc ctc ggc ccg gtc ttc tcg ctg cgg ctc ggc tcg cgc cgc gcc     240
Ala Arg Leu Gly Pro Val Phe Ser Leu Arg Leu Gly Ser Arg Arg Ala
65                  70                  75                  80 gtg gtg gtg tcc tcg gcg gac tgc gcc agg gag tgc ttc acg gag cac     288
Val Val Val Ser Ser Ala Asp Cys Ala Arg Glu Cys Phe Thr Glu His
                85                  90                  95 gac gtg atc ttc gcc aac agg ccc cag ttc ccc tcg cag ctg ctc gtg     336
Asp Val Ile Phe Ala Asn Arg Pro Gln Phe Pro Ser Gln Leu Leu Val
            100                 105                 110 tcc ttc gac ggc acc gcg ctc tcc acg tcc agc tac ggc ccg cac tgg     384
Ser Phe Asp Gly Thr Ala Leu Ser Thr Ser Ser Tyr Gly Pro His Trp
        115                 120                 125 cgc aac ctc cgt cgc gtc gcc gcc gtg cag ctg ctc tcc gcg cac cgc     432
Arg Asn Leu Arg Arg Val Ala Ala Val Gln Leu Leu Ser Ala His Arg
    130                 135                 140 gtc gcc tgc atg tcc ggc gtc atc gcc ggc gag gtg cgc gcc atg gcc     480
Val Ala Cys Met Ser Gly Val Ile Ala Gly Glu Val Arg Ala Met Ala
145                 150                 155                 160 cgc cgg ctc ttc cgc tcc gcc gag gcg tcc ccc ggc ggc ggt ggc gcc     528
Arg Arg Leu Phe Arg Ser Ala Glu Ala Ser Pro Gly Gly Gly Gly Ala
                165                 170                 175 gcg cgg gtc cag ctg aag cgg agg ctg ttc gag ctc tca ttg agc gtg     576
Ala Arg Val Gln Leu Lys Arg Arg Leu Phe Glu Leu Ser Leu Ser Val
            180                 185                 190 ctc atg gag acc atc gct cag acc aag ggg acc cgg tcg gag gcc gac     624
Leu Met Glu Thr Ile Ala Gln Thr Lys Gly Thr Arg Ser Glu Ala Asp
        195                 200                 205 gcc gac acg gac atg tcc gtg gag gcc cag gag ttc aag aag gtg gtg     672
Ala Asp Thr Asp Met Ser Val Glu Ala Gln Glu Phe Lys Lys Val Val
    210                 215                 220 gac gag atc atc ccg tac ctc ggc gcc gcc aac acg tgg gac tac ctg     720
Asp Glu Ile Ile Pro Tyr Leu Gly Ala Ala Asn Thr Trp Asp Tyr Leu
```

```
                225                  230                  235                  240
ccg gtg gtg cgg tgg ttc gac gtg ttc ggc gtc agg aac aag atc ctg          768
Pro Val Val Arg Trp Phe Asp Val Phe Gly Val Arg Asn Lys Ile Leu
                245                  250                  255 gcc gcc gtg agc agg agg gac gcc ttc ctc cat cgt ctc atc gac gcc          816
Ala Ala Val Ser Arg Arg Asp Ala Phe Leu His Arg Leu Ile Asp Ala
                260                  265                  270 gag cgg agg agg ctg gac ggc ggc ggc gcc gaa gcc gac aag aag agc          864
Glu Arg Arg Arg Leu Asp Gly Gly Gly Ala Glu Ala Asp Lys Lys Ser
                275                  280                  285 atg atc gcc gtg ctg ctc act ctg cag aag acg gag ccg gag gtg tac          912
Met Ile Ala Val Leu Leu Thr Leu Gln Lys Thr Glu Pro Glu Val Tyr
            290                  295                  300 acc gat act atg atc acg gct ctc tgc tcg aat tta ttt ggg gcc gga          960
Thr Asp Thr Met Ile Thr Ala Leu Cys Ser Asn Leu Phe Gly Ala Gly
305                  310                  315                  320 acg gag acc acg tcg acg acg acg gag tgg gcc atg tcg ctg ctt ctg         1008
Thr Glu Thr Thr Ser Thr Thr Thr Glu Trp Ala Met Ser Leu Leu Leu
                325                  330                  335 aac cac ccg gcg gcg ctg agg aag gcg cag gcc gag atc gac gcg gcc         1056
Asn His Pro Ala Ala Leu Arg Lys Ala Gln Ala Glu Ile Asp Ala Ala
                340                  345                  350 gtg ggc acc tcc cgg ctg gtg acc gcc gac gac gtg ccc cgg ctc gcc         1104
Val Gly Thr Ser Arg Leu Val Thr Ala Asp Asp Val Pro Arg Leu Ala
                355                  360                  365 tac ctg cag tgc atc gtg agc gag acg ctg cgg ctg tac ccg gcg acg         1152
Tyr Leu Gln Cys Ile Val Ser Glu Thr Leu Arg Leu Tyr Pro Ala Thr
            370                  375                  380 ccg atg ctg ctg ccg cac caa tcg tcg gcg gac tgc aag gtg ggc ggc         1200
Pro Met Leu Leu Pro His Gln Ser Ser Ala Asp Cys Lys Val Gly Gly
385                  390                  395                  400 tac aac gtg ccg agc ggc acg atg ctg atg gtg aac gcg tac gcc atc         1248
Tyr Asn Val Pro Ser Gly Thr Met Leu Met Val Asn Ala Tyr Ala Ile
                405                  410                  415 cac cgc gac ccg gcg gcg tgg gag cgg ccg ctg gag ttc gtc ccg gag         1296
His Arg Asp Pro Ala Ala Trp Glu Arg Pro Leu Glu Phe Val Pro Glu
                420                  425                  430 cgg ttc gag gac ggc aag gcc gag ggg cgg ttc atg atc ccg ttc ggg         1344
Arg Phe Glu Asp Gly Lys Ala Glu Gly Arg Phe Met Ile Pro Phe Gly
                435                  440                  445 atg ggc cgc cgg cgg tgc ccc ggg gag acg ctg gcg ctg cgg acc atc         1392
Met Gly Arg Arg Arg Cys Pro Gly Glu Thr Leu Ala Leu Arg Thr Ile
            450                  455                  460 ggc atg gtg ctg gcc acg ctg gtg cag tgc ttc gac tgg gac cgc gtc         1440
Gly Met Val Leu Ala Thr Leu Val Gln Cys Phe Asp Trp Asp Arg Val
465                  470                  475                  480 gac ggc aag gag gtg gac atg acg gag agc ggc ggg ctc acc atc ccc         1488
Asp Gly Lys Glu Val Asp Met Thr Glu Ser Gly Gly Leu Thr Ile Pro
                485                  490                  495 aag gcc gtg ccg ctc gag gcc gtc tgc agg ccg cgc gcg gcc atg cgc         1536
Lys Ala Val Pro Leu Glu Ala Val Cys Arg Pro Arg Ala Ala Met Arg
                500                  505                  510 gac gtg ctc cag agc ctc tga                                             1557
Asp Val Leu Gln Ser Leu
            515
```

<210> SEQ ID NO 16
<211> LENGTH: 518
<212> TYPE: PRT
<213> ORGANISM: Hordeum vulgare -continued

<400> SEQUENCE: 16

```
Met Asp Lys Ala Tyr Ile Ala Ile Leu Ser Phe Thr Phe Leu Phe Leu
1               5                   10                  15

Leu His Tyr Ile Leu Gly Lys Val Ser Asn Gly Arg Arg Ser Lys Gly
            20                  25                  30

Asp Val Gln Leu Pro Pro Ser Pro Arg Pro Ile Pro Phe Leu Gly His
            35                  40                  45

Leu His Leu Leu Glu Lys Pro Phe His Val Ala Leu Cys Arg Leu Ala
        50                  55                  60

Ala Arg Leu Gly Pro Val Phe Ser Leu Arg Leu Gly Ser Arg Arg Ala
65                  70                  75                  80

Val Val Val Ser Ser Ala Asp Cys Ala Arg Glu Cys Phe Thr Glu His
                85                  90                  95

Asp Val Ile Phe Ala Asn Arg Pro Gln Phe Pro Ser Gln Leu Leu Val
                100                 105                 110

Ser Phe Asp Gly Thr Ala Leu Ser Thr Ser Ser Tyr Gly Pro His Trp
            115                 120                 125

Arg Asn Leu Arg Arg Val Ala Ala Val Gln Leu Leu Ser Ala His Arg
        130                 135                 140

Val Ala Cys Met Ser Gly Val Ile Ala Gly Glu Val Arg Ala Met Ala
145                 150                 155                 160

Arg Arg Leu Phe Arg Ser Ala Glu Ala Ser Pro Gly Gly Gly Gly Ala
                165                 170                 175

Ala Arg Val Gln Leu Lys Arg Arg Leu Phe Glu Leu Ser Leu Ser Val
                180                 185                 190

Leu Met Glu Thr Ile Ala Gln Thr Lys Gly Thr Arg Ser Glu Ala Asp
            195                 200                 205

Ala Asp Thr Asp Met Ser Val Glu Ala Gln Glu Phe Lys Lys Val Val
        210                 215                 220

Asp Glu Ile Ile Pro Tyr Leu Gly Ala Ala Asn Thr Trp Asp Tyr Leu
225                 230                 235                 240

Pro Val Val Arg Trp Phe Asp Val Phe Gly Val Arg Asn Lys Ile Leu
                245                 250                 255

Ala Ala Val Ser Arg Arg Asp Ala Phe Leu His Arg Leu Ile Asp Ala
                260                 265                 270

Glu Arg Arg Arg Leu Asp Gly Gly Gly Ala Glu Ala Asp Lys Lys Ser
        275                 280                 285

Met Ile Ala Val Leu Leu Thr Leu Gln Lys Thr Glu Pro Glu Val Tyr
        290                 295                 300

Thr Asp Thr Met Ile Thr Ala Leu Cys Ser Asn Leu Phe Gly Ala Gly
305                 310                 315                 320

Thr Glu Thr Thr Ser Thr Thr Thr Glu Trp Ala Met Ser Leu Leu Leu
                325                 330                 335

Asn His Pro Ala Ala Leu Arg Lys Ala Gln Ala Glu Ile Asp Ala Ala
            340                 345                 350

Val Gly Thr Ser Arg Leu Val Thr Ala Asp Asp Val Pro Arg Leu Ala
            355                 360                 365

Tyr Leu Gln Cys Ile Val Ser Glu Thr Leu Arg Leu Tyr Pro Ala Thr
        370                 375                 380

Pro Met Leu Leu Pro His Gln Ser Ser Ala Asp Cys Lys Val Gly Gly
385                 390                 395                 400

Tyr Asn Val Pro Ser Gly Thr Met Leu Met Val Asn Ala Tyr Ala Ile
```

-continued

```
                     405              410              415
His Arg Asp Pro Ala Ala Trp Glu Arg Pro Leu Glu Phe Val Pro Glu
             420              425              430

Arg Phe Glu Asp Gly Lys Ala Glu Gly Arg Phe Met Ile Pro Phe Gly
         435              440              445

Met Gly Arg Arg Arg Cys Pro Gly Glu Thr Leu Ala Leu Arg Thr Ile
     450              455              460

Gly Met Val Leu Ala Thr Leu Val Gln Cys Phe Asp Trp Asp Arg Val
465              470              475              480

Asp Gly Lys Glu Val Asp Met Thr Glu Ser Gly Gly Leu Thr Ile Pro
             485              490              495

Lys Ala Val Pro Leu Glu Ala Val Cys Arg Pro Arg Ala Ala Met Arg
         500              505              510

Asp Val Leu Gln Ser Leu
     515

<210> SEQ ID NO 17
<211> LENGTH: 23
<212> TYPE: DNA
<213> ORGANISM: Artificial
<220> FEATURE:
<223> OTHER INFORMATION: Synthetic DNA

<400> SEQUENCE: 17
caacctgaga cctcaagtgt cac                                           23

<210> SEQ ID NO 18
<211> LENGTH: 21
<212> TYPE: DNA
<213> ORGANISM: Artificial
<220> FEATURE:
<223> OTHER INFORMATION: Synthetic DNA

<400> SEQUENCE: 18
gtactacctg gatccacgag c                                             21

<210> SEQ ID NO 19
<211> LENGTH: 35
<212> TYPE: DNA
<213> ORGANISM: Artificial
<220> FEATURE:
<223> OTHER INFORMATION: Synthetic DNA

<400> SEQUENCE: 19
aaggagatat acatatggat aaggcgtaca ttgcc                              35

<210> SEQ ID NO 20
<211> LENGTH: 35
<212> TYPE: DNA
<213> ORGANISM: Artificial
<220> FEATURE:
<223> OTHER INFORMATION: Synthetic DNA

<400> SEQUENCE: 20
gtggtggtgc tcgagtcaga ggctctgaag cacgt                              35

<210> SEQ ID NO 21
<211> LENGTH: 2091
<212> TYPE: DNA
<213> ORGANISM: Triticum aestivum

<400> SEQUENCE: 21
```

-continued

```
atgagggact cggcgctcga cctgctggcg gcgctgctca cgggccgggc ccgccggcc      60 gccgccgacg gggaccagaa ccgccgcctg ctcgcgctgc tcgccacctc cctcgccgtg     120
ctcgtcggct gcggcgtcgc gctcctcttc cgccgctcct cctccggcgc cgcgccgctc     180
gcccacaagt ccgccgcggc caagcccctc gcagcgaaga aggaccagga gcccgacccc     240
gacgacggcc gccagcgggt cgccctcttc ttcggcacgc agaccggcac cgccgagggc     300
ttcgccaagg cgctcgcgga ggaggccaag gccaggtacg acaaggccgt cttcaaggtg     360
ctcgatctgg atgactatgc cgcggaggac gaggagtacg aggagaagct caagaaggag     420
aacatcgcct tcttcttcct cgcaacgtat ggggacggtg agccaaccga caatgccgcc     480
agattctaca aatggttctc cgagggaaac gagagggggtg agtggttgag caacctcaag     540
ttcggggtgt ttgctcttgg aataggcag tacgagcatt tcaacaaggt cggaaaggag      600
gtcgatcagc tcctcgccga acaaggtgga aagcgcatag ttcctgttgg ccttggagat     660
gacgatcaat gcattgagga tgacttcaat gcctggaagg aactactgtg gccagaattg     720
gacaaactgc tccgcgttga agataattct tcaacagcac aatctcctta cacagctgct     780
attccgcaat atagagttgt gcttaccaaa ccagaggatg ccacacatat caacaagtct     840
ttcagtctta gcaatggtca tgtcgtctac gacagtcaac atccttgcag ggcaaatgtg     900
gctgtgcgac gggagcttca cacaccagct tctgaccggt cctgcattca tttggaattt     960
gatattgcag gaactagcct tacatatgag actggagatc atgttggtgt gtacgcagaa    1020
aattcaattg agactgtaga ggaggcagaa aagctattag attattcacc agatacttat    1080
ttctcaattt atgctgacca agaggatggc actccacttt ttgggggctc tttgccacct    1140
cctttcccat ctccctgtac tgtgagggtt gcacttgcca gatatgccga tctgttgaat    1200
tcacctaaaa agagtgtttt acttgctttg gctgctcatg catctgatcc caaagaggcc    1260
gagcggctca gacatctagc atctcctgct ggaaagaagg agtattctca gtggataatc    1320
gctagtcaaa gaagtctctt ggaagttatt tcggagtttc catcggcgaa acctccgctt    1380
ggtgtcttct ttgcagctat tgctcctcgc cttcagccga gatactactc aatatcttcc    1440
tcaccaagaa tggcacctac aagaattcat gtaacatgtt cactagttca tgggcaaacc    1500
ccaactggaa ggatccataa aggagtttgt tctacttgga tgaagaattc aactcccttg    1560
gaagagagcc aagaatgtag ctgggctcca atttttgtga ggcagtcaaa cttcaaattg    1620
cctgctgatc ccacagtgcc tgttataatg gtaggccctg ggactggcct tgcacctttc    1680
aggggcttct tacaggaaag attagcttta aaagagaccg gggtggaact gggccgtgcc    1740
atcctgtttt tcgggtgcag aaaccgccag atggacttca tatatgagga tgagctgaac    1800
aactttgccg aatccggagc cctgtctgag ttggtcgtcg cctttttctcg tgagggtcct    1860 acaaaggagt acgtccaaca taaaatggca gagaaggctg cagagctgtg gagcattgtt    1920
tcccagggcg gctatgtgta cgtctgcggc gacgccaagg gcatggcgag agacgtgcac    1980
cgcgcgctgc acaccatagt tcaggagcag ggatctctgg acagctccaa ggcggagggc    2040
tatgtgaaaa accttcagat ggaagggaga tacctgagag acgtctggta a            2091
```

<210> SEQ ID NO 22
<211> LENGTH: 2112
<212> TYPE: DNA
<213> ORGANISM: Triticum aestivum

<400> SEQUENCE: 22

```
atggactccg ccgccgcggg gatgagggac tcggcgctcg acctgctggc ggcgctgctc       60
```

-continued

```
acgggccggg  ccccgccggc  cgccgccgac  ggggaccaga  accgccgcct  gctcgcgctg      120
ctcgccacct  ccctcgccgt  gctcgtcggc  tgcggcgtcg  cgctcctctt  ccgccgctcc      180
tcctccggcg  ccgcgccgct  cgcccacaag  tccgccgcgg  ccaagcccct  cgcagcgaag      240
aaggaccagg  agcccgaccc  cgacgacggc  cgccagcggg  tcgccctctt  cttcggcacg      300
cagaccggca  ccgccgaggg  cttcgccaag  gcgctcgcgg  aggaggccaa  ggccaggtac      360
gacaaggccg  tcttcaaggt  gctcgatctg  gatgactatg  ccgcggagga  cgaggagtac      420
gaggagaagc  tcaagaagga  gaacatcgcc  ttcttcttcc  tcgcaacgta  tggggacggt      480
gagccaaccg  acaatgccgc  cagattctac  aaatggttct  ccgagggaaa  cgagaggggt      540
gagtggttga  gcaacctcaa  gttcggggtg  tttgctcttg  ggaataggca  gtacgagcat      600
ttcaacaagg  tcggaaagga  ggtcgatcag  ctcctcgccg  aacaaggtgg  aaagcgcata      660
gttcctgttg  gccttggaga  tgacgatcaa  tgcattgagg  atgacttcaa  tgcctggaag      720
gaactactgt  ggccagaatt  ggacaaactg  ctccgcgttg  aagataattc  ttcaacagca      780
caatctcctt  acacagctgc  tattccgcaa  tatagagttg  tgcttaccaa  accagaggat      840
gccacacata  tcaacaagtc  tttcagtctt  agcaatggtc  atgtcgtcta  cgacagtcaa      900
catccttgca  gggcaaatgt  ggctgtgcga  cgggagcttc  acacaccagc  ttctgaccgg      960
tcctgcattc  atttggaatt  tgatattgca  ggaactagcc  ttacatatga  gactggagat     1020
catgttggtg  tgtacgcaga  aaattcaatt  gagactgtag  aggaggcaga  aaagctatta     1080
gattattcac  cagatactta  tttctcaatt  tatgctgacc  aagaggatgg  cactccactt     1140
tttgggggct  ctttgccacc  tcctttccca  tctccctgta  ctgtgagggt  tgcacttgcc     1200
agatatgccg  atctgttgaa  ttcacctaaa  aagagtgttt  tacttgcttt  ggctgctcat     1260
gcatctgatc  ccaaagaggc  cgagcggctc  agacatctag  catctcctgc  tggaaagaag     1320
gagtattctc  agtggataat  cgctagtcaa  agaagtctct  tggaagttat  ttcggagttt     1380
ccatcggcga  aacctccgct  tggtgtcttc  tttgcagcta  ttgctcctcg  ccttcagccg     1440
agatactact  caatatcttc  ctcaccaaga  atggcaccta  caagaattca  tgtaacatgt     1500
tcactagttc  atgggcaaac  cccaactgga  aggatccata  aaggagtttg  ttctacttgg     1560
atgaagaatt  caactccctt  ggaagagagc  caagaatgta  gctgggctcc  aattttgtg      1620 aggcagtcaa  acttcaaatt  gcctgctgat  cccacagtgc  ctattataat  ggtaggccct     1680
gggactggcc  ttgcaccttt  caggggcttc  ttacaggaaa  gattagcttt  aaaagagacc     1740
ggggtggaac  tgggccgtgc  catcctgttt  ttcgggtgca  gaaaccgcca  gatggacttc     1800
atatatgagg  atgagctgaa  caactttgcc  gaatccggag  ccctgtctga  gttggtcgtc     1860
gccttttctc  gtgagggtcc  tacaaaggag  tacgtccaac  ataaaatggc  agagaaggct     1920
gcagagctgt  ggagcattgt  ttcccagggc  ggctatgtgt  acgtctgcgg  cgacgccaag     1980
ggcatggcga  gagacgtgca  ccgcgcgctg  cacaccatag  ttcaggagca  gggatctctg     2040
gacagctcca  aggcggaggg  ctatgtgaaa  aaccttcaga  tggaagggag  atacctgaga     2100
gacgtctggt  aa                                                            2112
```

<210> SEQ ID NO 23
<211> LENGTH: 21
<212> TYPE: DNA
<213> ORGANISM: Artificial
<220> FEATURE:
<223> OTHER INFORMATION: Synthetic DNA -continued

<400> SEQUENCE: 23
cacgcgtccg atcgaaccaa c                                                              21

<210> SEQ ID NO 24
<211> LENGTH: 26
<212> TYPE: DNA
<213> ORGANISM: Artificial
<220> FEATURE:
<223> OTHER INFORMATION: Synthetic DNA

<400> SEQUENCE: 24
cgatgaatcg tcatcctctg ttccac                                                         26

<210> SEQ ID NO 25
<211> LENGTH: 35
<212> TYPE: DNA
<213> ORGANISM: Artificial
<220> FEATURE:
<223> OTHER INFORMATION: Synthetic DNA

<400> SEQUENCE: 25
aaggagatat acatatggac tccgccgccg cgggg                                               35

<210> SEQ ID NO 26
<211> LENGTH: 35
<212> TYPE: DNA
<213> ORGANISM: Artificial
<220> FEATURE:
<223> OTHER INFORMATION: Synthetic DNA

<400> SEQUENCE: 26
ctttaccaga ctcgattacc agacgtctct caggt                                               35

<210> SEQ ID NO 27
<211> LENGTH: 35
<212> TYPE: DNA
<213> ORGANISM: Artificial
<220> FEATURE:
<223> OTHER INFORMATION: Synthetic DNA

<400> SEQUENCE: 27
aaggagatat acatatggct aagaagactt cttct                                               35

<210> SEQ ID NO 28
<211> LENGTH: 35
<212> TYPE: DNA
<213> ORGANISM: Artificial
<220> FEATURE:
<223> OTHER INFORMATION: Synthetic DNA

<400> SEQUENCE: 28
gtggtggtgc tcgagtcaga ggctctgaag cacgt                                               35

<210> SEQ ID NO 29
<211> LENGTH: 35
<212> TYPE: DNA
<213> ORGANISM: Artificial
<220> FEATURE:
<223> OTHER INFORMATION: Synthetic DNA

<400> SEQUENCE: 29
aaggagatat acatatggac cagaaccgcc gcctg                                               35

<210> SEQ ID NO 30
<211> LENGTH: 35

```
<212> TYPE: DNA
<213> ORGANISM: Artificial
<220> FEATURE:
<223> OTHER INFORMATION: Synthetic DNA

<400> SEQUENCE: 30
tttaccagac tcgagttacc agacgtctct caggt                          35

<210> SEQ ID NO 31
<211> LENGTH: 35
<212> TYPE: DNA
<213> ORGANISM: Artificial
<220> FEATURE:
<223> OTHER INFORMATION: Synthetic DNA

<400> SEQUENCE: 31
tacaactaca tctagaatgg ataaggcgta cattg                          35

<210> SEQ ID NO 32
<211> LENGTH: 35
<212> TYPE: DNA
<213> ORGANISM: Artificial
<220> FEATURE:
<223> OTHER INFORMATION: Synthetic DNA

<400> SEQUENCE: 32
ggggaaattc gagctctcag aggctctgaa gcacg                          35

<210> SEQ ID NO 33
<211> LENGTH: 22
<212> TYPE: DNA
<213> ORGANISM: Artificial
<220> FEATURE:
<223> OTHER INFORMATION: Synthetic DNA

<400> SEQUENCE: 33
gctctccaac aacattgcca ac                                        22

<210> SEQ ID NO 34
<211> LENGTH: 21
<212> TYPE: DNA
<213> ORGANISM: Artificial
<220> FEATURE:
<223> OTHER INFORMATION: Synthetic DNA

<400> SEQUENCE: 34
gcttctgcct gtcacatacg c                                         21

<210> SEQ ID NO 35
<211> LENGTH: 20
<212> TYPE: DNA
<213> ORGANISM: Artificial
<220> FEATURE:
<223> OTHER INFORMATION: Synthetic DNA

<400> SEQUENCE: 35
ctctgcgcga atttatttgg                                           20

<210> SEQ ID NO 36
<211> LENGTH: 20
<212> TYPE: DNA
<213> ORGANISM: Artificial
<220> FEATURE:
<223> OTHER INFORMATION: Synthetic DNA

<400> SEQUENCE: 36
```

-continued

```
tcacgatgca ctgcaggtag                                         20

<210> SEQ ID NO 37
<211> LENGTH: 23
<212> TYPE: DNA
<213> ORGANISM: Artificial
<220> FEATURE:
<223> OTHER INFORMATION: Synthetic DNA

<400> SEQUENCE: 37
caacctgaga cctcaagtgt cac                                     23

<210> SEQ ID NO 38
<211> LENGTH: 23
<212> TYPE: DNA
<213> ORGANISM: Artificial
<220> FEATURE:
<223> OTHER INFORMATION: Synthetic DNA

<400> SEQUENCE: 38
cagtgctacc gcaagatagc tac                                     23

<210> SEQ ID NO 39
<211> LENGTH: 513
<212> TYPE: PRT
<213> ORGANISM: Oryza sativa Indica Group

<400> SEQUENCE: 39

Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
            20                  25                  30

Leu Pro Pro Gly Pro Pro Ala Val Pro Ile Leu Gly His Leu His Leu
        35                  40                  45

Val Lys Lys Pro Met His Ala Thr Met Ser Arg Leu Ala Glu Arg Tyr
    50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
    130                 135                 140

Met Ser Gly Leu Ile Ala Gly Glu Val Arg Ala Met Val Arg Arg Met
145                 150                 155                 160

Tyr Arg Ala Ala Ala Ala Ser Pro Ala Gly Ala Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
        195                 200                 205

Ser Val Glu Ala Gln Glu Phe Lys Gln Val Val Asp Glu Ile Ile Pro
    210                 215                 220

His Ile Gly Ala Ala Asn Leu Trp Asp Tyr Leu Pro Ala Leu Arg Trp
225                 230                 235                 240
```

-continued

```
Phe Asp Val Phe Gly Val Arg Arg Lys Ile Leu Ala Ala Val Ser Arg
              245             250             255

Arg Asp Ala Phe Leu Arg Arg Leu Ile Asp Ala Glu Arg Arg Arg Leu
              260             265             270

Asp Asp Gly Asp Glu Gly Glu Lys Lys Ser Met Ile Ala Val Leu Leu
              275             280             285

Thr Leu Gln Lys Thr Glu Pro Glu Val Tyr Thr Asp Asn Met Ile Thr
     290             295             300

Ala Leu Thr Ala Asn Leu Phe Gly Ala Gly Thr Glu Thr Thr Ser Thr
305             310             315             320

Thr Ser Glu Trp Ala Met Ser Leu Leu Leu Asn His Pro Asp Thr Leu
              325             330             335

Lys Lys Ala Gln Ala Glu Ile Asp Ala Ser Val Gly Asn Ser Arg Leu
              340             345             350

Ile Thr Ala Asp Asp Val Thr Arg Leu Gly Tyr Leu Gln Cys Ile Val
              355             360             365

Arg Glu Thr Leu Arg Leu Tyr Pro Ala Ala Pro Met Leu Leu Pro His
     370             375             380

Glu Ser Ser Ala Asp Cys Lys Val Gly Gly Tyr Asn Ile Pro Arg Gly
385             390             395             400

Ser Met Leu Leu Ile Asn Ala Tyr Ala Ile His Arg Asp Pro Ala Val
              405             410             415

Trp Glu Glu Pro Glu Lys Phe Met Pro Glu Arg Phe Glu Asp Gly Gly
              420             425             430

Cys Asp Gly Asn Leu Leu Met Pro Phe Gly Met Gly Arg Arg Arg Cys
              435             440             445

Pro Gly Glu Thr Leu Ala Leu Arg Thr Val Gly Leu Val Leu Gly Thr
     450             455             460

Leu Ile Gln Cys Phe Asp Trp Glu Arg Val Asp Gly Val Glu Val Asp
465             470             475             480

Met Thr Glu Gly Gly Gly Leu Thr Ile Pro Lys Val Val Pro Leu Glu
              485             490             495

Ala Met Cys Arg Pro Arg Asp Ala Met Gly Gly Val Leu Arg Glu Leu
              500             505             510

Val
```